(12) United States Patent
Attala et al.

(10) Patent No.: US 9,079,854 B2
(45) Date of Patent: *Jul. 14, 2015

(54) HYDRAZONE MODULATORS OF CANNABINOID RECEPTORS

(71) Applicant: THE CLEVELAND CLINIC FOUNDATION, Cleveland, OH (US)

(72) Inventors: Mohamed Naguib Attala, Houston, TX (US); Philippe Diaz, Missoula, MT (US)

(73) Assignee: The Cleveland Clinic Foundation, Cleveland, OH (US)

( * ) Notice: Subject to any disclaimer, the term of this patent is extended or adjusted under 35 U.S.C. 154(b) by 33 days.

This patent is subject to a terminal disclaimer.

(21) Appl. No.: 13/647,134

(22) Filed: Oct. 8, 2012

(65) Prior Publication Data

US 2013/0184275 A1 Jul. 18, 2013

Related U.S. Application Data

(63) Continuation of application No. 12/668,867, filed as application No. PCT/US2008/069989 on Jul. 14, 2008, now Pat. No. 8,309,595.

(60) Provisional application No. 60/949,551, filed on Jul. 13, 2007, provisional application No. 61/032,828, filed on Feb. 29, 2008.

(51) Int. Cl.
| | |
|---|---|
| *A61K 31/4015* | (2006.01) |
| *C07D 209/34* | (2006.01) |
| *C07D 209/40* | (2006.01) |
| *C07D 409/12* | (2006.01) |
| *C07D 209/48* | (2006.01) |
| *C07D 413/12* | (2006.01) |
| *A61K 31/404* | (2006.01) |
| *A61K 45/06* | (2006.01) |
| *A61K 31/337* | (2006.01) |

(52) U.S. Cl.
CPC ............ *C07D 209/40* (2013.01); *A61K 31/337* (2013.01); *A61K 31/404* (2013.01); *A61K 45/06* (2013.01); *C07D 209/48* (2013.01); *C07D 409/12* (2013.01); *C07D 413/12* (2013.01)

(58) Field of Classification Search
CPC ..................................................... C07D 209/34
USPC .................................. 549/424, 426; 548/468
See application file for complete search history.

(56) References Cited

U.S. PATENT DOCUMENTS

| | | |
|---|---|---|
| 5,684,002 A | 11/1997 | Scherz et al. |
| 5,981,776 A | 11/1999 | Diaz et al. |
| 2007/0099990 A1 | 5/2007 | Ohkawa et al. |

FOREIGN PATENT DOCUMENTS

| | | |
|---|---|---|
| EP | 0816352 A1 | 9/2006 |
| WO | 9729100 A1 | 8/1997 |
| WO | 9824778 A1 | 6/1998 |
| WO | 2006097193 A1 | 9/2006 |

OTHER PUBLICATIONS

Naguib, et al. ChemMedChem. 2009, 4, 1615-1629.*
Szlosek-Pinaud, M., et al., "Efficient Synthetic Approach to Heterocycles Possessing the 3,3-Disubstituted-2,3-Dihydrobenzofuran Skeleton Via Diverse Palladium-Catalyzed Tandem Reactions", Tetrahedron, 2007, 63:3340-9.
Mukherjee, S., et al., "Species Comparison and Pharmacological Characterization of Rat and Human CB2 Cannabinoid Receptors", Eur J Pharmacol, 2004, 505:1-9.
Kim, S.H., et al., "An Experimental Model for Peripheral Neuropathy Produced by Segmental Spinal Nerve Ligation in the Rat", Pain, 1992,50:355-63.
Polomano, R.C., et al., "A Painful Peripheral Neuropathy in the Rat Produced by the Chemotherapeutic Drug Paclitaxel", Pain, 2001, 94:293-304.
Chaplan, S.R., et al., "Quantitative Assessment of Tactile Allodynia in the Rat Paw", J. Neurosci. Methods, 1994 53:55-63.
Dixon, W.J., "The Up-and-Down Method for Small Samples", J. Am. Stat. Assoc., 1965,60:967-78.
Hosohata,Y., et al., "AM630 Antagonism of Cannabinoid-Stimulated [35SjGTP Gamma S Binding in the Mouse Brain", Eur. J. Pharmacol, 1997, 321:RI-3.
Ross, R.A., et al., "Agonist-Inverse Agonist Characterization at CBI and CB2 Cannabinoid Receptors of L759633, L759656, and AM630", Br. J. Pharmacol., 1999, 126:665-72.
Gatley, S.J., et al., "1231-labeled AM251: A Radioiodinated Ligand Which Binds In Vivo to Mouse Brain Cannabinoid CBI Receptors", Eur J Pharmacol, 1996,307:331-8.
Ibrahim, M.M., "Activation ofCB2 Cannabinoid Receptors by AM1241 Inhibits Experimental Neuropathic Pain: Pain Inhibition by Receptors Not Present in the CNS", Proc. Natl. Acad. Sci. U.S.A., 2003,100:10529-33.
Ibrahim, M.M., et al., "CB2 Cannabinoid Receptor Activation Produces Antinociception by Stimulating Peripheral Release of Endogenous Opioids", Proc. Natl. Acad. Sci. U.S.A., 2005,102:3093-8.
Herzberg, U., et al., "The Analgesic Effects of R(+)-WIN 55,212-2 Mesylate, a High Affinity Cannabinoid Agonist, in a Rat Model of Neuropathic Pain", Neurosci Lett, 1997,221:157-60.
Warms, C.A., et al., "Treatments for Chronic Pain Associated with Spinal Cord Injuries: Many are tried, few are Helpful", Clin. J. Pain May-Jun. 2002; 18 (3):154-63.
Matsuda, L.A., et. al., "Structure of a Cannabinoid Receptor and Functional Expression of the Cloned cDNA", Nature Aug. 9, 1990; 346:561-4.
Munro, S., et. al., "Molecular Characterization of a Peripheral Receptor for Cannabinoids", Nature 1993; 365:61-5.

(Continued)

*Primary Examiner* — Shawquia Jackson
(74) *Attorney, Agent, or Firm* — Tarolli, Sundheim, Covell & Tummino LLP

(57) ABSTRACT

Hydrazone compounds which modulate cannabinoid receptors are presented. Pharmaceutical compositions containing these compounds, methods of using these compounds as modulators of cannabinoid receptors and processes for synthesizing these compounds are also described herein.

6 Claims, 14 Drawing Sheets

(56) References Cited

OTHER PUBLICATIONS

Gaoni,Y., et al., "Isolation, Structure, and Partial Synthesis of an Active Constituent of Hashish", J Am Chem Soc 1964; 86: 1646-7.
Di Marzo, V., et al., "The Endocannabinoid System and Its Therapeutic Exploitation", Nat Rev Drug Discov 2004; 3: 771-84.
Onaivi ,E.S., et al., "Discovery of the Presence and Functional Expression of Cannabinoid CB2 Receptors in Brain", Ann NY Acad Sci 2006; 1074: 514-536.
Fride, E., "Endocannabinoids in the Central Nervous System—An Overview. Prostaglandins Leukot Essent Fatty Acids", 2002; 66: 221-33.
Van Gaal, L.F. et al., "Effects of the Cannabinoid-1 Receptor Blocker Rimonabant on Weight Reduction and Cardiovascular Risk Factors in Overweight Patients: 1-Year Experience From the RIO-Europe Study", The Lancet D 2005; 365: 1389-1397.
Di Marzo, V.,et al., "Leptin-Regulated Endocannabinoids are Involved in Maintaining Food Intake", Nature 2001; 410: 822-5.
Maldonado, R.,et al., "Involvement of the Endocannabinoid System in Drug Addiction", Trends Neurosci 2006; 29: 225-32.
Kehl, L.J.,et al., "A Cannabinoid Agonist Differentially Attenuates Deep Tissue Hyperalgesia in Animal Models of Cancer and Inflammatory Muscle Pain", Pain 2003; 103: 175-86.
Idris, A.I., et al., "Regulation of Bone Mass, Bone Loss and Osteoclast Activity by Cannabinoid Receptors", Nat Med 2005; 11: 774-9.
Maccarrone, M., et al., "The Endocannabinoid System in Human Keratinocytes. Evidence That Anandamide Inhibits Epidermal Differentiation Through CB1 Receptor-Dependent Inhibition of Protein Kinase C, Activation Protein-1, and Transglutaminase", J Bioi Chem 2003; 278: 33896-903.
Wilkinson ,JD.,et al., "Cannabinoids Inhibit Human Keratinocyte Proliferation Through a Non-CB1/CB2 Mechanism and Have a Potential Therapeutic Value in the Treatment of Psoriasis", J Dermatol Sci 2007; 45: 87-92.
Blazquez, C.,et al., "Cannabinoid Receptors as Novel Targets for the Treatment of Melanoma", Faseb J 2006; 20: 2633-5.
Ferandin, Y.,et al., "3'-Substituted 7-Halogenoindirubins, A New Class of Cell Death Inducing Agents", J Med Chem 2006; 49: 4638-49.
Trang, T.,et al., "Involvement of Cannabinoid (Cbl)-Receptors in the Development and Maintenance of Opioid Tolerance", Neuroscience 2007; 146: 127-1288.
Teixeira-Clerc, F.,et al., "CBl cannabinoid receptor antagonism: a new strategy for the treatment of liver fibrosis", Nat Med 2006; 12: 671-676.
Maresz, K.,et al., "Direct Suppression of CNS Autoimmune Inflammation Via the Cannabinoid Receptor Cbl on Neurons and CB2 on Autoreactive T Cells", Nat Med 2007; 13: 492-497.
Berghuis ,P.,et al., "Hardwiring the Brain: Endocannabinoids Shape Neuronal Connectivity" Science 2007; 316: 1212-1216.
Kalsi ,V.,et al., "Therapy Insight: Bladder Dysfunction Associated With Multiple Sclerosis", Nat Clin Pract Urol 2005; 2: 492-501.
Wang, H., et al., "Aberrant Cannabinoid Signaling Impairs Oviductal Transport of Embryos", Nat Med 2004; 10: 1074-1080.
Kathuria, S., et al., "Modulation of Anxiety Through Blockade of Anandamide Hydrolysis", Nat Med 2003; 9: 76-81.
Guzman M: "Cannabinoids: Potential Anticancer Agents", Nature Reviews Cancer 2003; 3: 74-755.
Crowley, V.E.F., et al., "Obesity Therapy: Altering the Energy Intake And-Expenditure Balance Sheet", Nature Reviews Drug Discovery 2002; 1: 276-286.
Baker, D.,et al., "Cannabinoids Control Spasticity and Tremor in a Multiple Sclerosis Model", Nature 2000; 404: 8-87.
Steffens, S.,et al., "Low Dose Oral Cannabinoid Therapy Reduces Progression of Atherosclerosis in Mice", Nature 2005; 434:78-786.
Karsak, M., et al., "Attenuation of Allergic Contact Dermatitis Through the Endocannabinoid System", Science 2007; 316: 1494-7.
Giblin, G.M.P., et. al., "Discovery of a Selective CB 2 Receptor Agonist for the Treatment of Inflammatory Pain", Journal of Medicinal Chem. 2007, 50, 2597-2600.
Diaz, P., et. al., New Synthetic Retinoids Obtained by Palladium-Catalyzed Tandem Cyclisation-Hydride Capture Process. Tetrahedron 54(1998) 4579-4590.
Szlosek-Pinaud,M., et. al., "Palladium-Catalyzed Allylation/Carbopaliadation/Cross Coupling: A Novel Three-Component Ration for the Synthesis If 3,3-Disubstituted-2,3-Dihydrobenzfurans", Tetrahedron Letters 44 (2003) 8657-8659.
Pertwee, R.G., "Cannbinoid Receptors and Pain", Progress in Neurobiology 63 (2001) 569-611.
Chevaleyre, V., et. al., "Endocannabinoid-Mediated Synaptic Plasticity in the CNS" Ammu, Rev. Neurosci. 2006 29 37-79.
Vanecek, J., "Cellular Mechanisms of Melatonin Action", Physiological Reviews vol. 78 (3) Jul. 1998, 687-721.
Lala, Peeyush K., et al., "Role of Nitric oxide in tumor progression: Lessons from experimental tumors", Cancer and Metastasis Reviews (1998), 17(1), 91-106.
Golub, T.R., et al., "Molecular Classification of Cancer: Class Discovery and Class Predication by Gene Expression Monitoring", Science (1999), vol. 286, 531-537.
Cancer [online], [retrieved on Jul. 6, 2007]. Retrieved from the internet, URL http:/www.nlm.nih.gov/medlineplus/cancer.html>.
Cancer [online], [retrieved on Jul. 6, 2007]. Retrieved from the internet, URL http://en.wikipedia.org/wikilcancer.

* cited by examiner

HYDRAZONE MODULATORS OF CANNABINOID RECEPTORS

CROSS-REFERENCE TO RELATED APPLICATIONS

This application is a Continuation of U.S. patent application Ser. No. 12/668,867, filed Mar. 2, 2010, and claims priority to U.S. Pat. App. Ser. No. 60/949,551 filed Jul. 13, 2007 and to U.S. Pat. App. Ser. No. 61/0032,828 filed Feb. 29, 2008. These applications are incorporated by reference herein it their entirety.

FIELD OF THE INVENTION

The present invention is directed to new hydrazone compounds and compositions and their application as pharmaceuticals for the treatment of disease. Methods of modulating cannabinoid receptor activity in human or animal subject are provided for the treatment of diseases.

BACKGROUND OF THE INVENTION

CB1 and CB2 are two cannabinoid receptors that belong to the GPCR family and have very different functions and distribution. While no x-ray structure is available for these receptors, various models have been described on the basis of the x-ray structure of rhodopsin, a GPCR belonging protein responsible of the light sensitivity in vision. Matsuda L A, Lolait S J, Brownstein M J, Young A C, Bonner T I, *Structure of a Cannabinoid Receptor and Functional Expression of the Cloned cDNA*, Nature 1990, 346:561-4. CB1 is abundantly expressed in the central nervous system and is most dense in the basal ganglia, cerebellum, hippocampus, and cortex and in the peripheral nervous system, it is expressed in such sites as the testis, eye, urinary bladder, and adipocytes. CB2 is mainly expressed in the immune tissues, in cells such as those in the thymus, marrow, spleen, pancreas, and in glioma and skin tumor cells. It was recently demonstrated that CB2 receptors and their gene transcripts are widely distributed in the brain. A third cannabinoid receptor seems to be present as some chemical analogues exhibit cannabinoid biological activity without activating CB1 and CB2. Di Marzo V, Bifulco M, De Petrocellis L, *The Endocannabinoid System and Its Therapeutic Exploitation*, Nat Rev Drug Discov 2004, 3:771-84.

BRIEF SUMMARY OF THE INVENTION

Novel hydrazone compounds and pharmaceutical compositions that modulate CB1 and CB2 have been found, together with methods of synthesizing and using the compounds including methods for the treatment of cannabinoid receptor-mediated diseases in a patient by administering the compounds.

A class of hydrazone compounds, useful in treating cannobinoid receptor mediated disorders and conditions, is presented and defined by the structural Formula I:

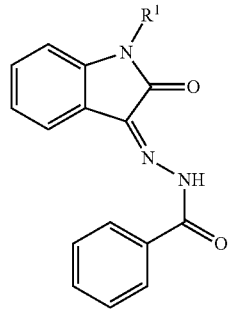

or a salt or prodrug thereof, wherein:
$R^1$ is selected from the group consisting of n-hexyl and 2-cyclohexyl ethyl,
and by the structural Formula II:

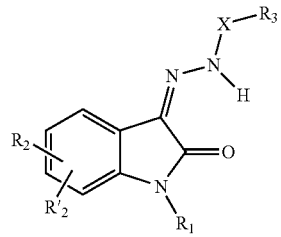

or a salt or prodrug thereof, wherein:
X is selected from the group consisting of C=O, C=S or $SO_2$;
$R^1$ is selected from the group consisting of alkyl containing from 6 to 12 carbon atoms, a polyether, a substituted benzyl and a radical defined by the following structure:

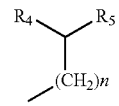

where, n is an integer ranging from 1 to 4; but if $R_2$ is an alkoxy at position 6, then $R_1$ can also be selected from the group consisting of alkyl containing from 1 to 12 carbon atoms;
$R^2$ and $R^{2'}$ vary independently and are selected from the group consisting of hydrogen, aryl, alkyl, cycloalkyl, aralkyl, alkenyl, alkynyl, halogen, an alkoxyl or a hydroxyl;
$R^3$ is selected from the group consisting of $NR^{15}R^{16}$, aryl, a heteroaryl, alkenyl, an alkynyl, an alkoxyl, a cycloalkyl containing from 5 to 10 carbon atoms and containing eventually —CO—, —O—, —S—, —SO—, —$SO_2$—, —CHOH— or —$NR^{12}$— or one of the radicals defined by the following structure:

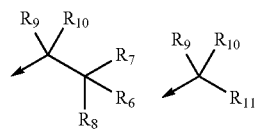

$R^4$, $R^5$ taken together form a group consisting of a radical cycloalkyl containing from 3 to 10 carbon atoms and eventually interrupted with one or more hetero atoms or by —CO—, —SO—, —$SO_2$—, —CHOH— or —$NR^{14}$—;
$R^6$ is selected from the group consisting of alkyl containing from 1 to 3 carbon atoms;
$R^7$ is selected from the group consisting of alkyl containing from 1 to 3 carbon atoms;
$R^6$ and $R^7$ taken together might form a cycloalkyl containing from 3 to 10 carbon atoms and eventually interrupted with one or more hetero atoms or by —CO—, —SO—, —$SO_2$—, —CHOH— or —$NR^{13}$—;
$R^8$ is selected from the group consisting of hydrogen, alkyl from 1 to 3 carbon atoms;

$R^9$ and $R^{10}$ vary independently and are selected from the group consisting of methyl or a hydrogen;

$R^{11}$ is selected from the group consisting of aryl, heteroaryl, or alkyl containing from 1 to 6 carbon atoms, but if $R^2$ is alkoxyl, $R^{11}$ is heterocycloalkyl;

$R^{12}$ is selected from the group consisting of hydrogen or alkyl containing from 1 to 3 carbon atoms;

$R^{13}$ is selected from the group consisting of hydrogen or alkyl containing from 1 to 3 carbon atoms;

$R^{14}$ represents an alkyl containing from 1 to 3 carbon atoms; and $R^{15}$ and $R^{16}$ vary independently and are selected from the group consisting of an alkyl containing 1 to 6 carbon atoms or taken together might form a group consisting of a radical cycloalkyl containing from 3 to 10 carbon atoms that are eventually interrupted with one or more hetero atoms or by —CO—, —SO—, —SO$_2$—, —CHOH— or —NR$^{14}$—.

Hydrazone compounds presented herein possess useful cannabinoid receptor modulating activity, and may be used in the treatment or prophylaxis of a disease or condition in which a cannabinoid receptor plays an active role. Thus, in broad aspect, pharmaceutical compositions are provided comprising one or more the compounds together with a pharmaceutically acceptable carrier, as well as methods of making and using the compounds and compositions.

Methods for modulating cannabinoid receptors with hydrazone compounds are also provided. Methods for treating a cannabinoid receptor-mediated disorder such as neuropathic pain or addiction in a patient in need of such treatment comprising administering to said patient a therapeutically effective amount of a hydrazone compound or composition presented herein. The use of compounds disclosed herein can be used in the manufacture of a medicament for the treatment of a disease or condition ameliorated by the modulation of cannabinoid receptors.

BRIEF DESCRIPTION OF THE DRAWINGS

The foregoing summary as well as the following detailed description of the preferred embodiment of the invention will be better understood when read in conjunction with the appended drawings. It should be understood, however, that the invention is not limited to the precise arrangements and instrumentalities shown herein.

For a more complete understanding of the present invention, and the advantages thereof, reference is now made to the following descriptions taken in conjunction with the accompanying drawings, in which:

FIG. 12A more specifically shows an area under the curve (AUC) of the effects of 5.0, 10, and 15 mg/kg of compound of Example 6. FIG. 12B more specifically shows the dose response curve of the anti-allodynic effects of compound of Example 6 in a spinal nerve ligation neuropathic pain model was calculated as described by Tallarida and Murray. Tallarida, R. J., *Manual of Pharmacologic Calculations with Computer Programs*, Second ed.; Springer-Verlag: New York, 1987. The calculated $ED_{50}$ was 5.9 (95% CI 4.5-7.9) mg/kg, i.p. and the calculated $ED_{90}$ was 12 (95% CI 9.6-15.5) mg/kg, i.p. Pretreatment with 5 mg/kg i.p. of a selective CB2 antagonist AM630 antagonized the effects of compound of Example 6. Data are expressed as mean±s.e. mean. *P<0.01 versus all other groups (one-way ANOVA followed by Tukey-Kramer post hoc analysis for multiple group comparison). The AUC was calculated using the trapezoidal rule.

DETAILED DESCRIPTION OF THE INVENTION

Figure 1A:
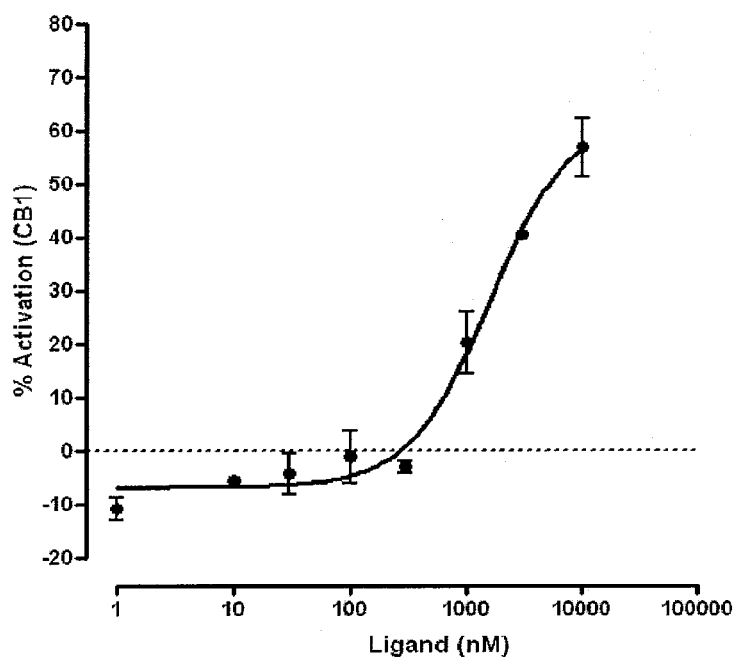
FIGS. 1A and 1B show functional activity data for compound of Example 5.
Figure 1B:
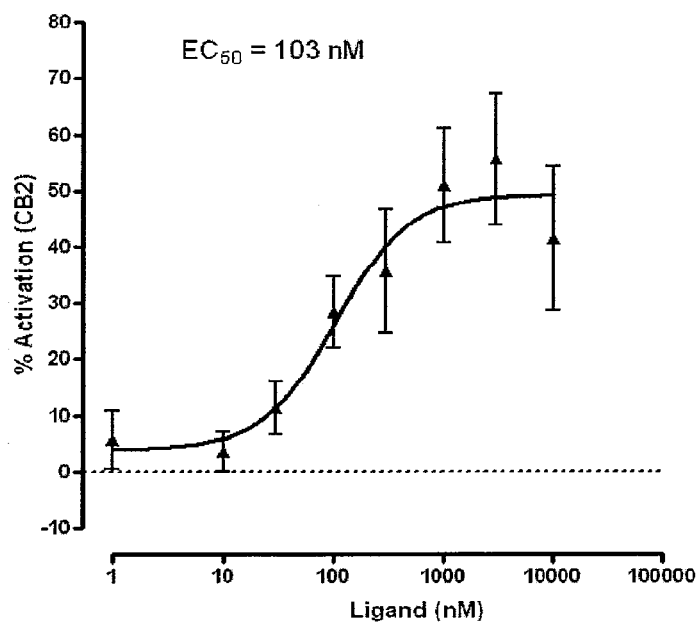
Figure 2A:
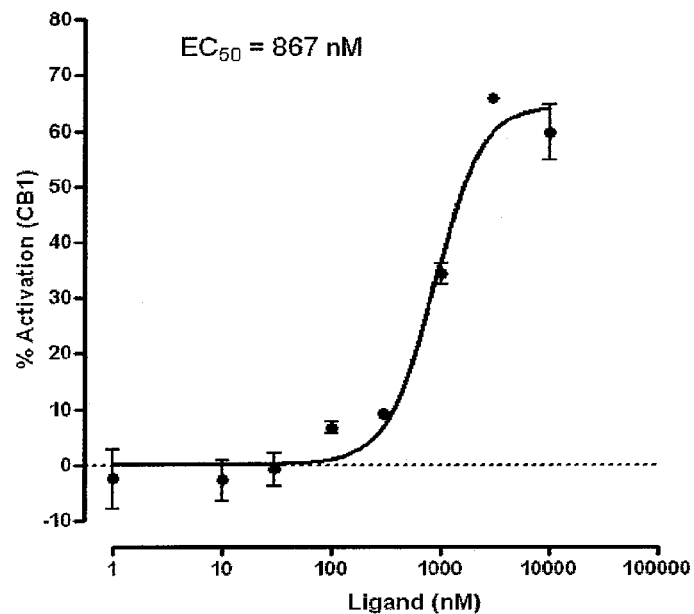
FIGS. 2A and 2B show functional activity data for compound of Example 6.
Figure 2B:
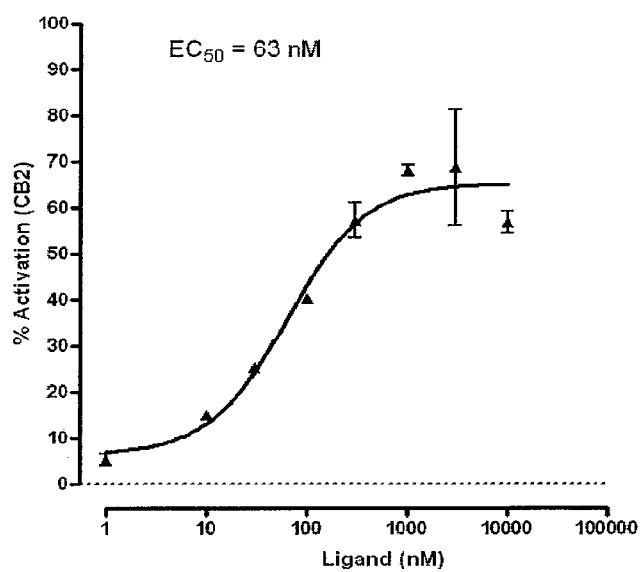
Figure 3A:
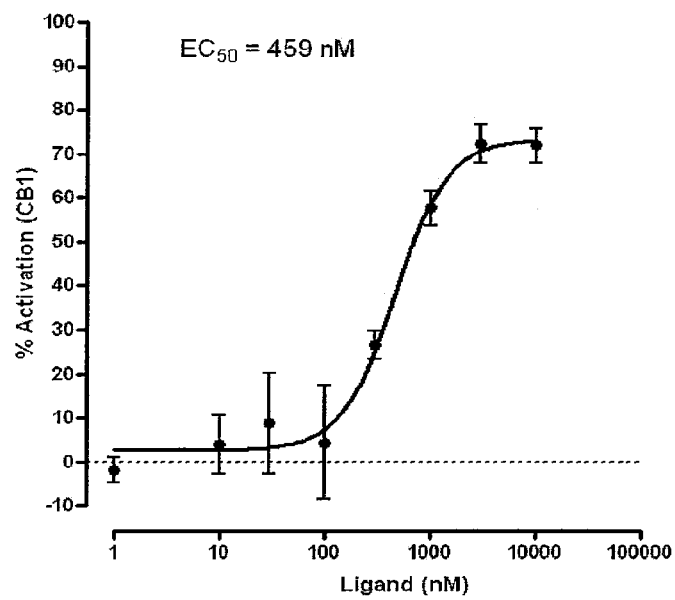
FIGS. 3A and 3B show functional activity data for compound of Example 20.
Figure 3B:
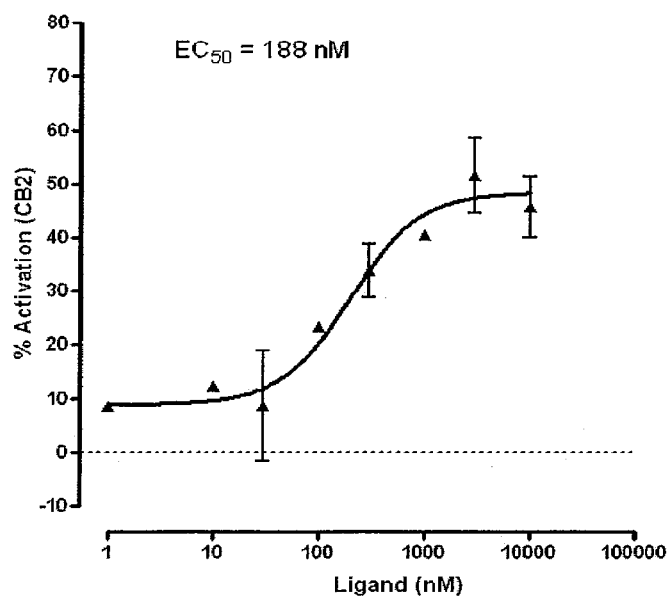

Novel compounds presented include compounds of the structural Formula III

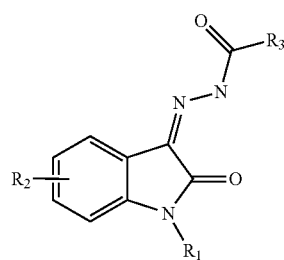

or a salt or prodrug thereof, wherein:

$R^1$ is selected from the group consisting of n-hexyl and 2-cyclohexyl ethyl;

$R^2$ is selected from the group consisting of a hydrogen atom or a methoxy;

$R^3$ is selected from the group consisting of $NR^4R^5$, aryl, heteroaryl, alkenyl, an alkynyl, an alkoxyl, a cycloalkyl containing from 5 to 10 carbon atoms and containing eventually —CO—, —O—, —S—, —SO—, —$SO_2$—, —CHOH— or —$NR^{12}$—, or one of the radicals defined by the following structure:

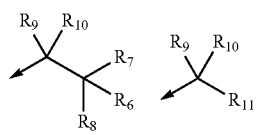

$R^4$, $R^5$ taken together form a group consisting of a radical cycloalkyl containing from 3 to 10 carbon atoms and eventually interrupted with one or more hetero atoms or by —CO—, —SO—, —$SO_2$—, —CHOH— or —$NR^{14}$—;

$R^6$ is selected from the group consisting of alkyl containing from 1 to 3 carbon atoms;

$R^7$ is selected from the group consisting of alkyl containing from 1 to 3 carbon atoms;

$R^6$ and $R^7$ taken together might form a cycloalkyl containing from 3 to 10 carbon atoms and eventually interrupted with one or more hetero atoms or by —CO—, —SO—, —$SO_2$—, —CHOH— or —$NR^{13}$—;

$R^8$ is selected from the group consisting of hydrogen and alkyl from 1 to 3 carbon atoms;

$R^9$ and $R^{10}$ vary independently and are selected from the group consisting of methyl or a hydrogen;

$R^{11}$ is selected from the group consisting of aryl, heteroaryl or alkyl containing from 1 to 6 carbon atoms;

$R^{12}$ is selected from the group consisting of hydrogen or alkyl containing from 1 to 3 carbon atoms;

$R^{13}$ is selected from the group consisting of hydrogen or alkyl containing from 1 to 3 carbon atoms; and $R^{14}$ represents an alkyl containing from 1 to 3 carbon atoms.

As used herein, the terms below have the meanings indicated.

The term "acyl," as used herein, alone or in combination, refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(O)$CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20, preferably 2 to 6, carbon atoms. Alkenylene refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—$NR_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino ($CH_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

According to the present invention, the expression alkyl radicals understood to mean a linear optionally branched and optionally fluorinated radical. In certain embodiments, alkyl radicals having from 6 to 12 carbon atoms are 2-Methyl-pentan-2-yl, 3,3-Dimethyl-butan-1-yl, hexyl, heptyl, octyl, nonyl, decyl, dodecyl. "Alkyl radicals" containing from 1 to 3 carbon atoms, are linear or branched radicals containing, respectively, from 1 to 3. Preferably, the alkyl radicals containing from 1 to 3 carbon atoms are methyl, ethyl, n-propyl, or 2-propyl radicals. The expression "alkoxyl radical" is understood to mean a radical containing from 1 to 3 carbon atoms, such as methoxyl, ethoxyl, propyloxyl or isopropyloxyl radicals.

The term "aryl radical" means a phenyl or a naphthyl radical, eventually mono- or disubstituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The term "heteroaryl" means an aryl radical interrupted with one or more hetero atoms, such as a thiophenyl, thiazolyl or imidazolyl radical, optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 6 carbon atoms.

The term "polyether radical" means a polyether radical containing from 2 to 6 carbon atoms interrupted with at least one oxygen atom, such as methoxymethyl, ethoxymethyl or methoxyethoxymethyl radicals or methoxyethyl.

The term "halogen atom" includes, but is not limited to, fluorine, chlorine or bromine atom.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O) O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronapthalene, octahydronapthalene as well as the multicyclic (multicentered) saturated or partially unsaturated type. The latter type of isomer is exemplified in general by, bicyclo[1,1,1]-pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocyclyl," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocyclyl, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two kinds of optical isomers. The first optical isomer are compounds that are mirror images of one another but cannot be superimposed on each other. These isomers are called "enantiomers". The second optical isomers are molecules that are not mirror images but each molecule rotates plane polarized light and are considered optically active. Such molecules are called "diastereoisomers". Diasteroisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"Cannabinoid receptor modulator" is used herein to refer to a compound that exhibits an $EC_{50}$ or $IC_{50}$ with respect to a cannabinoid receptor activity of no more than about 50 μM and more typically not more than about 10 μM, as measured in the cannabinoid receptor assay described generally herein below. "$EC_{50}$" is that concentration of modulator which activates the activity of a cannabinoid receptor to half-maximal level. "$IC_{50}$" is that concentration of modulator which reduces the activity of a cannabinoid receptor to half-maximal level. This test will be done during the exemplification period.

The term "modulator" described herein reflects any chemical compound that will act as full agonist, partial agonist, inverse agonist or as an antagonist at any known or yet to be discovered/identified cannabinoid receptor.

Compounds described herein have been discovered to exhibit modulatory activity against cannabinoid receptors and exhibit an $EC_{50}$ of $IC_{50}$ with respect to a cannabinoid receptor of no more than about 10 µM, more preferably, no more than about 5 µM, even more preferably not more than about 1 µM, and most preferably, not more than about 200 nM, as measured in the assays described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds of the present invention may also exist as prodrugs, as described in *Hydrolysis in Drug and Prodrug Metabolism: Chemistry, Biochemistry, and Enzymology*, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds of the present invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich, *Pharmaceutical Salts: Properties, Selection, and Use*, Wiley-VCHA, Zurich, Switzerland, 2002.

The term "therapeutically acceptable salt," as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described in this patent could be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic nontoxic bases include salts of primary, secondary, and tertiary amines, substituted amines including naturally occurring substituted amines, cyclic amines, and basic ion exchange resins, such as argmine, betaine, caffeine, choline, ethylamine, 2-diethylaminoethano, 1,2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the novel compounds described in this patent are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds of the subject invention to be administered as the raw chemical, it is also possible to present them as a pharmaceutical formulation. Accordingly, the subject invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

One example of a formulation appropriate for administration through an oral route comprises 0.60 g of the compound described in Example 6 below, 10.00 g of NMP, 64.40 g of LABRAFIL® M1944 CS, and 25.00 g of LABRASOL®.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

One example of a formulation appropriate for administration through a parenteral route comprises 1.00 g of the compound described in Example 36 below, 30.00 g of NMP, 30.00 g of propylene glycol, 10.00 g of CREMOPHOR® ELP, 10.00 g of EtOH 95%, and 19.00 g of saline solution.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Compounds of the present invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include solid, liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Via the topical route, the pharmaceutical composition according to the invention may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion. The compounds are used topically at a concentration generally of between 0.001% and 10% by weight and preferably between 0.01% and 1% by weight, relative to the total weight of the composition.

One example of a formulation appropriate for administration through a topical route comprises 3.00 g of the compound described in Example 36 below, 35.00 g of NMP, 25.00 g of LABRASOL®, 15.00 g of oleic acid, 12.00 g of COMPRITOL® 888 ATO, and 10.00 g of EtOH.

The compounds presented herein may also find an application in cosmetics, in particular in body and hair hygiene and more particularly for regulating and/or restoring skin lipid metabolism.

Cosmetic use of a composition comprising, in a physiologically acceptable support, at least one of the compounds described herein for body or hair hygiene are presented. The cosmetic composition, in a cosmetically acceptable support, at least one compound and/or an optical or geometrical isomer thereof or a salt thereof, and may be in the form of liquid or semi liquid such as ointments, creams or in the form of solid such as powders. It may also be in the form of suspensions such as polymeric microspheres or polymer patches and hydrogels allowing a controlled release. This topical composition may be in anhydrous form, in aqueous form or in the form of an emulsion. The concentration of compound in the cosmetic composition is between 0.001% and 5% by weight relative to the total weight of the composition. Finally, a subject of the present invention is a cosmetic process for enhancing the skin, which consists in applying to the skin a composition comprising at least one compound presented herein.

For administration by inhalation, the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

Certain compounds according to the invention can be administered at a daily dose of about 0.001 mg/kg to 100 mg/kg of body weight, in 1 to 3 dosage intakes. Further, certain compounds can be used systemically, at a concentration generally of between 0.001% and 10% by weight and preferably between 0.01% and 1% by weight, relative to the weight of the composition.

The amount of active ingredient that may be combined with the carrier materials to produce a single dosage form will vary depending upon the host treated and the particular mode of administration.

The compounds of the subject invention can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the hydrazone compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an antihypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention together with inert or active compounds, or other drugs including wetting agents, flavour enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or anti-acne agents, such as S-carboxymethylcysteine, S-benzylcysteamine, salts thereof or derivatives thereof, or benzoyl peroxide, antibiotics, for instance erythromycin and tetracyclines, chemotherapeutic agent, for instance Paclitaxel, antifungal agents such as ketoconazole, agents for promoting regrowth of the hair, for instance Minoxidil (2,4-diamino-6-piperidinopyrimidine 3-oxide), non-steroidal anti-inflammatory agents, carotenoids, and especially p-carotene, antipsoriatic agents such as anthralin and its derivatives, eicosa-5,8,11,14-tetraynoic acid and eicosa-5,8,11-triynoic acid, and esters and amides thereof, retinoids, i.e. RAR or RXR receptor ligands, which may be natural or synthetic, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenyloin and the like and mixtures or pharmaceutically acceptable salts thereof. Needless to say, a person skilled in the art will take care to select the other compound(s) to be added to these compositions such that the advantageous properties intrinsically associated with the hydrazone compound are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating cannabinoid receptor-mediated disorders in a human or animal subject in need of such treatment are presented herein, the methods comprising the step of administering to a subject in need thereof an amount of a hydrazone compound effective to reduce or prevent a disorder in combination with at least one additional agent for the treatment of said disorder that is known in the art.

In a related aspect, therapeutic compositions having at least one novel hydrazone compound described herein can be administered in combination with one or more additional agents for the treatment of cannabinoid-mediated disorders.

Furthermore, methods of treatment of certain diseases and indications in a human or animal subject in need of such treatment are provided herein. Hydrazone compounds described herein can be used alone or in combination with other agents and compounds in the treatment of neuropathic pain, addiction (including nicotine, cocaine, opioids, hashish, marijuana, alcohol dependence, food), cancer (including melanoma, lymphomas, and gliomas), inflammation including autoimmune inflammation, cardiovascular disease, liver fibrosis, obesity, osteoporosis and other bone disease. Additional indications for use of the compounds disclosed herein include acne, psoriasis, allergic contact dermatitis, anxiety, spasticity and tremor, bladder dysfunctions, prevention of miscarriage and ectopic pregnancy, Tourette's, Parkinson's disease, stroke, glaucoma and other diseases of the eye including intraocular pressure, diarrhea and nausea. Each such treatment described above includes the step of administering to a subject in need thereof a therapeutic effective amount of the hydrazone compound described herein to reduce or prevent such disease or indication.

Besides being useful for human treatment, the compounds and formulations of the present invention are also useful for veterinary treatment of companion animals, exotic animals and farm animals, including mammals, rodents, and the like. More preferred animals include horses, dogs, and cats. These hydrazone compounds are also helpful in neuronal growth and development.

Therefore, the compounds described herein may be used alone or in combination with another agent or compound in methods for treating, ameliorating or preventing a syndrome, disorder or disease in which cannabinoid receptor is involved, including, but not limited to, ocular complaint such as glaucoma, pain, controlling appetite, regulating metabolism, diabetes, social and mood disorders, seizure-related disorders, substance abuse disorders, learning, cognition and/or memory disorders, bowel disorders, gastrointestinal disorders, respiratory disorders, locomotor activity disorders, movement disorders, immune disorders or inflammation disorders, and controlling organ contraction and muscle spasm.

The compounds presented herein may be also useful in enhancing learning, cognition and/or memory, regulating cell growth, providing neuroprotection and the like. The compounds presented herein may also be used for treating dermatological complaints associated with a keratinization disorder relating to cell differentiation and proliferation, especially for treating acne, for treating other dermatological complaints, with or without cell proliferation disorder, and especially all forms of psoriasis, for treating all dermal or epidermal proliferations, for preventing or treating cicatrization disorders, in the treatment of dermatological or general complaints with an immunological component, in the treatment of skin disorders caused by exposure to UV radiation, and also for combating sebaceous function disorders, for repairing or combating aging of the skin, for preventing or treating cicatrization disorders, or in the treatment of pigmentation disorders.

Historically, cannabinoid preparations have been used for medicinal and recreational purposes for many centuries. Cannabinoids are present in the hemp Cannabis sativa L. Identification of the main active ingredient, tetrahydrocannabinol (Δ 9-THC) has been done in 1964. Gaoni Y, Mechoulam R, *Isolation, Structure, and Partial Synthesis of an Active Constituent of Hashish*, J Am Chem Soc 1964, 86:1646-7. The endocannabinoid system was elucidated in the early 1990's. Currently, two receptors belonging to the GPCR family CB1 and CB2, five endogenous lipid ligands and the enzymes involved in their syntheses and metabolism have been identified. Matsuda L A, Lolait S J, Brownstein M J, Young A C, Bonner T I, *Structure Of A Cannabinoid Receptor And Functional Expression Of The Cloned Cdna*, Nature 1990, 346:561-4.

Neuropathic pain is caused by a lesion in the central (brain and spinal cord) or peripheral nervous system. It is not a single disease entity and may result from a wide range of heterogeneous conditions that differ in etiology. It is triggered by conditions such as diabetic neuropathy, AIDS-related neuropathy, post-herpetic neuralgia, degenerative spinal disease, chemotherapy, radiotherapy, sympathetic dystrophies, post-amputation stump (phantom limb pain), trigeminal neuralgia, and multiple sclerosis (MS). Allodynia (touch-evoked pain) and hyperalgesia are clinically perplexing characteristics of neuropathic pain.

The prevalence of neuropathic pain is estimated to be about 8% in the general population worldwide. Torrance, N., et al., *The Epidemiology of Chronic Pain of Predominantly Neuropathic Origin. Results From a General Population Survey*, The Journal of Pain, 2006, 7:281-289. In the US, the annual healthcare cost attributable to neuropathic pain is almost $40 billion. Turk, D. C., *Clinical Effectiveness and Cost-Effectiveness of Treatments for Patients with Chronic Pain*, Clin J Pain, 2002, 18:355-65. Currently, there is no effective or satisfactory treatment for neuropathic pain. Warms, C. A. et al., *Treatments for Chronic Pain Associated with Spinal Cord Injuries: Many are Tried, Few are Helpful*, Clin J Pain, 2002, 18:154-63.

Two cannabinoid (CB) receptors (CB1 and CB2) have been characterized and cloned. Matsuda, L. A., et al. *Structure of a Cannabinoid Receptor and Functional Expression of the Cloned DNA*, Nature, 1990, 346:561-4; Munro, S., et al., *Molecular Characterization of a Peripheral Receptor for Cannabinoids*, Nature, 1993, 365:61-5. The CB1 receptor is found predominantly in the brain, with highest densities in the hippocampus, cerebellum, and striatum. Ameri, A., *The Effects of Cannabinoids on the Brain*, Progress in Neurobiology, 1999, 58:315-348 Impairment of cognitive functions induced by $\Delta^9$-THC is mediated by CB1 receptors in the hippocampus. Herkenham, M., et al., *Cannabinoid Receptor Localization in Brain*, Proceedings of the National Academy of Sciences, 1990, 87:1932-1936. Despite promising effects of CB1 agonists on pain relief, CNS side effects such as catalepsy or motor impairment have compromised their pharmaceutical development.

CB2 receptors are expressed mainly on immune tissues: the spleen, tonsils, monocytes, and B and T lymphocytes, although it was recently demonstrated that CB2 receptors and their gene transcripts are widely distributed in the CNS. Munro, S., et al., *Molecular Characterization of a Peripheral Receptor for Cannabinoids*, Nature, 1993, 365:61-5; Facci L., et al., *Mast Cells Express a Peripheral Cannabinoid Receptor With Differential Sensitivity to Anandamide and Palmitoylethanolamide*, Proc Natl. Acad. Sci. USA 1995, 92:3376-80. The expression of CB2 in the brain suggests that CB2 receptors may play broader roles in the CNS than previously anticipated. Onaivi, E. S., et al., *Discovery of the Presence and Functional Expression of Cannabinoid CB2 Receptors in Brain*, Ann NY Acad Sci 2006, 1074:514-536.

CB1 is abundantly expressed in the central nervous system with highest density level in the basal ganglia, cerebellum, hippocampus and cortex as well as in the peripheral nervous system such as testis, eye, urinary bladder and adipocyte. CB2 is mainly expressed in the immune tissues and cells such as the thymus, marrow, spleen, pancreas and in glioma and skin tumor cells.

CB2 receptors and their gene transcripts have been recently demonstrated as widely distributed in the brain. The multifocal expression of CB2 immunoreactivity in brain suggests that CB2 receptors play a role in the brain and may be involved in depression and substance abuse. See e.g., Onaivi E S, Ishiguro H, Gong J-P, Patel S, Perchuk A, Meozzi P A, Myers L, Mora Z, Tagliaferro P, Gardner E, Brusco A, Akinshola B E, Liu Q-R, Hope B, Iwasaki S, Arinami T, Teasenfitz L, Uhl G R, *Discovery of the Presence and Functional Expression of Cannabinoid CB2 Receptors in Brain*, Ann NY Acad Sci 2006, 1074:514-536; Berghuis P, Rajnicek A M, Morozov Y M, Ross R A, Mulder J, Urban G M, Monory K, Marsicano G, Matteoli M, Canty A, Irving A J, Katona I, Yanagawa Y, Rakic P, Lutz B, Mackie K, Harkany T, *Hardwiring the Brain: Endocannabinoids Shape Neuronal Connectivity*, Science 2007, 316:1212-1216; Kalsi V, Fowler C J, *Therapy Insight: Bladder Dysfunction Associated With Multiple Sclerosis*, Nat Clin Pract Urol 2005, 2:492-501; Kathuria S, Gaetani S, Fegley D, Valino F, Duranti A, Tontini A, Mor M, Tarzia G, Rana G L, Calignano A, Giustino A, Tattoli M, Palmery M, Cuomo V, Piomelli D, *Modulation of Anxiety Through Blockade of Anandamide Hydrolysis*, Nat Med 2003, 9: 76-81; Baker D, Pryce G, Croxford J L, Brown P, Pertwee R G, Huffman J W, Layward L, *Cannabinoids Control Spasticity and Tremor in a Multiple Sclerosis Model*, Nature 2000, 404:84-87. Furthermore, the endocannabinoid system has been implicated in allergic contact dermatitis. Karsak M, Gaffal E, Date R, Wang-Eckhardt L, Rehnelt J, Petrosino S, Starowicz K, Steuder R, Schlicker E, Cravatt B, Mechoulam R, Buettner R, Werner S, Di Marzo V, Tuting T, Zimmer A, *Attenuation of Allergic Contact Dermatitis Through the Endocannabinoid System*, Science 2007, 316:1494-7.

In addition, studies provide support for the role of cannabinoid system in several physiological functions including food consumption and body weight, in which CB1 receptor activation leads to increased food consumption and weight gain. Fride, E., *Endocannabinoids in the Central Nervous System—an Overview*, Prostaglandins Leukot Essent Fatty Acids 2002, 66:221-33. Subsequently, CB1 receptor blockade reduces food consumption and leads to weight loss. Van Gaal L F, Rissanen A M, Scheen A J, Ziegler O, Rossner S, *Effects Of The Cannabinoid-1 Receptor Blocker Rimonabant On Weight Reduction And Cardiovascular Risk Factors In Overweight Patients: 1-Year Experience From The RIO-Europe Study*, The Lancet 2005, 365:1389-1397.

Modulators of CB1/CB2 receptors have been used in different clinical or preclinical studies. Steffens S, Veillard N R, Arnaud C, Pelli G, Burger F, Staub C, Zimmer A, Frossard J-L, Mach F, *Low Dose Oral Cannabinoid Therapy Reduces Progression of Atherosclerosis in Mice*, Nature 2005, 434:782-786. For example, CB1 agonists have been used for treatment of nausea, Tourette's, Parkinson's disease, glaucoma, cancer, diarrhea, and stroke. Guzman M, *Cannab-* inoids: Potential Anticancer Agents, Nature Reviews Cancer 2003, 3:745-755. Further, CB2 agonists have been used for treatment pain, gliomas, lymphomas, and inflammation. Maresz K, Pryce G, Ponomarev E D, Marsicano G, Croxford J L, Shriver L P, Ledent C, Cheng X, Carrier E J, Mann M K, Giovannoni G, Pertwee R G, Yamamura T, Buckley N E, Hillard C J, Lutz B, Baker D, Dittel B N, *Direct Suppression of CNS Autoimmune Inflammation Via the Cannabinoid Receptor CB1 on Neurons and CB2 on Autoreactive T Cells*, Nat Med 2007, 13: 492-497.

Unlike CB1 agonists, CB2 ligands are devoid of psychoactivity. Up-regulation of CB2-receptor mRNA and proteins in the dorsal root ganglia (DRG) and spinal cord is also found in animals after spinal nerve ligation, sciatic nerve injury, or saphenous nerve ligation. Beltramo, M., et al., *CB2 Receptor-Mediated Antihyperalgesia: Possible Direct Involvement of Neural Mechanisms*, Eur J Neurosci, 2006, 23:1530-8; Wotherspoon, G., et al., *Rat Sensory Neurons*, Neuroscience, 2005, 135:235-45; Zhang, J.; Hoffert, et al., *Induction of CB2 Receptor Expression in the Rat Spinal Cord of Neuropathic but not Inflammatory Chronic Pain Models*, Eur J Neurosci, 2003, 17:2750-4; Walczak, J. S., et al., *Behavioral, Pharmacological and Molecular Characterization of the Saphenous Nerve Partial Ligation: a New Model of Neuropathic Pain*, Neuroscience, 2005, 132:1093-102; Walczak, J. S., et al., *Characterization of Chronic Constriction of the Saphenous Nerve, a Model of Neuropathic Pain in Mice Showing Rapid Molecular and Electrophysiological Changes*, J Neurosci Res, 2006, 83:1310-22.

Figure 7:
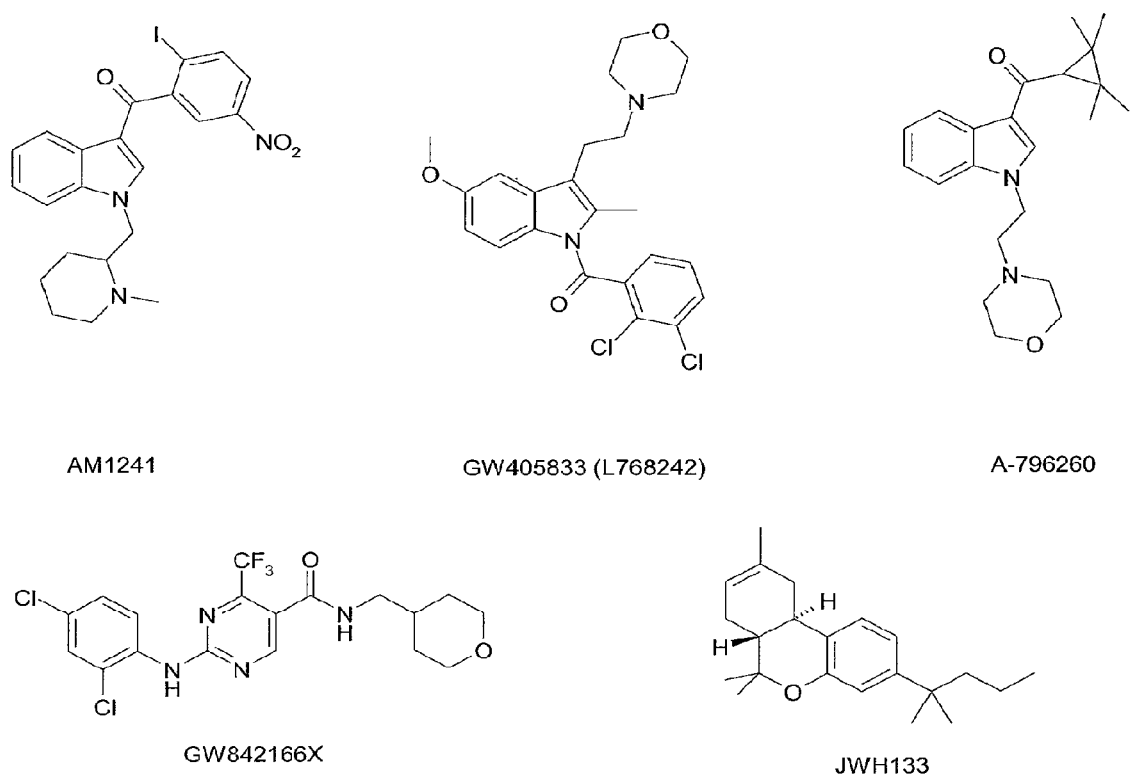
FIG. 7 shows chemical structures of cannabinoid CB2-selective agonists.

Several CB2 selective ligands have been described in literature. Page, D., et al., *New 1,2,3,4-Tetrahydropyrrolo[3,4-b]indole Derivatives as Selective CB2 Receptor Agonists*, Bioorganic & Medicinal Chemistry Letters, 2007, 17:6183-6187; Giblin, G. M. P., et al., *Discovery of 2-[(2,4-Dichlorophenyl)amino]-N-[(Tetrahydro-2H-Pyran-4-yl)Methyl]-4-(Trifluoromethyl)-5-Pyrimidinecarboxamide, a Selective CB2 Receptor Agonist for the Treatment of Inflammatory Pain*, J. Med. Chem. 2007, 50:2597-2600; Huffman, J. W., *CB2 Receptor Ligands*, Mini Reviews in Medicinal Chemistry, 2005, 5:641-649; Valenzano, K. J., et al., *Pharmacological and Pharmacokinetic Characterization of the Cannabinoid Receptor 2 Agonist, GW405833, Utilizing Rodent Models of Acute and Chronic Pain, Anxiety, Ataxia and Catalepsy*, Neuropharmacology, 2005, 48:658-72; Huffman, J. W., et al., *Synthesis and Pharmacology of a Very Potent Cannabinoid Lacking a Phenolic Hydroxyl with High Affinity for the CB2 Receptor*, J. Med. Chem., 1996, 39:3875-3877; Murineddu, G., et al., *Tricyclic Pyrazoles. 4. Synthesis and Biological Evaluation of Analogues of the Robust and Selective CB2 Cannabinoid Ligand 1-(2',4'-Dichlorophenyl)-6-methyl-N-piperidin-1-yl-1,4-dihydroindeno[1,2-c]pyrazole-3-carboxamide*, J. Med. Chem., 2006, 49:7502-7512; Manera, C., et al., *Design, Synthesis, and Biological Evaluation of New 1,8-Naphthyridin-4(1H)-on-3-carboxamide and Quinolin-4(1H)-on-3-carboxamide Derivatives as CB2 Selective Agonists*, J. Med. Chem., 2006, 49:5947-5957; Salo, O. M. H., et al., *Virtual Screening of Novel CB2 Ligands Using a Comparative Model of the Human Cannabinoid CB2 Receptor*, J. Med. Chem., 2005, 48:7166-7171; Ohta, H., et al., *Sulfonamide Derivatives as New Potent and Selective CB2 Cannabinoid Receptor Agonists*, Bioorganic & Medicinal Chemistry Letters, 2007, 17:5133-5135; Ohta, H., et al., *N-Alkylidenearylcarboxamides as New Potent and Selective CB2 Cannabinoid Receptor Agonists with Good Oral Bioavailability*. Bioorganic & Medicinal Chemistry Letters, 2007, 17:6299-6304; Yao, B. B., et al., *In Vitro and In Vivo Characterization of A-796260: A Selective Cannabinoid CB2 Receptor Agonist Exhibiting Analgesic Activity in Rodent Pain Models*. Br J Pharmacol, 2008, 153:390-401. However, some of the compounds described as CB2 agonists failed to exhibit potent agonist efficacy, or have not been fully characterized in functional assays. Functional studies for various CB2-selective agonists have been described recently. Yao, B. B., et al., *In Vitro and In Vivo Characterization of A-796260: A Selective Cannabinoid CB2 Receptor Agonist Exhibiting Analgesic Activity in Rodent Pain Models*. Br J Pharmacol, 2008, 153:390-401. CB2 functional activities of GW405833 (identical to the CB2 agonist referred to as L768242) and AM1241 (FIG. 7) are condition-dependent and they are described as protean agonists. Therefore, understanding the mechanisms of AM1241 in pain relief is complex. Beltramo, M., et al., *CB2 Receptor-Mediated Antihyperalgesia: Possible Direct Involvement of Neural Mechanisms*, Eur J Neurosci, 2006, 23:1530-8; Ibrahim, M., et al., *CB2 Cannabinoid Receptor Mediation of Antinociception*, Pain, 2006, 122:36-42; Ibrahim, M. M., et al., *Activation of CB2 Cannabinoid Receptors by AM1241 Inhibits Experimental Neuropathic Pain: Pain Inhibition by Receptors Not Present in the CNS*, PNAS, 2003, 100:10529-10533. Furthermore AM1241 showed interactions with the opioid system. Ibrahim, M. M., et al., *CB2 Cannabinoid Receptor Activation Produces Antinociception by Stimulating Peripheral Release of Endogenous Opioids*, PNAS 2005, 102:3093-3098. A recent publication disclosed that a CB2 selective agonist, GW842166X, was chosen as clinical candidate for the treatment of inflammatory pain. Giblin, G. M. P., et al., *Discovery of 2-[(2,4-Dichlorophenyl)amino]-N-[(Tetrahydro-2H-Pyran-4-yl)Methyl]-4-(Trifluoromethyl)-5-Pyrimidinecarboxamide, a Selective CB2 Receptor Agonist for the Treatment of Inflammatory Pain*, J. Med. Chem. 2007, 50:2597-2600. JWH-133, a well characterized CB2 agonist, structurally based upon $\Delta^9$-tetrahydrocannabinol, inhibited neuropathic hyperalgesia through a CB2-selective mechanism. Huffman, J. W., et al., *3-(1',1'-Dimethylbutyl)-1-deoxy-delta8-THC and Related Compounds: Synthesis of Selective Ligands for the CB2 Receptor*, Bioorg Med Chem., 1999, 7:2905-14; Sagar, D. R., et al., *Inhibitory effects of CB1 and CB2 Receptor Agonists on Responses of DRG Neurons and Dorsal Horn Neurons in Neuropathic Rats*, European Journal of Neuroscience, 2005, 22:371-379. A-796260, another well characterised selective CB2 agonist showed efficacy in models of inflammatory, post-operative, neuropathic and osteoarthritic pain. Yao, B. B., et al., *In Vitro and In Vivo Characterization of A-796260: A Selective Cannabinoid CB2 Receptor Agonist Exhibiting Analgesic Activity in Rodent Pain Models*. Br J Pharmacol, 2008, 153:390-401. These activities were selectively blocked by CB2, but not CB1 or µ-opioid receptor-selective antagonists. Recently a non selective CB1/CB2 dual agonist with limited brain penetration has been shown to reverse neuropathic mechanical hyperalgesia in rat model of neuropathic pain. Dziadulewicz, E. K., et al., *Naphthalen-1-yl-(4-Pentyloxynaphthalen-1-yl)methanone: A Potent, Orally Bioavailable Human CB1/CB2 Dual Agonist with Antihyperalgesic Properties and Restricted Central Nervous System Penetration*, J. Med. Chem., 2007.

Moreover, CB1 antagonists have been used for treatment obesity and addiction. Crowley V E F, Yeo G S H, O'Rahilly S, *Obesity Therapy: Altering the Energy Intake-and-Expenditure Balance Sheet*, Nature Reviews Drug Discovery 2002, 1:276-286; Trang T, Sutak M, Jhamandas K, *Involvement of Cannabinoid (CB1)-Receptors in the Development and Maintenance of Opioid Tolerance*, Neuroscience 2007, 146: 1275-1288; Teixeira-Clerc F, Julien B, Grenard P, Van Nhieu J T, Deveaux V, Li L, Serriere-Lanneau V, Ledent C, Mallat A, Lotersztajn S, *CB1 Cannabinoid Receptor Antagonism: A New Strategy For the Treatment of Liver Fibrosis*, Nat Med 2006, 12:671-676. For example, the CB1 antagonist SR141716A reduces food intake in mice. Di Marzo V, Goparaju S K, Wang L, Liu J, Batkai S, Jarai Z, Fezza F, Miura G I, Palmiter R D, Sugiura T, Kunos G, *Leptin-Regulated Endocannabinoids Are Involved In Maintaining Food Intake*, Nature 2001, 410:822-5. Also, CB1 cannabinoid antagonists have been cited to treat drug addiction. Maldonado R, Valverde O, Berrendero F, *Involvement Of The Endocannabinoid System In Drug Addiction*, Trends Neurosci 2006, 29:225-32. Cannabinoids attenuate deep tissue hyperalgesia produced by both cancer and inflammatory conditions. Kehl L J, Hamamoto D T, Wacnik P W, Croft D L, Norsted B D, Wilcox G L, Simone D A, *A Cannabinoid Agonist Differentially Attenuates Deep Tissue Hyperalgesia In Animal Models Of Cancer And Inflammatory Muscle Pain*, Pain 2003, 103:175-86. Cannabinoids also have a good potential for the treatment osteoporosis and other bone diseases. Idris A I, van't H of R J, Greig I R, Ridge S A, Baker D, Ross R A, Ralston S H, *Regulation Of Bone Mass, Bone Loss And Osteoclast Activity By Cannabinoid Receptors*, Nat Med 2005, 11:774-9. Cannabinoids are able to reduce intraocular pressure. CB1 has also been shown to be involved in ectopic pregnancy in mice. Wang H, Guo Y, Wang D, Kingsley P J, Marnett L J, Das S K, DuBois R N, Dey S K, *Aberrant Cannabinoid Signaling Impairs Oviductal Transport of Embryos*, Nat Med 2004, 10:1074-1080.

Certain published data demonstrate that human keratinocytes partake in the peripheral endocannabinoid system. CB1 receptors have been implicated in epidermal differentiation and skin development. Maccarrone M, Di Rienzo M, Battista N, Gasperi V, Guerrieri P, Rossi A, Finazzi-Agro A, *The Endocannabinoid System In Human Keratinocytes. Evidence That Anandamide Inhibits Epidermal Differentiation Through CB1 Receptor-Dependent Inhibition Of Protein Kinase C, Activation Protein-1, And Transglutaminase*, J Biol Chem 2003, 278:33896-903. Hence, cannabinoid modulator can be useful in the treatment of skin diseases.

Recently it has been shown that cannabinoids inhibit keratinocyte proliferation, and therefore support a potential role for cannabinoids in the treatment of psoriasis. Wilkinson J D, Williamson E M, *Cannabinoids Inhibit Human Keratinocyte Proliferation Through A Non-CB1/CB2 Mechanism And Have A Potential Therapeutic Value In The Treatment Of Psoriasis*, J Dermatol Sci 2007, 45:87-92. Cannabinoid receptors have also been described as novel targets for the treatment of melanoma. Blazquez C, Carracedo A, Barrado L, Real P J, Fernandez-Luna J L, Velasco G, Malumbres M, Guzman M, *Cannabinoid Receptors As Novel Targets For The Treatment Of Melanoma*, Faseb J 2006, 20:2633-5. The anti-pruritic activity of CB2 modulators was studied in NC mice with chronic dermatitis, a model of atopic dermatitis. Hence, cannabinoid CB2 receptor modulators may be novel candidate for the medication of pruritus, European Journal of Pharmacology 542 (2006) 179-183.

General Synthetic Methods for Preparing Compounds

The following schemes can be used to practice the present invention.

General synthetic scheme for compounds of Formula I, Formula II, and Formula III are shown in Scheme 1 below:

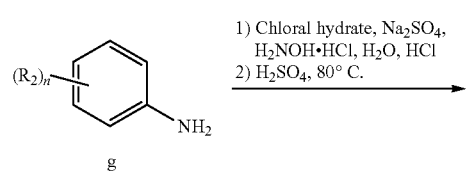

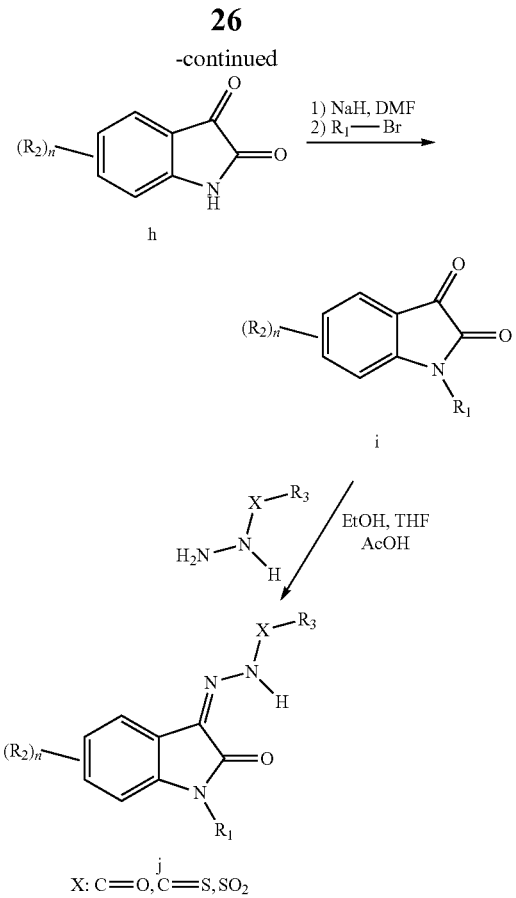

The compounds of Formula I, Formula II, and Formula III may be obtained by reaction of chloral hydrate with the corresponding aniline g, sodium sulfate and hydrochloric acid in water. A solution of hydroxylamine is finally added. After stirring at 80° C. until completion of the reaction, the reaction medium is cooled at room temperature. The precipitate formed is filtered off and dried under vacuum. Concentrated sulfuric acid or polyphosphoric acid is warmed to 50° C. and the corresponding hydroxyl acetanilide is introduced. The solution is then heated at 80° C. for 15 min. The solution is poured into crushed ice. The precipitate formed is filtered and dried. *J. Med. Chem.* 2006, 49, 4638-4649. The indolone h is then alkylated using a base such as sodium hydride and an alkyl halide to afford alkylated product i. The final product j is obtained by addition of the desired functionalized hydrazine in a mixture of solvent such as alcohol and THF and acetic acid.

The synthesis outlined in Scheme 1 proceeds in two chemical steps from commercially available isatin, as outlined in Scheme 2 below:

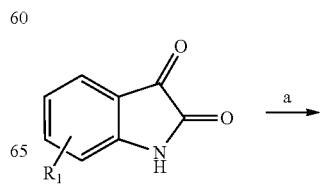

-continued

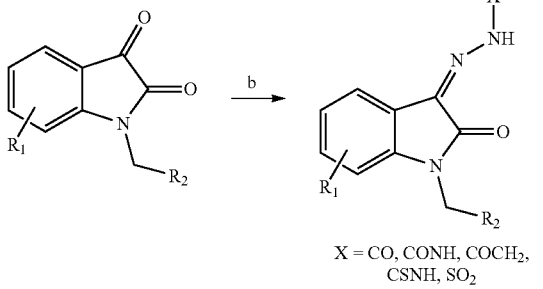

X = CO, CONH, COCH$_2$, CSNH, SO$_2$

Reagents and Condition: (a) NaH, DMF, rt, 2 h followed by R$_2$CH$_2$Br, rt, 12 h or CsCO$_3$, DMF, R$_2$CH$_2$Br, MW irradiation, 140° C., 10 min; (b) H$_2$N—HN—X—R$_3$, AcOH, EtOH, THF, rt, 12 h.

Experimental Section

All chemicals were purchased from Sigma-Aldrich or Acros unless otherwise stated. Microwave reactions were conducted using an Initiator EXP Microwave System (Biotage, Charlottesville, Va.). TLC analyses were performed on Sigma-Aldrich™ TLC plates 60 F254 plates. All air-sensitive reactions were carried out under a nitrogen atmosphere. Column chromatographies were performed with silica gel 230-400 mesh. The LC/MS were performed using a Waters ACQUITY™ TQD instrument. The HPLC-UV analyses were performed using a Waters HPLC system equipped with a photodiode array detector. The HRMS were performed using a mass spectrometer (9.4 tesla) FT-ICR-MS from Varian. Ionization technique was electrospray ionization (ESI). $^1$H NMR spectra were recorded on a Bruker 300 MHz DPX NMR Spectrometer. $^{13}$C NMR spectra were recorded on a Bruker 500 MHz DRX NMR Spectrometer. Chemical shifts in ppm are reported relative to either residual DMSO (3.35 ppm) or CHCl$_3$ (7.24 ppm) as internal standards. Signals were abbreviated as follows: s=singlet, br s=broad singlet, d=doublet, t=triplet, q=quadruplet, m=multiplet. Coupling constants (J) are expressed in hertz.

For hydrazone derivatives of Examples 10 and 7 described below, the $^1$H NMR spectra recorded at room temperature indicated the presence of two isomers. In contrast, only one species was detected by HPLC. These two isomers were shown to be in equilibrium by recording $^1$H NMR spectrum in DMSO at room temperature and at 75° C. At this temperature, only one isomer was detected. After cooling the sample at room temperature, both isomers were detectable, indicating the presence of conformational isomers. Spectroscopic studies of acylhydrazones conformational isomers have been previously reported. Quattropani, A., et al., *Discovery and Development of a New Class of Potent, Selective, Orally Active Oxytocin Receptor Antagonists*, J. Med. Chem., 2005, 48:7882-7905.

X-Ray Diffraction of the Compound of Example 6

Crystals of the compound of Example 6 grew as large, yellow plates by slow evaporation of an ethyl acetate solution. The data crystal was cut from a larger crystal and had approximate dimensions of 0.27×0.25×0.10 mm. The data were collected at room temperature on a Nonius Kappa CCD diffractometer using a graphite monochromator with MoK radiation (λ=0.71073 Å). A total of 383 frames of data were collected using ω-scans with a scan range of 1.1° and a counting time of 136 seconds per frame. The data were collected at 153 K using an Oxford Cryostream low temperature device. Details of crystal data, data collection and structure refinement are listed in Table 1. Data reduction were performed using DENZO-SMN. Otwinowski, Z., et al., *Macromolecular Crystallography, Part A, In Methods in Enzymology*, Academic Press: San Diego, 1997, 276:307-326. The structure was solved by direct methods using SIR97 and refined by full-matrix least-squares on F$^2$ with anisotropic displacement parameters for the non-H atoms using SHELXL-97. Altomare, A., et al., *A New Tool for Crystal Structure Determination and Refinement*, Journal of Applied Crystallography, 1999, 32:115-119; Sheldrick, G. M. U., et al., *Program for the Refinement of Crystal Structures*, University of Gottingen, Germany, 1994. The hydrogen atoms on carbon were calculated in ideal positions with isotropic displacement parameters set to 1.2×Ueq of the attached atom (1.5×Ueq for methyl hydrogen atoms). The hydrogen atoms bound to nitrogen were observed in a ΔF map and refined with isotropic displacement parameters. The function, $\Sigma w(|F_o|^2-|F_c|^2)^2$, was minimized, where $w=1/[(\rho(F_o))^2+(0.0567*P)^2+(0.2659*P)]$ and $P=(|F_o|^2+2|F_c|^2)/3$. $R_w(F^2)$ refined to 0.144, with R(F) equal to 0.0504 and a goodness of fit, S,=1.03. Definitions used for calculating R(F), $R_w(F^2)$ and the goodness of fit, S, are given below.

$R_w(F^2)=\{\Sigma w(|F_o|^2-|F_c|^2)^2/\Sigma w(|F_o|)^4\}^{1/2}$ where w is the weight given each reflection. $R(F)=\Sigma(|F_o|-|F_c|)/\Sigma|F_o|\}$ for reflections with $F_o>4(\rho(F_o))$. $S=[\Sigma w(|F_o|^2-|F_c|^2)^2/(n-p)]^{1/2}$, where n is the number of reflections and p is the number of refined parameters.

The data were corrected for secondary extinction effects. The correction takes the form: $F_{corr}=kF_c/[1+(4.2(4)\times10^{-5})*F_c^2\lambda^3/(\sin 2\theta)]^{0.25}$ where k is the overall scale factor. Neutral atom scattering factors and values used to calculate the linear absorption coefficient are from the International Tables for X-ray Crystallography (1992). Prince, E., *International Tables for Crystallography*, Kluwer Academic Press: Boston, 1992, Tables 4.2.6.8 and 6.1.1.4, Vol. C: Mathematical, physical and chemical tables, p. 255 and p. 578. All figures were generated using SHELXTL/PC. Sheldrick, G. M. U., et al., *Program for the Refinement of Crystal Structures*, University of Gottingen, Germany, 1994.

X-Ray Data for Compound of Example 6

Empirical formula: $C_{21}H_{23}N_3O_2$; Formula weight: 349.42; Temperature: 298(2) K; Wavelength: 0.71073 Å; Crystal system: Triclinic; Space group: P-1; Unit cell dimensions: a=7.9246(4) Å, α=87.074(1)°, b=8.7859(8) Å, β=85.771(1)°, c=28.0323(12) Å, γ=73.203(1)°; Volume: 1862.5(2) Å$^3$; Z: 4; Density (calculated): 1.246 Mg/m$^3$; Absorption coefficient: 0.082 mm$^{-1}$; F(000) 744; Crystal size: 0.27×0.25×0.20 mm; Theta range for data collection: 2.69 to 27.49°; Index ranges: −10<=h<=9, −11<=k<=7, −36<=l<=36; Reflections collected: 10657; Independent reflections: 8267 [R(int)= 0.0240]; Completeness to theta=27.49°: 96.7%; Absorption correction: None; Refinement method: Full-matrix least-squares on F$^2$; Data/restraints/parameters: 8267/0/480; Goodness-of-fit on F$^2$: 1.028; Final R indices [I>2sigma(I)]: R1=0.0504, wR2=0.1212; R indices (all data): R1=0.0964, wR2=0.1440; Extinction coefficient: 4.2(4)×10$^{-5}$; Largest diff. peak and hole: 0.278 and −0.138 e·Å$^{-3}$ General Procedure for the Synthesis of the N-Alkyl Isatin (Method A)

60% sodium hydride (526 mg, 0.013 mol) were added portion wise to a mixture of isatin (1.75 g, 0.012 mol) dissolved in 35 mL of dimethylformamide. The reaction medium was stirred at room temperature for 2 hours. A solution of 1-Bromo-2-cyclohexylethane (2.5 g, 0.013 mol) dissolved in dimethylformamide (3 mL) was then added drop wise. The reaction medium was stirred at room temperature overnight. After extraction with ethyl acetate, the organic layer was washed with hydrochloric acid (0.4 N) and water. The organic fraction was dried over MgSO$_4$ and concentrated under vacuum.

General Procedure for the Synthesis of the N-Alkyl Isatin (Method B)

A mixture of cesium carbonate (732 mg, 2.25 mmol), Isatin (111 mg, 0.75 mmol), 1-(bromomethyl)cyclohexane (200 mg, 1.125 mmol) in dimethylformamide (15 mL), in sealed vessels was irradiated at 140° C. for 10-15 min. After extraction with ethyl acetate, the organic layer was washed with hydrochloric acid (0.4 N) and water. The organic fraction was dried over MgSO$_4$ and concentrated under vacuum.

General Procedure for the Synthesis of the N-Alkyl Isatin (Method C)

A mixture of cesium carbonate (6.52 g, 20 mmol), 5-Iodoisatin (1.47 g, 10 mmol), 1-Bromopentane (1.81 g, 12 mmol) in dimethylformamide (90 mL), was stirred at room temperature overnight. After extraction with ethyl acetate, the organic layer was washed with hydrochloric acid (0.4 N) and water. The organic fraction was dried over MgSO$_4$ and concentrated under vacuum.

General Procedure for the Synthesis of Hydrazone Derivatives from the Corresponding Isatins (Method D)

A solution of 1-(2-Cyclohexyl-ethyl)-isatin (180 mg, 0.70 mmol) and 4-Phenylsemicarbazide (106 mg, 0.70 mmol) in a solution of acetic acid 20%, ethanol 40% and THF 40%, (18 mL) was stirred at room temperature for 24 h. The mixture was then concentrated under vacuum to afford a desired product.

General Procedure for the Synthesis of Hydrazone Derivatives from the Corresponding Isatins (Method E)

A solution of 1-hexyl-isatin (0.5 mmol) and benzhydrazide (68 mg, 0.5 mmol) in a solution of acetic acid 10%, ethanol 45% and THF 45% (6.5 mL) was stirred at room temperature for 24 h. The mixture was then concentrated under vacuum to afford a desired product.

1-(2-cyclohexylethyl)-isatin
(See Compound 2 as shown in Table 5)

The title compound was prepared as an orange solid following Method A. The resulting solid was washed with a mixture of heptane/AcOEt. Yield: 100%. $^1$H NMR (CDCl$_3$): δ 0.92-1.05 (m, 2H), 1.12-1.41 (m, 4H), 1.57 (q, J=6.9 Hz, 2H), 1.63-1.82 (m, 5H), 3.74 (t, J=7.6 Hz, 2H), 6.88 (d, J=7.8 Hz, 1H), 7.11 (t, J=7.5 Hz, 1H), 7.56-7.61 (m, 2H). $^{13}$C NMR (CDCl$_3$): δ 26.09 (CH$_2$), 26.4 (CH$_2$), 33.08 (CH$_2$), 34.42 (CH$_2$), 35.42 (CH), 38.21 (CH$_2$), 110.12 (CH), 117.66 (C), 123.57 (CH), 125.41 (CH), 138.3 (CH), 151.01 (C), 158.03 (C=O). 178.71 (C=O).

1-hexyl-isatin (See Compound 3 as shown in Table 5)

The title compound was prepared as an orange solid following Method A. The resulting solid was washed with a mixture of heptane/AcOEt. Yield: 93%. $^1$H NMR (CDCl$_3$): δ 0.88 (t, J=6.9 Hz, 3H), 1.25-1.38 (m, 6H), 1.7 (m, 2H), 3.72 (t, J=7.5 Hz, 2H), 6.90 (d, J=7.8 Hz, 1H), 7.11 (t, J=7.5 Hz, 1H), 7.56-7.61 (m, 2H). $^{13}$C NMR (CDCl$_3$): δ 13.97 (CH$_3$), 22.50 (CH$_2$), 26.55 (CH$_2$), 27.21 (CH$_2$), 31.38 (CH$_2$), 40.28 (CH$_2$), 110.16 (CH), 117.59 (C), 123.59 (CH), 125.44 (CH), 138.3 (CH), 151.09 (C), 158.13 (C=O). 183.69 (C=O).

1-propyl-isatin (See Compound 4 as shown in Table 5)

The title compound was prepared following Method B to afford a red solid. Yield: 99%. $^1$H NMR (CDCl$_3$): δ 1.00 (t, J=7.2 Hz, 3H), 1.32-1.40 (m, 2H), 1.72 (m, 2H), 3.70 (t, J=7.5 Hz, 2H), 6.90 (d, J=7.8 Hz, 1H), 7.11 (td, J=0.9 Hz, J=7.8 Hz, 1H), 7.56-7.62 (m, 2H). $^{13}$C NMR (CDCl$_3$): δ 11.35 (CH$_3$), 20.64 (CH$_2$), 41.81 (CH$_2$), 110.18 (CH), 117.58 (C), 123.61 (CH), 125.45 (CH), 138.31 (CH), 151.13 (C), 158.21 (C=O). 183.66 (C=O).

1-butyl-isatin (See Compound 5 as shown in Table 5)

The title compound was prepared following Method B. The product was purified by flash chromatography (eluent: AcOEt/Heptane: 2/8) to afford a red oil. Yield: 93%. $^1$H NMR (CDCl$_3$): δ 0.98 (t, J=7.2 Hz, 3H), 1.36-1.48 (m, 2H), 1.64-1.74 (m, 2H), 3.73 (t, J=7.2 Hz, 2H), 6.90 (d, J=8.1 Hz, 1H), 7.16 (td, J=0.6 Hz, J=7.5 Hz, 1H), 7.56-7.62 (m, 2H). $^{13}$C NMR (CDCl$_3$): δ 13.67 (CH$_3$), 20.14 (CH$_2$), 29.29 (CH$_2$), 40.02 (CH$_2$), 110.16 (CH), 117.62 (C), 123.58 (CH), 125.43 (CH), 138.28 (CH), 151.10 (C), 158.14 (C=O). 183.66 (C=O).

1-pentyl-isatin (See Compound 6 as shown in Table 5)

The title compound was prepared as a red solid following Method B. The resulting solid was washed with a mixture of heptane/AcOEt. Yield: 95%. $^1$H NMR (CDCl$_3$): δ 0.91 (t, J=6.9 Hz, 3H), 1.34-1.39 (m, 4H), 1.69-1.73 (m, 2H), 3.72 (t, J=7.2 Hz, 2H), 6.89 (d, J=7.8 Hz, 1H), 7.11 (t, J=7.8 Hz, 1H), 7.56-7.62 (m, 2H). $^{13}$C NMR (CDCl$_3$): δ 13.90 (CH$_3$), 22.29 (CH$_2$), 26.94 (CH$_2$), 28.98 (CH$_2$), 40.24 (CH$_2$), 110.17 (CH), 117.60 (C), 123.57 (CH), 124.40 (CH), 138.31 (CH), 151.09 (C), 158.13 (C=O), 183.67 (C=O).

1-(cyclohexylmethyl)-isatin (See Compound 7 as shown in Table 5)

The title compound was prepared as red solid following Method B. The resulting solid was washed with a mixture of heptane/AcOEt. Yield: 95%. $^1$H NMR (DMSO-d6): δ 0.86-1.3 (m, 6H), 1.62-1.74 (m, 5H), 3.51 (d, J=6.9 Hz, 2H), 7.13 (t, J=7.5 Hz, 1H), 7.20 (d, J=7.8 Hz, 1H), 7.55 (d, J=7.5 Hz, 1H), 7.66 (t, J=7.8 Hz, 2H). $^{13}$C NMR (DMSO-d6): δ 25.70 (CH$_2$), 26.26 (CH$_2$), 30.65 (CH$_2$), 36.20 (CH), 46.15 (CH$_2$), 111.43 (CH), 117.84 (C), 123.55 (CH), 124.85 (CH), 138.64 (CH), 151.70 (C), 158.78 (C=O), 183.91 (C=O).

5-iodo-1-pentyl-isatin (See Compound 8 as shown in Table 5)

The title compound was prepared as an orange solid following Method C. The resulting solid was washed with a mixture of heptane/AcOEt. Yield 15%. $^1$H NMR (CDCl$_3$): δ 0.90 (t, J=6.6 Hz, 3H), 1.30-1.42 (m, 6H), 1.62-1.73 (m, 2H), 3.70 (t, 7.2 Hz, 2H), 6.85 (d, J=8.7 Hz, 1H), 7.86-7.90 (m, 2H). $^{13}$C NMR (CDCl$_3$): δ 13.89 (CH$_3$), 22.27 (CH$_2$), 26.86 (CH$_2$), 28.94 (CH$_2$), 40.37 (CH$_2$), 85.76 (C), 112.32 (CH), 119.15 (C), 133.87 (CH), 146.33 (CH), 150.39 (C), 157.13 (C=O), 182.29 (C=O).

1-[(3Z)-2-(1,3-Dioxo-1,3-dihydro-isoindol-2-yl)-ethyl]-isatin (See Compound 9 as shown in Table 5)

The title compound was prepared following Method B. The product was purified by flash chromatography (eluent: AcOEt/Heptane: 3/7) to afford a red oil. Yield: 71%. $^1$H NMR (DMSO-d6): δ 3.86 (t, J=6 Hz, 2H), 3.97 (t, J=6 Hz, 2H), 7.12 (d, J=7.5 Hz, 1H), 7.24 (d, J=7.8 Hz, 1H), 7.55 (d, J=7.2 Hz, 1H), 7.65 (t, J=7.8 Hz, 1H), 7.82-7.86 (m, 4H). ¹³C NMR (CDCl₃): δ 35.10 (CH₂), 38.59 (CH₂), 110.71 (CH), 117.68 (C), 123.48 (CH), 123.87 (CH), 125.63 (CH), 131.70 (C), 134.25 (CH), 138.33 (CH), 150.42 (C), 158.41 (C=O), 168.07 (C=O), 182.76 (C=O).

1-hexyl-7-methyl-isatin (See Compound 10 as shown in Table 5)

The title compound was prepared as a red solid following Method B. Yield 89%. ¹H NMR (CDCl₃): δ 0.87-0.91 (m, 3H), 1.24-1.41 (m, 6H), 1.60-1.68 (m, 2H), 3.67 (t, J=7.2 Hz, 2H), 3.93 (s, 3H), 6.36 (d, J=2.1 Hz, 1H), 6.54 (dd, J=2.1 Hz, J=8.7 Hz, 1H), 7.59 (d, J=8.7 Hz, 2H). ¹³C NMR (CDCl₃): δ 13.97 (CH₃), 18.81 (CH₃), 22.53 (CH₂), 26.34 (CH₂), 29.44 (CH₂), 31.43 (CH₂), 42.10 (CH₂), 118.90 (C), 121.45 (C), 123.57 (CH), 123.72 (CH), 142.43 (CH), 148.63 (C), 159.31 (C=O), 184.18 (C=O).

7-chloro-1-hexyl-isatin (See Compound 11 as shown in Table 5)

The title compound was prepared as an orange solid following Method B. Yield 85%. ¹H NMR (DMSO-d6): δ 0.89 (t, J=6.9 Hz, 3H), 1.26-1.41 (m, 6H), 1.69-1.79 (m, 2H), 4.09 (t, J=7.8 Hz, 2H), 7.05 (dd, J=7.5 Hz, J=8.1 Hz, 1H), 7.5-7.55 (m, 2H). ¹³C NMR (CDCl₃): δ 13.98 (CH₃), 22.54 (CH₂), 26.27 (CH₂), 29.42 (CH₂), 31.39 (CH₂), 41.99 (CH₂), 117.17 (C), 120.48 (C), 124.10 (CH), 124.61 (CH), 140.63 (CH), 146.48 (C), 158.47 (C=O), 182.85 (C=O).

1-hexyl-7-iodo-isatin (See Compound 12 as shown in Table 5)

The title compound was prepared following Method B. The product was purified by flash chromatography (eluent: AcOEt/Heptane:3/7) to afford an orange solid. Yield 44%. ¹H NMR (DMSO-d6): δ 0.87 (t, J=6.9 Hz, 3H), 1.28-1.38 (m, 6H), 1.60-1.70 (m, 2H), 3.99 (t, J=7.8 Hz, 2H), 6.88 (t, J=7.5 Hz, 1H), 7.55 (dd, J=0.9 Hz, J=7.5 Hz, 1H), 7.59 (dd, J=0.9 Hz, J=7.5 Hz, 2H). ¹³C NMR (CDCl₃): δ 14.35 (CH₃), 22.50 (CH₂), 25.87 (CH₂), 29.36 (CH₂), 31.40 (CH₂), 40.13 (CH₂), 75.10 (C), 121.27 (C), 124.86 (CH), 125.53 (CH), 150.46 (CH), 150.80 (C), 159.39 (C=O), 182.94 (C=O).

1-benzyl-7-iodo-isatin (See Compound 13 as shown in Table 5)

The title compound was prepared following Method B. The product was purified by flash chromatography (eluent: AcOEt/Heptane:5/5) to afford an orange solid. Yield 61%. ¹H NMR (CDCl₃): δ 5.94 (s, 2H), 6.86 (dd, J=7.2 Hz, J=8.1 Hz, 1H), 7.21-7.37 (m, 5H), 7.65 (dd, J=1.2 Hz, J=7.2 Hz, 1H), 7.97 (dd, J=1.2 Hz, J=8.1 Hz, 1H). ¹³C NMR (CDCl₃): δ 43.58 (CH₂), 73.66 (C), 120.77 (C), 125.46 (CH), 125.67 (CH), 126.37 (CH), 127.56 (CH), 128.81 (CH), 135.84 (C), 150.95 (C), 151.12 (CH), 159.11 (C=O), 182.34 (C=O).

1-hexyl-5-methyl-isatin (See Compound 14 as shown in Table 5)

The title compound was prepared as a red solid following Method B. Yield 99%. ¹H NMR (DMSO-d6): δ 0.88 (t, J=6.9 Hz, 3H), 1.32-1.40 (m, 6H), 1.66-1.70 (m, 2H), 2.33 (s, 3H), 3.69 (t, J=7.2 Hz, 2H), 6.78 (d, J=7.8 Hz, 1H), 7.37-7.41 (m, 2H). ¹³C NMR (CDCl₃): δ 13.99 (CH₃), 20.66 (CH₃), 22.51 (CH₂), 26.56 (CH₂), 27.24 (CH₂), 31.40 (CH₂), 40.26 (CH₂), 109.99 (CH), 117.63 (C), 125.79 (CH), 133.39 (C), 138.66 (CH), 148.91 (C), 158.24 (C=O), 183.98 (C=O).

1-hexyl-5-methoxy-isatin (See Compound 15 as shown in Table 5)

The title compound was prepared as an orange solid following Method B. Yield 26%. ¹H NMR (CDCl₃): δ 0.88 (t, J=6.5 Hz, 3H), 1.26-1.38 (m, 6H), 1.66-1.71 (m, 2H), 3.68 (t, 7.5 Hz, 2H), 3.83 (s, 3H), 6.82 (d, J=8.0 Hz, 1H), 7.14-7.15 (m, 2H). ¹³C NMR (CDCl₃): δ 13.98 (CH₃), 22.51 (CH₂), 26.56 (CH₂), 27.24 (CH₂), 31.39 (CH₂), 40.27 (CH₂), 55.99 (CH₃), 109.61 (CH), 111.16 (CH), 118.03 (C), 124.68 (CH), 145.00 (C), 156.39 (C), 158.20 (C=O), 182.07 (C=O).

5-fluoro-1-hexyl-isatin (See Compound 16 as shown in Table 5)

The title compound was prepared following Method B. Column chromatography (silica gel, heptane/EtOAc:6/4) afforded the titled compound as an orange solid, Yield 100%. ¹H NMR (CDCl₃): δ 0.89 (t, J=6.9 Hz, 3H), 1.25-1.42 (m, 6H), 1.63-1.74 (m, 2H), 3.71 (t, 7.5 Hz, 2H), 6.84-6.88 (m, 1H), 7.27-7.33 (m, 2H). ¹³C NMR (CDCl₃): δ 13.97 (CH₃), 22.50 (CH₂), 26.54 (CH₂), 27.12 (CH₂), 31.36 (CH₂), 40.40 (CH₂), 111.28 (d, J=25 Hz, CH), 112.50 (d, J=95 Hz, CH), 118.20 (d, J=25 Hz, C), 124.59 (d, J=95 Hz, CH), 147.11 (s, C), 158.07 (d, J=180 Hz, C=O), 160.21 (s, C), 183.09 (d, J=10 Hz, C=O).

5-chloro-1-hexyl-isatin (See Compound 17 as shown in Table 5)

The title compound was prepared as an orange solid following Method B. Yield 100%. ¹H NMR (CDCl₃): δ 0.89 (t, J=7.2 Hz, 3H), 1.22-1.42 (m, 6H), 1.63-1.73 (m, 2H), 3.71 (t, 7.2 Hz, 2H), 6.85 (d, J=8.1 Hz, 1H), 7.53-7.57 (m, 2H). ¹³C NMR (CDCl₃): δ 13.94 (CH₃), 22.47 (CH₂), 26.51 (CH₂), 27.13 (CH₂), 31.33 (CH₂), 40.43 (CH₂), 111.46 (CH), 118.42 (C), 125.31 (CH), 129.41 (C), 137.65 (CH), 149.34 (C), 157.58 (C=O), 182.64 (C=O).

N-Alkylation of the isatin with commercially available alkyl halide using sodium hydride at room temperature or cesium carbonate with microwave irradiation, in DMF afforded the desired products in moderate to good yields. See Table 5 below for yields:

TABLE 5

Chemical Yields for Isatin Synthesie

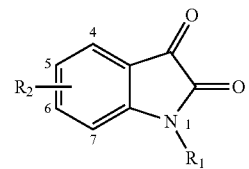

| Compound | R1 | R2 | Position | Yield |
|---|---|---|---|---|
| 2 | 2-cyclohexylethyl | H | — | 100 |
| 3 | CH₃(CH₂)₅ | H | — | 93 |
| 4 | CH₃(CH₂)₂ | H | — | 99 |
| 5 | CH₃(CH₂)₃ | H | — | 93 |
| 6 | CH₃(CH₂)₄ | H | — | 95 |
| 7 | cyclohexylmethyl | H | — | 95 |
| 8 | CH₃(CH₂)₄ | I | 5 | 15 |

TABLE 5-continued

Chemical Yields for Isatin Synthesis

| Compound | R1 | R2 | Position | Yield |
|---|---|---|---|---|
| 9 | (phthalimido-CH2CH2-) | H | — | 71 |
| 10 | $CH_3(CH_2)_5$ | Me | 7 | 89 |
| 11 | $CH_3(CH_2)_5$ | Cl | 7 | 85 |
| 12 | $CH_3(CH_2)_5$ | I | 7 | 44 |
| 13 | Benzyl | I | 7 | 61 |
| 14 | $CH_3(CH_2)_5$ | Me | 5 | 99 |
| 15 | $CH_3(CH_2)_5$ | MeO | 5 | 26 |
| 16 | $CH_3(CH_2)_5$ | F | 5 | 100 |
| 17 | $CH_3(CH_2)_5$ | Cl | 5 | 100 |

Condensation of the resulting N-substituted isatin with hydrazine derivatives afforded the desired hydrazone in good to moderate yields depending on the rate of crystallization in the final step. For hydrazone derivatives of the compounds of Examples 10 and 7 described below, the $^1H$ NMR spectra recorded at room temperature indicated the presence of two isomers. In contrast, only one species was detected by HPLC. These two isomers were shown to be in equilibrium by recording $^1H$ NMR spectrum in DMSO at room temperature and at 75° C. At this temperature, only one isomer was detected. After cooling the sample at room temperature, both isomers were detectable, indicating the presence of conformational isomers. Synthesis of tert-butyl 2-(1-hexyl-2-oxo-1,2-dihydro-3H-indol-3-ylidene)hydrazinecarboxylate afforded 2 isomers (compounds of Examples 14 and 15) which were isolated by column chromatography and studied using 2D ROESY NMR experiments (see below).

Crystallographic Analyses

Figure 8:
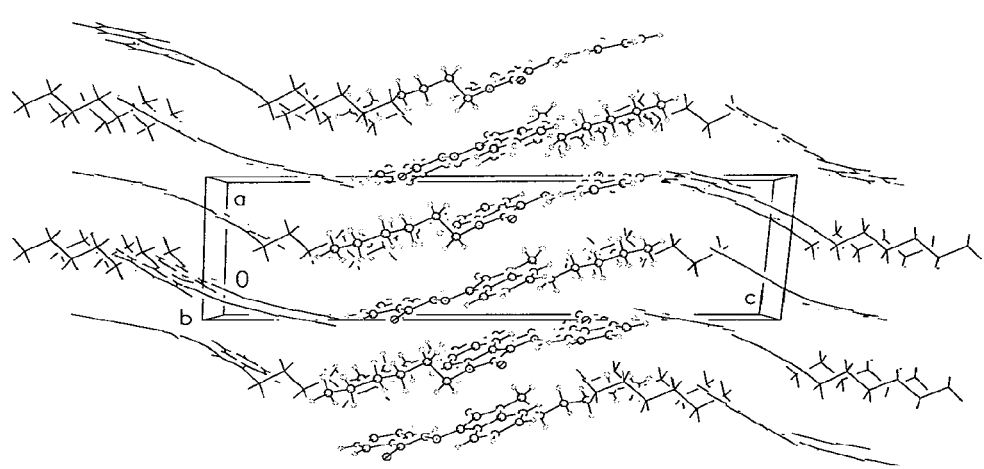
FIG. 8 shows unit cell packing diagram for the compound of Example 6. The view is approximately down the b axis. Molecules stack in layers along a. Molecules of the compound of Example 6a are shown in ball-and-stick format while molecules of the compound of Example 6b are in wireframe display format.
Figure 9:
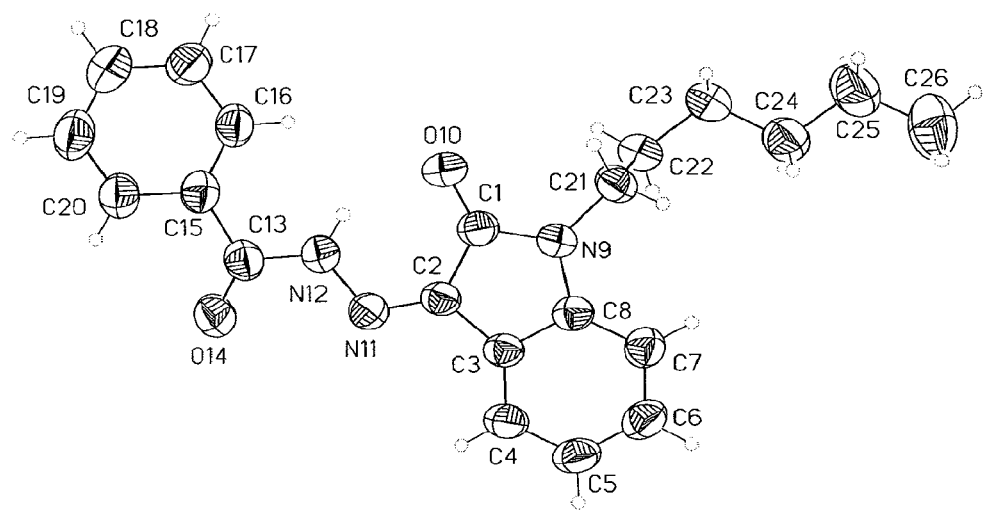
FIG. 9 shows a view of the molecule of the compound of Example 6a showing the atom labeling scheme. Displacement ellipsoids are scaled to the 50% probability level.
Figure 10:
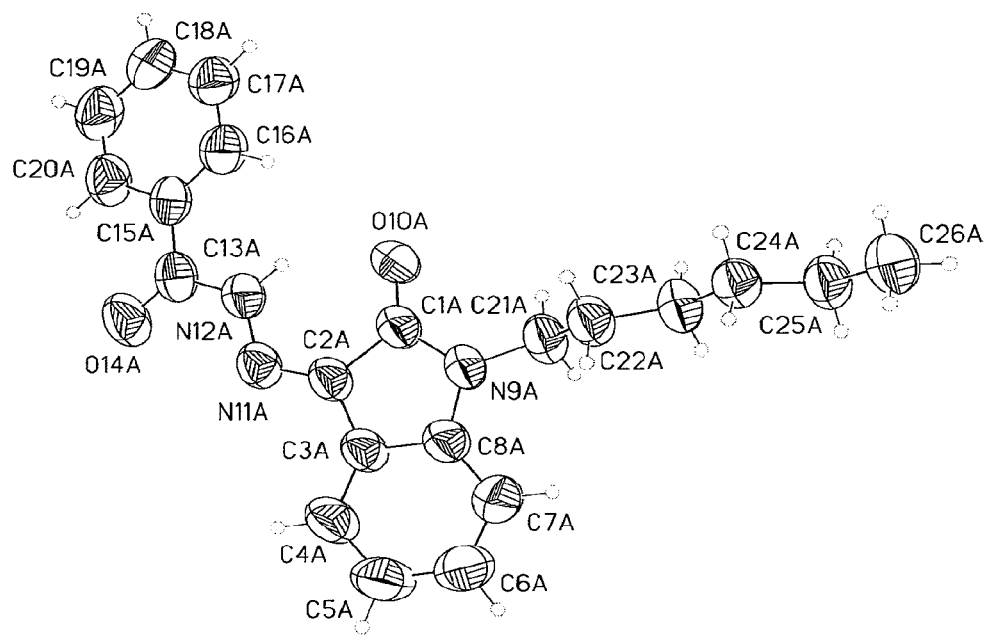
FIG. 10 shows a view of the molecule of the compound of Example 6b showing the atom labeling scheme. Displacement ellipsoids are scaled to the 50% probability level.
Figure 11:
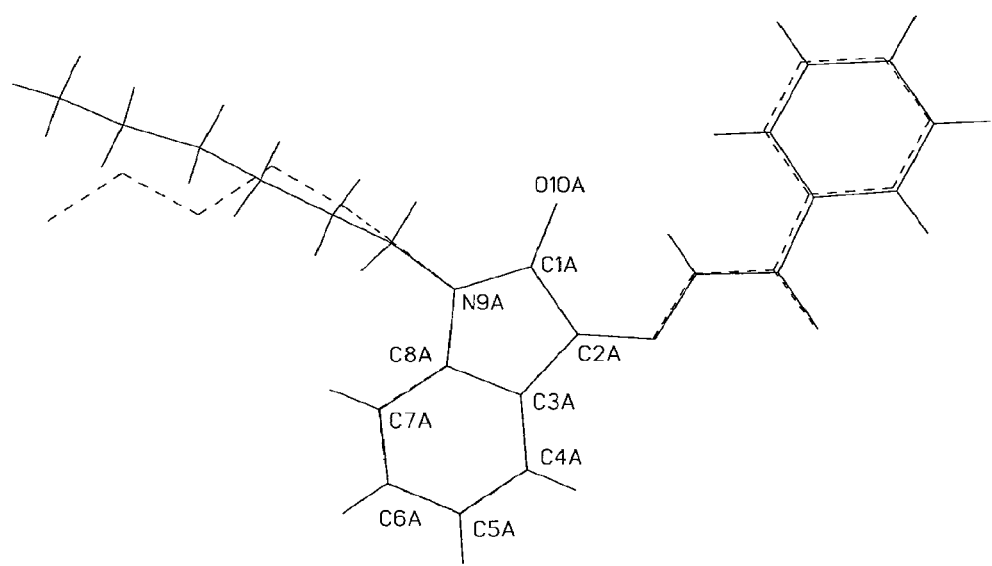
FIG. 11 shows a view illustrating the fit by least-squares of selected atoms from molecule of the compound of Example 6a (dashed lines) to the equivalent atoms of molecule of the compound of Example 6b (solid lines). The atoms of molecule of the compound of Example 6b used in the fit are labeled.

The structure of compound of Example 6 was confined by X-ray diffraction. This compound yielded crystals of suitable quality for X-ray diffraction by slow evaporation of an ethyl acetate solution. Two molecules 6a and 6b appeared in the crystal (FIG. 8). These two molecules have slightly different conformations and crystallographic environments (FIG. 9 and FIG. 10). However, the two conformations for these two crystallographically unique molecules in the asymmetric unit have no impact in term of biological activity. They mainly differ by the conformation adopted by the hexyl chain (FIG. 11). Even if in the solid state, they are different, in solution or in the receptors they might have the same conformation. As expected, the isolated conformer is the one in which the hydrogen bore by nitrogen atom $N_{12}$ might form a hydrogen bond with the oxygen atom $O_{10}$.

2D ROESY NMR Analyses

2D NMR spectra were recorded for the compounds of Examples 6, 14 and 15 to reveal information about short interproton distances (off-resonance Overhauser enhancement spectroscopy ROESY). The ROESY 2D NMR established the E-geometry of the imino double bond for the compound of Example 15. A cross-peak for N—H and the aromatic C—H(4) characterizing a through space interaction of the hydrazino hydrogen and the aromatic CH(4) established the E-geometry for the compound of Example 15. This interaction was absent for compounds of Examples 14 and 6.

The invention is further illustrated by the following examples.

EXAMPLE 1

Phenyl thiocarbamoyl[1-(2-cyclohexyl-ethyl)-2-oxo-1,2-dihydro-indol-3-ylidene]-hydrazide

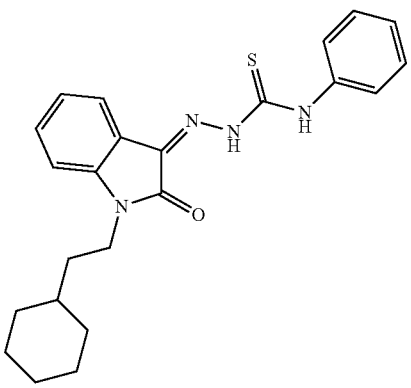 [SMILES: O=C1/C(=N\NC(=S)Nc2ccccc2)c2ccccc2N1CCC1CCCCC1]

A solution of 1-(2-Cyclohexyl-ethyl)-isatine (180 mg, 0.70 mmol) previously obtained (see isatine 2 in table 5), and 4-Phenylthiosemicarbazide (117 mg, 0.70 mmol) in a solution of acetic acid, ethanol and THF (20%, 40%, 40%) is stirred at room temperature for 12 h. After concentration, an orange precipitate is filtered and washed with ethanol to afford a desired product. M=207 mg, Yield: 73%.

NMR (DMSO, $^1H$): 0.92 to 1.80 (13H, m), 3.78 (2H, t, J=7.5 Hz), 7.15 to 7.20 (2H, m), 7.30 (1H, t, J=7.5 Hz), 7.40 to 7.48 (2H, m), 7.61 (2H, d, J=8.4 Hz), 7.83 (1H, d, J=7.5 Hz), 10.85 (1H, s), 12.75 (1H, s).

EXAMPLE 2

Phenyl thiocarbamoyl[1-n-hexyl-2-oxo-1,2-dihydro-indol-3-ylidene]-hydrazide

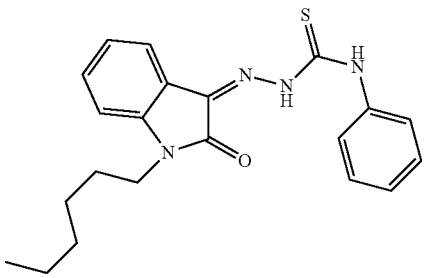 [SMILES: CCCCCCN1C(=O)/C(=N\NC(=S)Nc2ccccc2)c2ccccc21]

1-hexyl-1H-indole-2,3-dione
3-(N-phenylthiosemicarbazone)

A solution of 1-(2-Cyclohexyl-ethyl)-isatine (170 mg, 0.73 mmol) previously obtained (see isatine 3 in table 5) and 4-Phenylthiosemicarbazide (123 mg, 0.73 mmol) in 19 ml of a solution of acetic acid, ethanol and THF (20%, 40%, 40%) is stirred at room temperature for 12 h. After concentration, an orange precipitate is filtered and washed with ethanol to afford a desired product. M: 244 mg. Yield: 87%.

NMR (DMSO, $^1$H): 0.85 (3H, t, J=6.3 Hz), 1.29 (6H, br s), 1.65 (2H, br t), 3.76 (2H, t, J=6.9 Hz), 7.15 to 7.22 (2H, m), 7.28 (1H, t, J=7.5 Hz), 7.41 to 7.48 (3H, m), 7.61 (1H, d, J=7.8 Hz), 7.83 (1H, d, J=7.2 Hz), 10.85 (1H, s), 12.75 (1H, s).

EXAMPLE 3

Phenyl carbamoyl[1-(2-cyclohexyl-ethyl)-2-oxo-L2-dihydro-indol-3-ylidene]-hydrazide

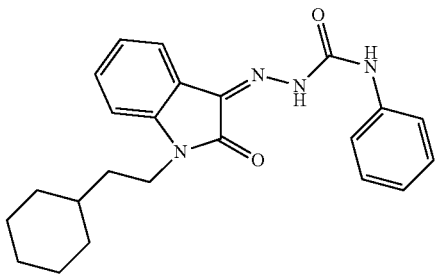 [SMILES: O=C(N/N=C1\C(=O)N(CCC2CCCCC2)c2ccccc21)Nc1ccccc1]

1-(2-cyclohexylethyl)-1H-indole-2,3-dione 3-(N-phenylsemicarbazone)

A solution of 1-(2-Cyclohexyl-ethyl)-isatine (180 mg, 0.70 mmol) previously obtained (see isatine 2 in table 5), and 4-Phenylsemicarbazide (106 mg, 0.70 mmol) in a solution of acetic acid, ethanol and THF (20%, 40%, 40%) is stirred at room temperature for 12 h. After concentration, a yellow precipitate is filtered and washed with ethanol to afford a desired product. M=200 mg. Yield: 73%.

NMR (DMSO, $^1$H): 0.90 to 1.80 (13H, m), 3.76 (2H, t, J=7.2 Hz), 7.07 to 7.14 (3H, m), 7.36 (2H, d, J=7.5 Hz), 7.47 (1H, t, J=7.8 Hz), 7.58 (2H, d, J=7.5 Hz), 8.13 (1H, d, J=7.5 Hz), 9.51 (1H, s), 10.45 (1H, s).

EXAMPLE 4

Phenyl carbamoyl[1-n-hexyl-2-oxo-1,2-dihydro-indol-3-ylidene]-hydrazide

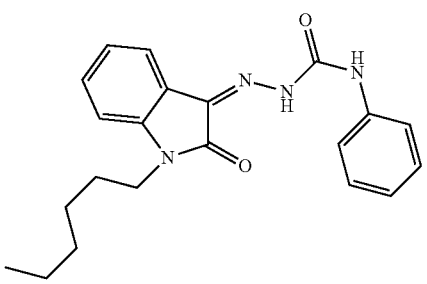 [SMILES: CCCCCCN1C(=O)/C(=N\NC(=O)Nc2ccccc2)c2ccccc21]

1-(1-hexyl)-1H-indole-2,3-dione 3-(N-phenylsemicarbazone)

A solution of 1-(2-Cyclohexyl-ethyl)-isatine (170 mg, 0.73 mmol) previously obtained (see isatine 3 in table 5) and 4-Phenylsemicarbazide (111 mg, 0.73 mmol) in 19 ml of a solution of acetic acid, ethanol and THF (20%, 40%, 40%) is stirred at room temperature for 12 h. After concentration, a yellow precipitate is filtered and washed with ethanol to afford a desired product. M=265 mg, Yield: 100%.

NMR (DMSO, $^1$H): 0.85 (3H, t, J=6.6 Hz), 1.23 to 1.29 (6H, m), 1.58 (2H, br, t), 3.73 (2H, t, J=6.9 Hz), 7.07 (1H, t, J=7.5 Hz), 7.13 to 7.17 (2H, m), 7.35 (2H, t, J=7.8 Hz), 7.46 (1H, t, J=7.8 Hz), 7.59 (2H, s, J=7.8 Hz), 8.13 (1H, d, J=7.5 Hz), 9.52 (1H, s), 10.46 (1H, s).

EXAMPLE 5

Benzoic acid [1-(2-cyclohexyl-ethyl)-2-oxo-1,2-dihydro-indol-3-ylidene]-hydrazide

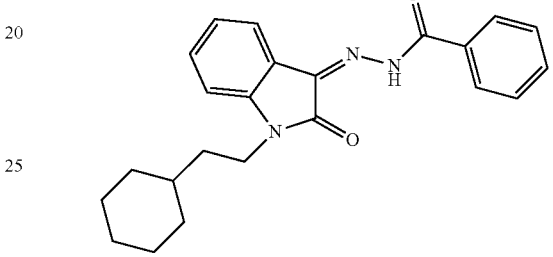

A solution of 1-(2-Cyclohexyl-ethyl)-isatine (180 mg, 0.70 mmol) previously obtained (see isatine 2 in table 5) and Benzhydrazide (95 mg, 0.70 mmol) in 19 mL of a solution of acetic acid, ethanol and THF (20%, 40%, 40%) is stirred at room temperature for 12 h. A yellow precipitate is filtered and washed with ethanol to afford the desired product. M: 163 mg.

NMR (DMSO, $^1$H): 0.90 to 1.79 (13H, m), 3.79 (2H, t, J=7.5 Hz), 7.16 to 7.211 (2H, m), 7.49 (1H, td, J1=1.2 Hz, J2=7.8 Hz), 7.602 to 7.73 (4H, m), 7.91 92H, dd, J1=1.5 Hz, J2=6.9 Hz), 13.9 (1H, s).

EXAMPLE 6

Benzoic acid [1-n-hexyl-2-oxo-1,2-dihydro-indol-3-ylidene]-hydrazide

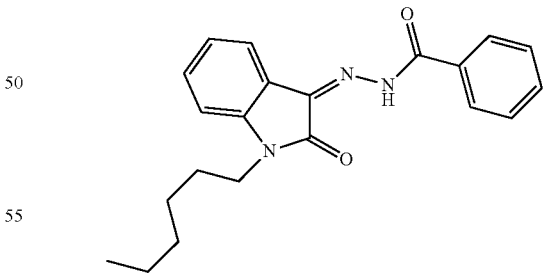

A solution of 1-(2-Cyclohexyl-ethyl)-isatine (170 mg, 0.73 mmol) previously obtained (see isatine 3 in table 5) and Benzhydrazide (100 mg, 0.73 mmol) in 19 ml of a solution of acetic acid, ethanol and THF (20%, 40%, 40%) is stirred at room temperature for 12 h. A yellow precipitate is filtered and washed with ethanol to afford the desired product. M: 201 mg, Yield: 78%.

NMR (DMSO, $^1$H): 0.85 (3H, t, J=6.6 Hz), 1.23 to 1.29 (6H, m), 1.65 (2H, br t), 3.77 (2H, t, J=7.2 Hz), 7.18 (1H, t,

J=6 Hz), 7.23 (1H, d, J=6 Hz), 7.48 (1H, td, J=1.2, J=6.6 Hz), 7.60 to 7.73 (4H, m), 7.90 to 7.93 (2H, m), 13.90 (1H, br s).

EXAMPLE 7

Phenylacetic acid [1-n-hexyl-2-oxo-1,2-dihydro-indol-3-ylidene]-hydrazide

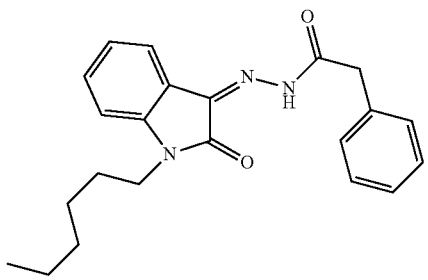 [SMILES: CCCCCCN1C(=O)/C(=N\NC(=O)Cc2ccccc2)c2ccccc21]

A) Phenyl-acetic acid [1-hexyl-2-oxo-1,2-dihydro-indol-3-ylidene]-hydrazide

A solution of 1-(2-Cyclohexyl-ethyl)-isatine (170 mg, 0.73 mmol) previously obtained (see isatine 3 in table 5) and Phenylacetic hydrazide (110 mg, 0.73 mmol) in 19 ml of a solution of acetic acid, ethanol and THF (20%, 40%, 40%) is stirred at room temperature for 12 h. A yellow precipitate is filtered and washed with ethanol to afford the desired product. M: 213 mg, Yield: 80%.

NMR (DMSO, $^1$H): 0.84 (3H, t, J=6.6 Hz), 1.26 (6H, br s), 1.61 (2H, br t), 3.72 (2H, t, J=6.9 Hz), 3.83 (2H, br s, minor conformer 30%), 4.13 (2H, br s, major conformer 70%), 7.13 to 7.35 (7H, m), 7.45 (1H, t, J=7.5 Hz), 7.64 (1H, br s), 12.48 (1H, br s, major conformer 70%), 12.92 (1H, br s, minor conformer 30%).

EXAMPLE 8

Phenyl sulfonyl[1-(2-cyclohexyl-ethyl)-2-oxo-L2-dihydro-indol-3-ylidene]-hydrazide

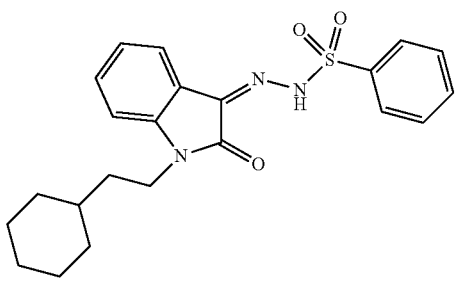 [SMILES: O=C1/C(=N\NS(=O)(=O)c2ccccc2)c2ccccc2N1CCC1CCCCC1]

N'-[(1-(2-cyclohexylethyl)-2-oxo-1,2-dihydro-3H-indol-3-ylidene]benzenesulfonohydrazide A solution of 1-(2-Cyclohexyl-ethyl)-isatine (180 mg, 0.70 mmol) previously obtained (see isatine 2 in table 5) and Benzenesulfonyl hydrazide (120 mg, 0.70 mmol) in a solution of acetic acid, ethanol and THF (20%, 40%, 40%) is stirred at room temperature for 12 h. After concentration, a yellow precipitate is filtered and washed with ethanol to afford a desired product. M=239 mg, Yield: 83%.

NMR (DMSO, $^1$H): 0.85 to 1.76 (13H, m), 3.70 (2H, t, J=7.2 Hz), 7.07 to 7.12 (2H, m), 7.40 to 7.49 (2H, m), 7.61 to 7.20 (3H, m), 7.99 (1H, d, J=7.2 Hz), 12.55 (1H, s).

EXAMPLE 9

Phenyl sulfonyl[1-n-hexyl-2-oxo-1,2-dihydro-indol-3-ylidene]-hydrazide

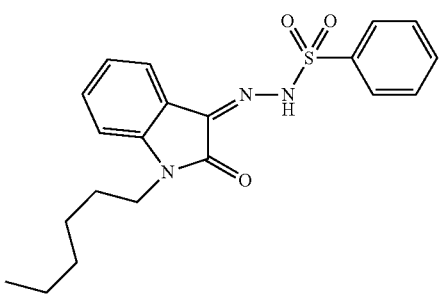 [SMILES: CCCCCCN1C(=O)/C(=N\NS(=O)(=O)c2ccccc2)c2ccccc21]

A solution of 1-(2-Cyclohexyl-ethyl)-isatine (170 mg, 0.73 mmol) previously obtained (see isatine 3 in table 5) and Benzenesulfonyl hydrazide (126 mg, 0.73 mmol) in 19 ml of a solution of acetic acid, ethanol and THF (20%, 40%, 40%) is stirred at room temperature for 12 h. After concentration, a yellow precipitate is filtered and washed with ethanol to afford a desired product. M: 54 mg, Yield: 20%

NMR (DMSO, $^1$H): 0.83 (3H, t, J=6.6 Hz), 1.25 (6H, br s), 1.58 (2H, br t), 3.68 (2H, t, J=6.9 Hz), 7.10 (1H, t, J=7.8 Hz), 7.15 (1H, d, J=7.8 Hz), 7.43 (1H, t, J=7.8 Hz), 7.48 (1H, d, J=7.5 Hz), 7.61 to 7.72 (3H, m), 7.98 to 8.00 (2H, m), 12.54 (1H, s).

EXAMPLE 10

N'-[1-(2-cyclohexylethyl)-2-oxo-1,2-dihydro-3H-indol-3-ylidene]-2-phenylacetohydrazide

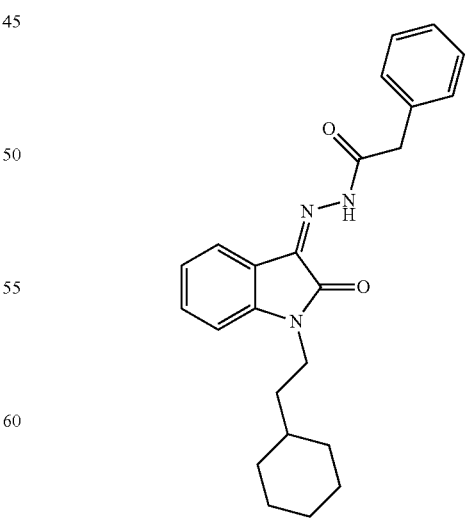

The title compound was prepared as an orange solid, using isatin 2 according to the synthetic following Method D. The resulting solid was washed with ethanol. Yield: 80%. $^1$H NMR (DMSO-d6): δ 0.85-1.31 (m, 6H), 1.48 (q, J=6.6 Hz, 2H), 1.62-1.76 (m, 5H), 3.71 (t, J=7.2 Hz, 2H), 3.82 (br s, 1H, minor isomer (28%)), 4.11 (br s, 1H, major isomer (72%)), 7.11-7.17 (m, 2H), 7.27-7.34 (m, 5H), 7.44 (t, J=7.8 Hz, 1H), 7.62 (br s, 1H), 12.45 (br s, 1H, major isomer), 12.90 (br, s, 1H, minor isomer). At 75° C. peaks with a displacement of 3.82 ppm and 4.11 ppm corresponding to the benzylic CH2 are converted to a singlet at 4.02 ppm. Identically, peaks with a displacement of 12.45 ppm and 12.90 ppm are converted to a singlet with a displacement of 12.50 ppm. $^{13}$C NMR (DMSO-d6): δ 26.09 (CH$_2$), 26.46 (CH$_2$), 32.95 (CH$_2$), 34.64 (CH$_2$), 35.08 (CH), 37.55 (CH$_2$), 110.41 (CH), 119.71 (C), 120.93 (CH), 123.51 (CH), 127.21 (CH), 128.86 (CH), 129.47 (C), 130.00 (CH), 131.95 (CH), 135.05 (C), 143.20 (C=N), 160.85 (C=O). HRMS (ES+) calcd for C$_{24}$H$_{28}$N$_3$O$_2$ (M+H$^+$), m/e, 390.2181. found, 390.2176.

EXAMPLE 11

N'-[(3Z)-1-hexyl-2-oxo-1,2-dihydro-3H-indol-3-ylidene]cyclohexanecarbohydrazide

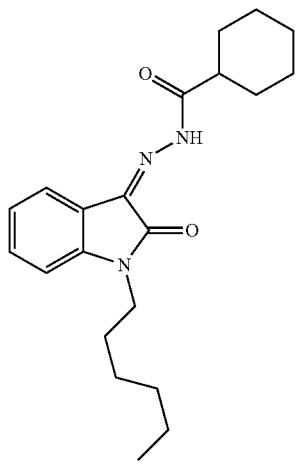 [SMILES: CCCCCCN1C(=O)/C(=N\NC(=O)C2CCCCC2)c2ccccc21]

The title compound was prepared as a yellow solid, using isatin 3 and cyclohexanecarbohydrazide according to the synthetic method E. The resulting solid was washed with ethanol. Yield: 45%. $^1$H NMR (DMSO-d6): δ δ 0.85 (t, J=6.8 Hz, 3H), 1.24-1.83 (m, 19H), 3.74 (t, J=6.9 Hz, 2H), 7.15 (t, J=7.5 Hz, 1H), 7.19 (d, J=7.8 Hz, 1H), 7.45 (t, J=7.8 Hz, 1H), 7.48 (d, J=7.5 Hz, 1H), 7.59 (d, 3H), 12.34 (br s, isomer 1: 50%, 0.5; H), 13.00 (br s, isomer 2: 50%, 0.5; H), both isomer are in the same proportion. $^{13}$C NMR (DMSO-d6): δ 14.33(CH$_3$), 22.42 (CH$_2$), 25.48 (CH$_2$), 26.34 (CH$_2$), 25.83 (CH$_2$), 27.37 (CH$_2$), 31.29 (CH$_2$), 39.64 (CH$_2$), 110.52 (CH), 119.78 (C), 123.48 (CH), 131.79 (CH), 143.27 (C=N), (C=O). HRMS (ES+) calcd for C$_{21}$H$_{30}$N$_3$O$_2$ (M+H$^+$), m/e, 356.2328. found, 356.2333.

EXAMPLE 12

N'-[(3Z)-1-hexyl-2-oxo-1,2-dihydro-3H-indol-3-ylidene]hexanohydrazide

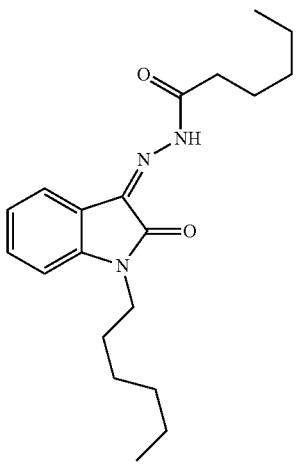 [SMILES: CCCCCCN1C(=O)/C(=N\NC(=O)CCCCC)c2ccccc21]

The title compound was prepared as a yellow solid, using isatin 3 and hexanecarbohydrazide according to the synthetic method E. The resulting solid was washed with ethanol. Yield: 32%. $^1$H NMR (DMSO-d6): δ 0.82-0.91 (m, 6H), 1.27-1.33 (m, 10H), 1.62 (m, 4H), 2.71 (br s, 1H), 3.74 (t, J=7.2 Hz, 2H), 7.15 (t, J=7.5 Hz, 1H), 7.19 (d, J=7.8 Hz, 1H), 7.45 (t, J=7.8 Hz, 1H), 7.58 (d, J=7.5 Hz, 1H), 12.44 (br s, 1H). $^{13}$C NMR (DMSO-d6): δ 14.25 (CH$_3$), 14.29 (CH$_3$), 22.30 (CH$_2$), 22.42 (CH$_2$), 26.33 (CH$_2$), 27.36 (CH$_2$), 31.26 (CH$_2$), 31.28 (CH$_2$), 39.59 (CH$_2$), 110.46 (CH), 119.72 (C), 120.62 (CH), 123.41 (CH), 131.73 (CH), 143.22 (C=N), 161.01 (C=O). HRMS (ES+) calcd for C$_{20}$H$_{30}$N$_3$O$_2$ (M+H$^+$), m/e, 344.2335. found, 344.2333.

EXAMPLE 13

4-chloro-N'-[(3Z)-1-hexyl-2-oxo-1,2-dihydro-3H-indol-3-ylidene]benzohydrazide

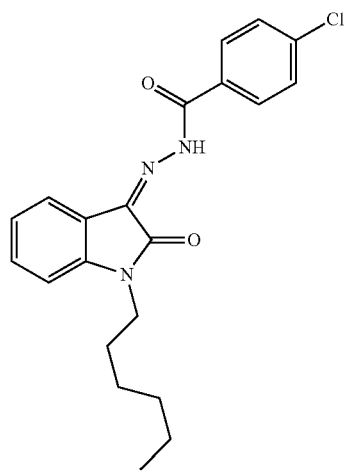 [SMILES: CCCCCCN1C(=O)/C(=N\NC(=O)c2ccc(Cl)cc2)c2ccccc21]

The title compound was prepared as a yellow solid, using isatin 3 and 4-chlorobenzhydrazide according to the synthetic method E. The resulting solid was washed with ethanol. Yield: 80%. $^1$H NMR (DMSO-d6): δ 0.85 (t, J=6.9 Hz, 3H), 1.25-1.38 (m, 6H), 1.64 (m, 2H), 3.76 (t, J=7.2 Hz, 2H), 7.18 (t, J=7.8 Hz, 1H), 7.23 (d, J=7.8 Hz, 1H), 7.48 (t, J=7.8 Hz, 1H), 7.64-7.72 (m, 3H), 7.91-7.94 (m, 2H), 13.85 (br s, 1H).

$^{13}$C NMR (DMSO-d6): δ 14.32 (CH$_3$), 22.41 (CH$_2$), 26.37 (CH$_2$), 27.38 (CH$_2$), 31.31 (CH$_2$), 39.80 (CH$_2$), 110.69 (CH), 119.56 (C), 121.33 (CH), 123.72 (CH), 129.75 (CH), 131.20 (C), 132.35 (CH), 138.23 (C), 143.52 (C=N), 161.55 (C=O). HRMS (ES+) calcd for C$_{21}$H$_{23}$N$_3$O$_2$Cl (M+H$^+$), m/e, 384.1484. found, 384.1473.

EXAMPLE 14 tert-butyl (2Z)-2-(1-hexyl-2-oxo-1,2-dihydro-3H-indol-3-ylidene)hydrazinecarboxylate

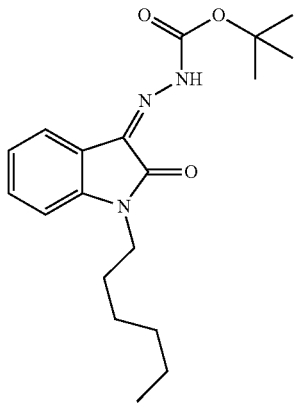 [SMILES: CCCCCCN1C(=O)/C(=N\NC(=O)OC(C)(C)C)c2ccccc21]

The title compound was prepared using isatin 3 and tert-butoxycarbonyl hydrazide according to the synthetic method E. The product was purified by flash chromatography (eluent: AcOEt/heptane:4/6) to afford a yellow oil which crystallized (Rf: 0.5). Yield: 8.5%. $^1$H NMR (CDCl$_3$): δ 0.88 (t, J=7.2 Hz, 3H), 1.25 to 1.33 (m, 6H), 1.56 (s, 9H), 1.65-1.72 (m, 2H), 3.74 (t, J=7.2 Hz, 2H), 6.87 (d, J=7.8 Hz, 1H), 7.10 (t, J=7.5 Hz, 1H), 7.34 (t, J=7.8 Hz, 1H), 7.74 (d, J=7.5 Hz, 1H), 12.33 (br s, 1H). $^{13}$C NMR (CDCl$_3$): δ 14.01 (CH$_3$), 22.49 (CH$_2$), 26.63 (CH$_2$), 27.54 (CH$_2$), 28.15 (CH$_3$), 31.41 (CH$_2$), 39.77 (CH$_2$), 82.46 (C), 108.98 (CH), 120.15 (C), 121.31 (CH), 123.10 (CH), 130.54 (CH), 134.02 (C), 142.39 (C=N), 152.32 (C=O), 161.46 (C=O). HRMS (ES+) calcd for C$_{19}$H$_{28}$N$_3$O$_3$ (M+H$^+$), m/e, 346.2138. found, 346.2125.

EXAMPLE 15 tert-butyl (2E)-2-(1-hexyl-2-oxo-1,2-dihydro-3H-indol-3-ylidene)hydrazinecarboxylate

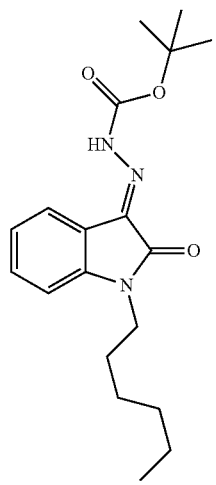 [SMILES: CCCCCCN1C(=O)/C(=N/NC(=O)OC(C)(C)C)c2ccccc21]

The title compound was prepared using isatin 3 and tert-butoxycarbonyl hydrazide according to the synthetic method E. The product was purified by flash chromatography (eluent: AcOEt/heptane:4/6) to afford a yellow oil which crystallized (Rf: 0.1). Yield: 76.5%. $^1$H NMR (CDCl$_3$): δ 0.87 (t, J=6.9 Hz, 3H), 1.27 to 1.37 (m, 6H), 1.59 (s, 9H), 1.61-1.69 (m, 2H), 3.75 (t, J=7.2 Hz, 2H), 6.91 (d, J=8.1 Hz, 1H), 7.10 (t, J=7.5 Hz, 1H), 7.41 (t, J=8.1 Hz, 1H), 7.58 (d, J=7.5 Hz, 1H), 8.75 (br s, 1H). $^{13}$C NMR (CDCl$_3$): δ 14.00 (CH$_3$), 22.50 (CH$_2$), 26.54 (CH$_2$), 27.41 (CH$_2$), 28.11 (CH$_3$), 31.47 (CH$_2$), 40.04 (CH$_2$), 83.49 (C), 109.47 (CH), 115.51 (C), 122.33 (CH), 124.10 (CH), 123.22 (CH), 135.22 (C), 144.46 (C=N), 151.90 (C=O), 163.55 (C=O). HRMS (ES+) calcd for C$_{19}$H$_{28}$N$_3$O$_3$ (M+H$^+$), m/e, 346.2138. found, 346.2125.

EXAMPLE 16

N'-[(3Z)-1-hexyl-2-oxo-1,2-dihydro-3H-indol-3-ylidene]-2-naphthohydrazide

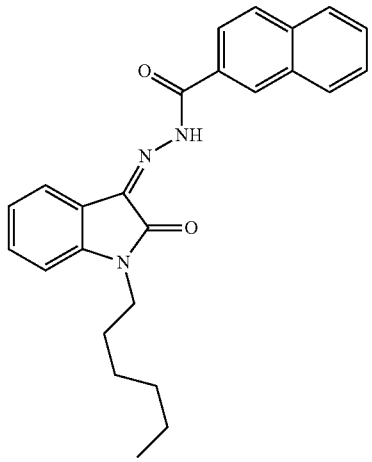 [SMILES: CCCCCCN1C(=O)/C(=N\NC(=O)c2ccc3ccccc3c2)c2ccccc21]

The title compound was prepared as a yellow solid, using isatin 3 and 2-naphthhydrazide according to the synthetic method E. The resulting solid was washed with ethanol. Yield: 86%. $^1$H NMR (DMSO-d6): δ 0.85 (t, J=6.9 Hz, 3H), 1.22-1.38 (m, 6H), 1.66 (m, 2H), 3.79 (t, J=7.2 Hz, 2H), 7.19 (t, J=7.5 Hz, 1H), 7.24 (d, J=7.8 Hz, 1H), 7.49 (t, J=7.8 Hz, 1H), 7.63-7.73 (m, 3H), 7.94 (dd, J=1.8 Hz, J=8.4 Hz, 1H), 8.05 (d, J=7.5 Hz, 1H), 8.13-8.17 (m, 2H), 8.55, (s, 1H), 14.01 (br s, 1H). $^{13}$C NMR (DMSO-d6): δ 14.32 (CH$_3$), 22.44 (CH$_2$), 26.39 (CH$_2$), 27.43 (CH$_2$), 31.33 (CH$_2$), 39.79 (CH$_2$), 110.66 (CH), 119.69 (C), 121.27 (CH), 123.68 (CH), 127.74 (CH), 128.24 (CH), 129.03 (CH), 129.38 (CH), 129.70 (CH), 129.74 (C), 132.21 (CH), 132.63 (C), 135.22 (C), 143.45 (C=N), 161.58 (C=O). HRMS (ES+) calcd for C$_{25}$H$_{26}$N$_3$O$_2$ (M+H$^+$), m/e, 400.2031. found, 400.2020.

EXAMPLE 17

N'-[(3Z)-1-hexyl-2-oxo-1,2-dihydro-3H-indol-3-ylidene]-4-methoxybenzohydrazide

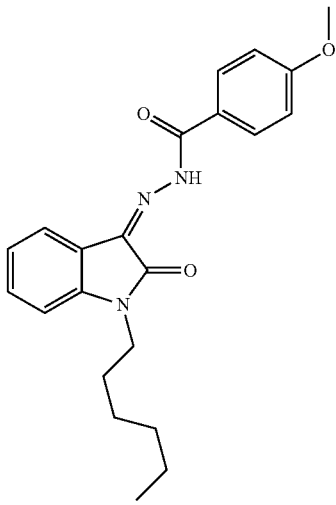 [SMILES: CCCCCCN1C(=O)/C(=N\NC(=O)c2ccc(OC)cc2)c2ccccc21]

The title compound was prepared as a yellow solid, using isatin 3 and 4-methoxybenzhydrazide according to the synthetic method E. The resulting solid was washed with ethanol. Yield: 79%. $^1$H NMR (DMSO-d6): δ 0.85 (t, J=6.9 Hz, 3H), 1.26-1.36 (m, 6H), 1.65 (m, 2H), 3.79 (t, J=7.2 Hz, 2H), 3.87 (s, 3H), 7.14-7.24 (m, 4H), 7.48 (t, J=7.8 Hz, 1H), 7.65 (d, J=7.5 Hz, 1H), 7.89 (d, J=9 Hz, 2H), 13.86 (br s, 1H). $^{13}$C NMR (DMSO-d6): δ 14.33 (CH$_3$), 22.43 (CH$_2$), 26.39 (CH$_2$), 27.41 (CH$_2$), 31.32 (CH$_2$), 39.77 (CH$_2$), 56.07 (O—CH$_3$), 110.63 (CH), 114.97 (CH), 119.76 (C), 121.13 (CH), 123.64 (CH), 124.46 (C), 129.98 (CH), 132.02 (CH), 143.30 (C=N), 161.63 (C=O), 163.68 (C=O). HRMS (ES+) calcd for C$_{22}$H$_{26}$N$_3$O$_3$ (M+H$^+$), m/e, 380.1974. found, 380.1969.

EXAMPLE 18

N'-[(3Z)-1-hexyl-2-oxo-1,2-dihydro-3H-indol-3-ylidene]-1-benzothiophene-2-carbohydrazide

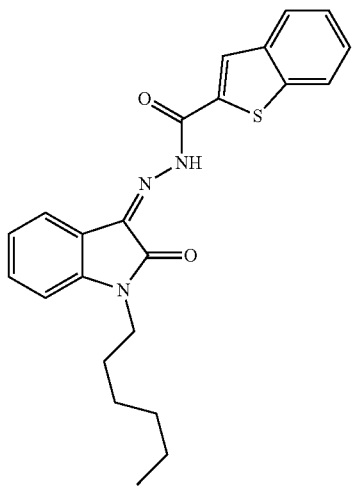 [SMILES: CCCCCCN1C(=O)/C(=N\NC(=O)c2cc3ccccc3s2)c2ccccc21]

The title compound was prepared as a yellow solid, using isatin 3 and Benzo[b]thiophene-2-carboxylic hydrazide according to the synthetic method E. The resulting solid was washed with ethanol. Yield: 82%. $^1$H NMR (DMSO-d6): δ 0.86 (t, J=6.9 Hz, 3H), 1.26-1.36 (m, 6H), 1.64-1.66 (m, 2H), 3.79 (t, J=7.2 Hz, 2H), 7.19-7.27 (m, 2H), 7.48-7.59 (m, 3H), 7.75 (d, J=7.5 Hz, 1H), 8.13 (d, J=7.5 Hz, 2H), 8.31 (br s, 1H), 13.65 (br s, 1H). $^{13}$C NMR (DMSO-d6): δ 14.33 (CH$_3$), 22.44 (CH$_2$), 26.40 (CH$_2$), 27.41 (CH$_2$), 31.34 (CH$_2$), 39.81 (CH$_2$), 110.71 (CH), 115.52 (C), 119.55 (C), 121.52 (CH), 123.35 (CH), 123.69 (CH), 125.75 (CH), 126.51 (CH), 127.83 (CH), 132.38 (CH), 143.64 (C=N), 161.60 (C=O). HRMS (ES+) calcd for C$_{23}$H$_{24}$N$_3$O$_2$S (M+H$^+$), m/e, 406.1596. found, 406.1584.

EXAMPLE 19

N'-[(3Z)-1-hexyl-2-oxo-1,2-dihydro-3H-indol-3-ylidene]-1-naphthohydrazide

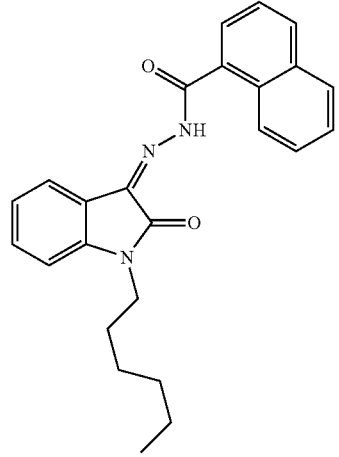 [SMILES: CCCCCCN1C(=O)/C(=N\NC(=O)c2cccc3ccccc23)c2ccccc21]

The title compound was prepared using isatin 3 and 1-naphthhydrazide according to the synthetic method E. The product was purified by flash chromatography (eluent: AcOEt/Heptane:3/7) to afford a yellow oil which crystallized. Yield: 58%. $^1$H NMR (DMSO-d6): δ 0.83 (t, J=6.9 Hz, 3H), 1.26 (m, 6H), 1.59-1.62 (m, 2H), 3.73 (t, J=6.9 Hz, 2H), 7.17-7.23 (m, 2H), 7.48 (t, J=7.2 Hz, 1H), 7.63-7.70 (m, 3H), 7.90 (d, J=6.6 Hz, 1H), 8.07 (t, J=6.6 Hz, 1H), 8.19 (d, J=8.7 Hz, 1H), 8.35 (br s, 1H), 13.51 (br s, 1H). $^{13}$C NMR (DMSO-d6): δ 14.29 (CH$_3$), 22.39 (CH$_2$), 26.32 (CH$_2$), 27.34 (CH$_2$), 31.27 (CH$_2$), 39.50 (CH$_2$), 110.61 (CH), 119.61 (C), 121.22 (C), 123.65 (CH), 125.36 (CH), 125.51 (CH), 126.83 (CH), 127.20 (CH), 128.03 (CH), 129.04 (CH), 130.34 (C), 131.26 (C), 132.26 (CH), 133.82 (C), 143.49 (C=N), 161.34 (C=O). HRMS (ES+) calcd for C$_{25}$H$_{26}$N$_3$O$_2$ (M+H$^+$), m/e, 400.2033. found, 400.2020.

EXAMPLE 20

N'-[(3Z)-1-hexyl-2-oxo-1,2-dihydro-3H-indol-3-ylidene]adamantane-1-carbohydrazide

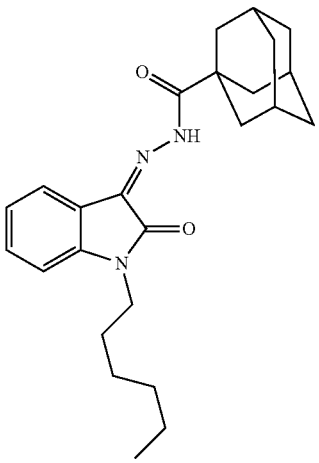 [SMILES: CCCCCCN1C(=O)/C(=N\NC(=O)C23CC4CC(CC(C4)C2)C3)c2ccccc21]

The title compound was prepared as a yellow solid, using isatin 3 and adamantanecarbohydrazide according to the synthetic method E. The resulting solid was washed with ethanol. Yield: 59%. $^1$H NMR (DMSO-d6): δ 0.85 (t, J=6.9 Hz, 3H), 1.27 (m, 6H), 1.60-1.65 (m, 2H), 1.72 (s, 6H), 1.91 (s, 6H), 2.05 (s, 3H), 3.75 (t, J=7.2 Hz, 2H), 7.16 (t, J=7.5 Hz, 1H), 7.21 (d, J=7.8 Hz, 1H), 7.46 (t, J=7.8 Hz, 1H), 7.59 (d, J=7.5 Hz, 1H), 13.28 (br s, 1H). $^{13}$C NMR (DMSO-d6): δ 14.32 (CH$_3$), 22.44 (CH$_2$), 26.38 (CH$_2$), 27.41 (CH$_2$), 27.85 (CH), 31.31 (CH$_2$), 36.32 (CH), 38.80 (CH$_2$), 39.52 (CH$_2$), 110.59 (CH), 119.75 (C), 121.03 (CH), 123.61 (CH), 131.96 (CH), 143.27 (C=N), 161.39 (C=O). HRMS (ES+) calcd for C$_{25}$H$_{34}$N$_3$O$_2$ (M+H$^+$), m/e, 408.2660. found, 408.2646.

EXAMPLE 21

N'-[(3Z)-1-(1-propyl)-2-oxo-1,2-dihydro-3H-indol-3-ylidene]benzohydrazide

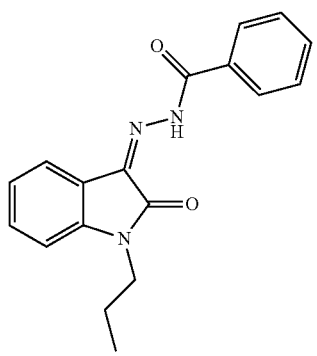 [SMILES: CCCN1C(=O)/C(=N\NC(=O)c2ccccc2)c2ccccc21]

The title compound was prepared as a yellow solid, using isatin 4 and benzhydrazide according to the synthetic method E. Yield: 86%. $^1$H NMR (DMSO-d6): δ 0.92 (t, J=7.5 Hz, 3H), 1.68 (dt, J=7.5 Hz, 2H), 3.75 (t, J=7.0 Hz, 2H), 7.19 (t, J=7.5 Hz, 1H), 7.25 (d, J=8.0 Hz, 1H), 7.49 (t, J=8.0 Hz, 1H), 7.62-7.67 (m, 3H), 7.71 (t, J=7.5 Hz, 1H), 7.92 (d, J=7.5 Hz, 2H), 13.93 (br s, 1H). $^{13}$C NMR (DMSO-d6): δ 11.67 (CH$_3$), 20.89 (CH$_2$), 41.32 (CH$_2$), 110.74 (CH), 119.64 (C), 121.27 (CH), 123.70 (CH), 127.89 (CH), 129.69 (CH), 132.24 (CH), 132.44 (C), 133.41 (CH), 143.54 (C=N), 161.71 (C=O). HRMS (ES+) calcd for C$_{18}$H$_{18}$N$_3$O$_2$ (M+H$^+$), m/e, 308.1397. found, 308.1394.

EXAMPLE 22

N'-[(3Z)-1-(1-butyl)-2-oxo-1,2-dihydro-3H-indol-3-ylidene]benzohydrazide

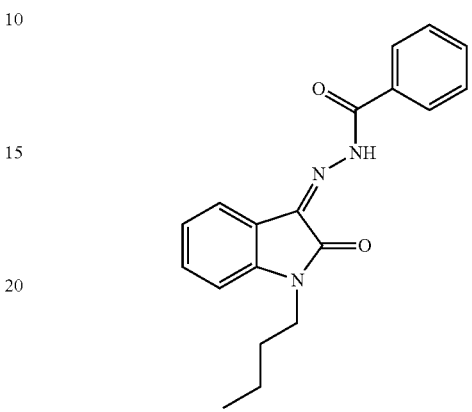

The title compound was prepared as a yellow solid, using isatin 5 and benzhydrazide according to the synthetic method D. The resulting solid was washed with ethanol. Yield: 65.3%. $^1$H NMR (DMSO-d6): δ 0.95 (t, J=7.5 Hz, 3H), 1.36-1.41 (m, 2H), 1.64-1.69 (m, 2H), 3.78 (t, J=7.2 Hz, 2H), 7.19 (t, Hz, J=7.5 Hz, 1H), 7.24 (d, J=7.8 Hz, 1H), 7.49 (td, J=1.2 Hz, J=7.8 Hz, 1H), 7.60-7.73 (m, 4H), 7.90-7.92 (m, 2H), 13.90 (br s, 1H). $^{13}$C NMR (DMSO-d6): δ 14.06 (CH$_3$), 20.04 (CH$_2$), 29.56 (CH$_2$), 39.49 (CH$_2$), 110.69 (CH), 119.66 (C), 121.26 (CH), 123.69 (CH), 127.88 (CH), 129.67 (CH), 132.22 (CH), 132.43 (C), 133.40 (CH), 137.40 (C), 143.43 (C=N), 161.58 (C=O), 163.34 (C=O). HRMS (ES+) calcd for C$_{19}$H$_{20}$N$_3$O$_2$ (M+H$^+$), m/e, 322.1548. found, 322.1550.

EXAMPLE 23

N'-[(3Z)-1-(1-pentyl)-2-oxo-1,2-dihydro-3H-indol-3-ylidene]benzohydrazide

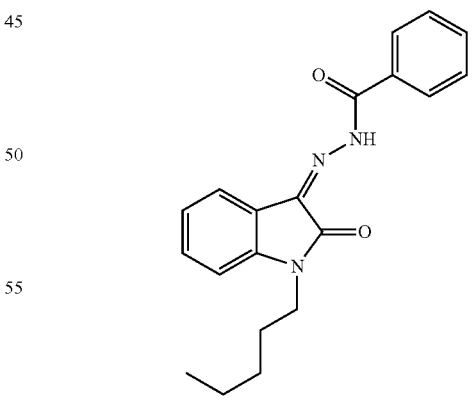

The title compound was prepared as a yellow solid, using isatin 6 and benzhydrazide according to the synthetic method D. The resulting solid was washed with ethanol. Yield: 78.1%. $^1$H NMR (DMSO-d6): δ 0.90 (t, J=6.5 Hz, 3H), 1.34-1.36 (m, 4H), 1.63-1.68 (m, 2H), 3.80 (t, J=7 Hz, 2H), 7.22 (t, Hz, J=7.5 Hz, 1H), 7.26 (d, J=7.5 Hz, 1H), 7.52 (t, J=7.5 Hz, 1H), 7.65-7.70 (m, 3H), 7.74 (t, Hz, J=7 Hz, 1H), 7.96 (d, (d, J=7, 2H), 13.95 (br s, 1H). $^{13}$C NMR (DMSO-d6): δ 14.30 (CH$_3$), 22.27 (CH$_2$), 27.15 (CH$_2$), 28.89 (CH$_2$), 39.75 (CH$_2$), 110.66 (CH), 119.65 (C), 121.26 (CH), 123.69 (CH), 127.88 (CH), 129.67 (CH), 132.23 (CH), 132.42 (C), 133.40 (CH), 137.80 (C), 143.43 (C=N), 161.58 (C=O), 163.36 (C=O). HRMS (ES+) calcd for C$_{20}$H$_{22}$N$_3$O$_2$ (M+H$^+$), m/e, 336.1713. found, 336.1707.

EXAMPLE 24

N'-[(3Z)-1-(1-dodecyl)-2-oxo-1,2-dihydro-3H-indol-3-ylidene]benzohydrazide

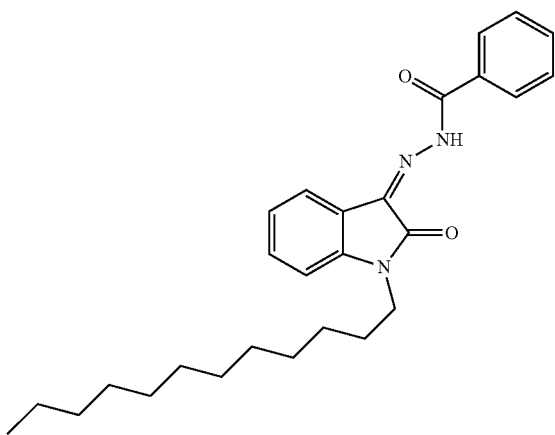 [SMILES: CCCCCCCCCCCCN1C(=O)/C(=N\NC(=O)c2ccccc2)c2ccccc21]

The title compound was prepared as a pale orange solid, using 1-dodecyl-isatin and benzhydrazide according to the synthetic method D. The resulting solid was washed with ethanol. Yield: 100%. $^1$H NMR (DMSO-d6): δ 0.82 (t, J=6.6 Hz, 3H), 1.20-1.28 (m, 18H), 1.62-1.66 (m, 2H), 3.77 (t, J=6.9 Hz, 2H), 7.16-7.24 (m, 2H), 7.48 (t, J=7.5 Hz, 1H), 7.60-7.73 (m, 4H), 7.92 (d, J=7.8 Hz, 2H), 13.91 (br s, 1H). $^{13}$C NMR (DMSO-d6): δ 14.38 (CH$_3$), 22.53 (CH$_2$), 26.67 (CH$_2$), 27.38 (CH$_2$), 29.07 (CH$_2$), 29.14 (CH$_2$), 29.32 (CH$_2$), 39.36 (CH$_2$), 29.43 (CH$_2$), 29.45 (CH$_2$), 31.73 (CH$_2$), 39.75 (CH$_2$), 110.68 (CH), 119.65 (C), 121.27 (CH), 123.70 (CH), 127.88 (CH), 129.65 (CH), 132.22 (CH), 132.41 (C), 133.40 (CH), 143.44 (C=N), 161.61 (C=O). HRMS (ES+) calcd for C$_{27}$H$_{36}$N$_3$O$_2$ (M+H$^+$), m/e, 434.2812. found, 434.2802.

EXAMPLE 25

N'-[(3Z)-1-(cyclohexylmethyl)-2-oxo-1,2-dihydro-3H-indol-3-ylidene]benzohydrazide

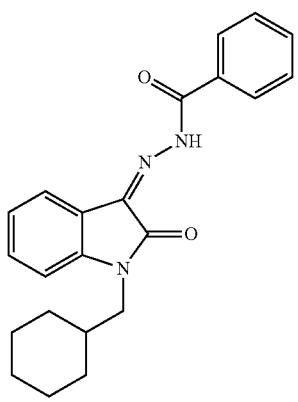 [SMILES: O=C(N/N=C1\C(=O)N(CC2CCCCC2)c2ccccc21)c1ccccc1]

The title compound was prepared as a yellow solid, using isatin 7 and benzhydrazide according to the synthetic method D. The resulting solid was washed with ethanol. Yield: 71.4%. $^1$H NMR (DMSO-d6): δ 1.05-1.09 (m, 2H), 1.18-1.20 (m, 3H), 1.61-1.79 (m, 6H), 3.65 (d, J=7.5 Hz, 2H), 7.22 (t, J=8 Hz, 1H), 7.28 (d, J=8 Hz, 1H), 7.52 (t, J=7.5 Hz, 1H), 7.66-7.70 (m, 3H), 7.75 (t, J=7 Hz, 1H), 7.96 (d, J=7 Hz, 2H), 13.97 (br s, 1H). $^{13}$C NMR (DMSO-d6): δ 25.68 (CH$_2$), 26.26 (CH$_2$), 30.71 (CH$_2$), 36.40 (CH), 45.90 (CH$_2$), 110.95 (CH), 119.57 (C), 121.19 (CH), 123.67 (CH), 127.87 (CH), 129.68 (CH), 132.19 (CH), 132.44 (C), 133.40 (CH), 137.70 (C), 143.94 (C=N), 161.90 (C=O), 163.42 (C=O). HRMS (ES+) calcd for C$_{22}$H$_{24}$N$_3$O$_2$ (M+H$^+$), m/e, 362.1872. found, 362.1863.

EXAMPLE 26

N'-[(3Z)-1-(4-chlorobenzyl)-2-oxo-1,2-dihydro-3H-indol-3-ylidene]benzohydrazide

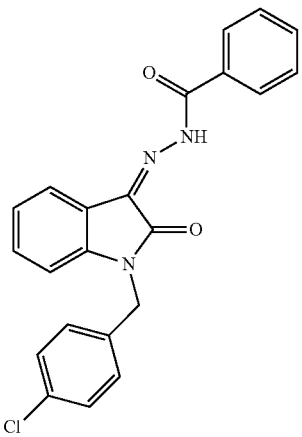 [SMILES: O=C(N/N=C1\C(=O)N(Cc2ccc(Cl)cc2)c2ccccc21)c1ccccc1]

The title compound was prepared as a yellow solid, using 1-(4-chlorobenzyl)-isatin and benzhydrazide according to the synthetic method D. The resulting solid was purified by crystallization in ethyl alcohol. Yield: 86%. $^1$H NMR (DMSO-d6): δ 5.03 (s, 2H), 7.08 (d, J=7.8 Hz, 1H), 7.18 (t, J=7.5 Hz, 1H), 7.39-7.47 (m, 5H), 7.60-7.74 (m, 4H), 7.94 (m, 2H), 13.84 (br s, 1H). $^{13}$C NMR (DMSO-d6): δ 42.43 (CH$_2$), 110.97 (CH), 119.87 (C), 121.35 (CH), 123.99 (CH), 127.93 (CH), 129.15 (CH), 129.70 (CH), 129.88 (CH), 132.14 (CH), 132.45 (C), 132.78 (C), 133.44 (CH), 135.15 (C), 143.04 (C=N), 161.74 (C=O). HRMS (ES+) calcd for C$_{22}$H$_{17}$N$_3$O$_2$Cl (M+H$^+$), m/e, 390.1018. found, 390.1004.

EXAMPLE 27

N'-{[3Z]-1-[2-(1,3-dioxo-1,3-dihydro-2H-isoindol-2-yl)ethyl]-2-oxo-1,2-dihydro-3H-indol-3-ylidene}benzohydrazide

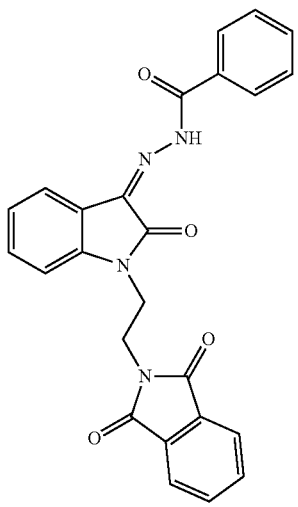 [SMILES: O=C(N/N=C1\C(=O)N(CCN2C(=O)c3ccccc3C2=O)c2ccccc21)c1ccccc1]

The title compound was prepared as a yellow solid, using isatin 9 and benzhydrazide according to the synthetic method D. The resulting solid was washed with ethanol. Yield: 82.6%. $^1$H NMR (DMSO-d6): δ 3.91 (t, J=5.5 Hz, 2H), 4.09 (t, J=5.5 Hz, 2H), 7.18 (t, J=8 Hz, 1H), 7.27 (d, J=8 Hz, 1H), 7.46 (t, J=8 Hz, 1H), 7.55 (t, J=7.5 Hz, 2H), 7.65 (d, J=7.5 Hz, 2H), 7.69 (t, J=7.5 Hz, 2H), 7.76-7.78 (m, 2H), 7.83-7.86 (m, 2H), 13.59 (br s, 1H). $^{13}$C NMR (CDCl$_3$): δ 35.69 (CH$_2$), 38.35 (CH$_2$), 110.27 (CH), 119.64 (C), 121.41 (CH), 123.52 (CH), 123.96 (CH), 127.71 (CH), 129.65 (CH), 131.98 (C), 132.23 (CH), 132.27 (C), 133.44 (CH), 134.93 (CH), 143.01 (C=N), 162.12 (C=O), 168.31 (C=O). HRMS (ES+) calcd for C$_{25}$H$_{19}$N$_4$O$_4$ (M+H$^+$), m/e, 439.1404. found, 439.1401.

EXAMPLE 28

N'-[(3Z)-1-hexyl-7-methyl-2-oxo-1,2-dihydro-3H-indol-3-ylidene]benzohydrazide

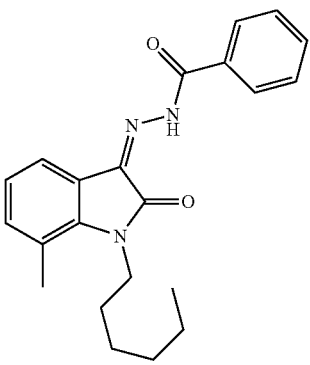 [SMILES: CCCCCCN1C(=O)/C(=N\NC(=O)c2ccccc2)c2cccc(C)c21]

The title compound was prepared as a yellow solid, using isatin 10 and benzhydrazide according to the synthetic method D. The resulting solid was purified by crystallization in ethyl alcohol. Yield: 80%. $^1$H NMR (DMSO-d6): δ 0.87 (t, J=6.5 Hz, 3H), 1.29 to 1.36 (m, 6H), 1.61-1.67 (m, 2H), 3.92 (t, J=8 Hz, 2H), 7.09 (t, J=7.5 Hz, 1H), 7.26 (d, J=7.5 Hz, 1H), 7.52 (d, J=7.0 Hz, 1H), 7.63 (t, J=7.5 Hz, 2H), 7.71 (t, J=7.5 Hz, 1H), 7.92 (d, J=7.5 Hz, 2H), 13.92 (br s, 1H). $^{13}$C NMR (DMSO-d6): δ 14.33 (CH$_3$), 18.57 (CH$_3$), 22.46 (CH$_2$), 26.30 (CH$_2$), 29.55 (CH$_2$), 31.28 (CH$_2$), 41.46 (CH$_2$), 119.21 (CH), 120.60 (C), 121.34 (C), 123.78 (CH), 127.90 (CH), 129.68 (CH), 132.46 (C), 133.40 (CH), 136.12 (CH), 141.05 (C=N), 162.21 (C=O). HRMS (ES+) calcd for C$_{22}$H$_{26}$N$_3$O$_2$ (M+H$^+$), m/e, 364.2028. found, 364.2020.

EXAMPLE 29

N'-[(3Z)-7-chloro-1-hexyl-2-oxo-1,2-dihydro-3H-indol-3-ylidene]benzohydrazide

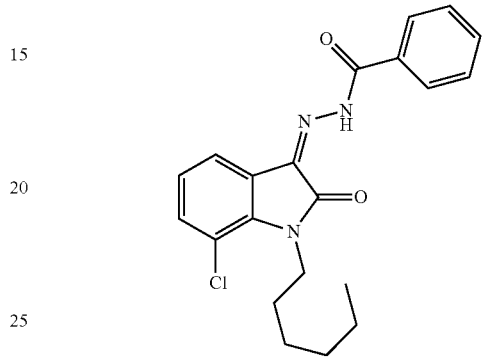

The title compound was prepared as a yellow solid, using isatin 11 and benzhydrazide according to the synthetic method D. The resulting solid was purified by crystallization in ethyl alcohol. Yield: 73%. $^1$H NMR (DMSO-d6): δ 0.87 (t, J=6.5 Hz, 3H), 1.30 to 1.37 (m, 6H), 1.68-1.71 (m, 2H), 4.05 (t, J=7.0 Hz, 2H), 7.20 (t, J=7.5 Hz, 1H), 7.51 (d, J=8.0 Hz, 1H), 7.63-7.66 (m, 3H), 7.73 (t, J=7.0 Hz, 1H), 7.93 (d, J=7.5 Hz, 2H), 13.81 (br s, 1H). $^{13}$C NMR (DMSO-d6): δ 14.33 (CH$_3$), 22.43 (CH$_2$), 26.17 (CH$_2$), 29.54 (CH$_2$), 31.30 (CH$_2$), 41.39 (CH$_2$), 111.92 (C), 115.65 (C), 117.16 (C), 120.17 (CH), 123.10 (C), 125.05 (CH), 127.90 (CH), 127.97 (CH), 129.74 (CH), 132.25 (C), 133.58 (CH), 133.98 (CH), 138.73 (C=N), 161.88 (C=O). HRMS (ES+) calcd for C$_{21}$H$_{23}$N$_3$O$_2$Cl (M+H$^+$), m/e, 384.1473. found, 384.1473.

EXAMPLE 30

N'-[(3Z)-1-hexyl-7-iodo-2-oxo-1,2-dihydro-3H-indol-3-ylidene]benzohydrazide

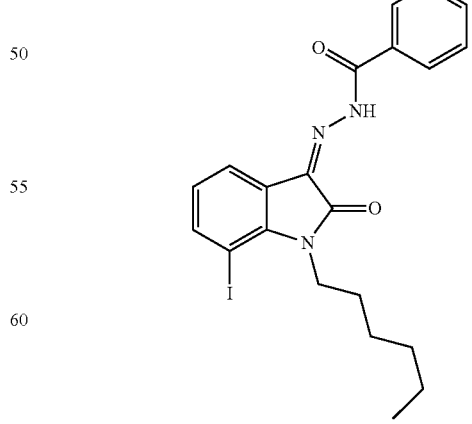

The title compound was prepared as a yellow solid, using isatin 12 and benzhydrazide according to the synthetic method D. The resulting solid was washed with ethanol.

Yield: 68.6%. $^{1}$H NMR (DMSO-d6): δ 0.89 (t, J=7 Hz, 3H), 1.33 to 1.40 (m, 6H), 1.67-1.71 (m, 2H), 4.11 (t, J=8 Hz, 2H), 6.92 (t, J=8 Hz, 1H), 7.61 (t, J=8 Hz, 2H), 7.69 (t, J=7.5 Hz, 2H), 7.87 (d, J=8 Hz, 1H), 7.93 (d, J=7.5 Hz, 2H), 13.85 (br s, 1H). $^{13}$C NMR (DMSO-d6): δ 14.30 (CH$_3$), 22.50 (CH$_2$), 25.94 (CH$_2$), 29.60 (CH$_2$), 31.39 (CH$_2$), 39.57 (CH$_2$), 74.19 (C), 120.93 (CH), 122.90 (C), 125.36 (CH), 127.92 (CH), 129.50 (CH), 132.22 (C), 133.34 (CH), 143.07 (C=N), 144.23 (CH), 162.21 (C=O). HRMS (ES+) calcd for C$_2$H$_{22}$IN$_3$O$_2$ (M+H$^+$), m/e, 476.0848. found, 476.0830.

EXAMPLE 31

N'-[(3Z)-1-hexyl-5-methyl-2-oxo-1,2-dihydro-3H-indol-3-ylidene]benzohydrazide

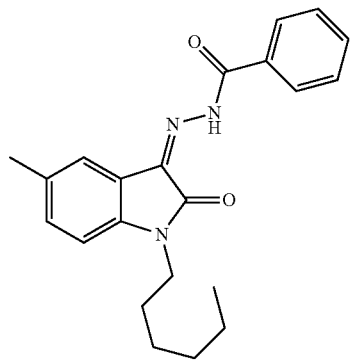 [SMILES: CCCCCCN1C(=O)/C(=N\NC(=O)c2ccccc2)c2cc(C)ccc21]

The title compound was prepared as a yellow solid, using isatin 14 and benzhydrazide according to the synthetic method E. The resulting solid was washed with ethanol. Yield: 91%. $^{1}$H NMR (DMSO-d6): δ 0.84 (t, J=7.0 Hz, 3H), 1.25 to 1.32 (m, 6H), 1.60-1.63 (m, 2H), 3.72 (t, J=7.0 Hz, 2H), 7.09 (d, J=8.0 Hz, 1H), 7.26 (d, J=8.0 Hz, 1H), 7.46 (s, 1H), 7.61-7.63 (m, 2H), 7.92 (d, J=7.5 Hz, 1H), 13.90 (br s, 1H). $^{13}$C NMR (DMSO-d6): δ 14.33 (CH$_3$), 20.94 (CH$_3$), 22.44 (CH$_2$), 26.38 (CH$_2$), 27.41 (CH$_2$), 31.33 (CH$_2$), 39.75 (CH$_2$), 110.45 (CH), 119.61 (C), 121.68 (CH), 127.86 (CH), 129.65 (CH), 132.45 (C), 132.56 (CH), 132.91 (C), 133.36 (CH), 141.24 (C=N), 161.57 (C=O). HRMS (ES+) calcd for C$_{22}$H$_{26}$N$_3$O$_2$ (M+H$^+$), m/e, 364.2024. found, 364.2020.

EXAMPLE 32

N'-[(3Z)-1-hexyl-5-methoxy-2-oxo-1,2-dihydro-3H-indol-3-ylidene]benzohydrazide

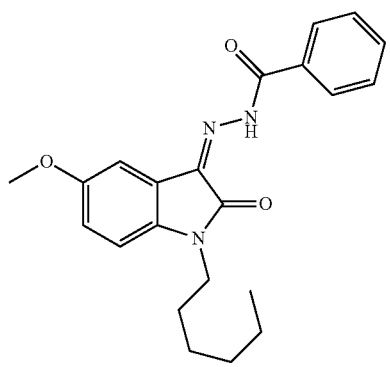 [SMILES: CCCCCCN1C(=O)/C(=N\NC(=O)c2ccccc2)c2cc(OC)ccc21]

The title compound was prepared as a yellow solid, using isatin 15 and benzhydrazide according to the synthetic method E. The resulting solid was washed with ethanol. Yield: 62%. $^{1}$H NMR (DMSO-d6): δ 0.85 (t, J=7.0 Hz, 3H), 1.26 to 1.31 (m, 6H), 1.61-1.64 (m, 2H), 3.73 (t, J=7.0 Hz, 2H), 3.81 (s, 3H), 7.05 (dd, J=2.5, J=8.5 Hz, 1H), 7.15 (d, J=8.5 Hz, 1H), 7.19 (s, 1H), 7.61-7.65 (m, 2H), 7.71 (t, J=7.0 Hz, 1H), 7.92 (d, J=7.5 Hz, 1H), 13.97 (br s, 1H). $^{13}$C NMR (DMSO-d6): δ 14.34 (CH$_3$), 22.43 (CH$_2$), 26.37 (CH$_2$), 27.40 (CH$_2$), 31.33 (CH$_2$), 39.50 (CH$_2$), 56.19 (CH$_3$), 106.49 (CH), 111.63 (CH), 118.09 (CH), 120.48 (C), 127.87 (CH), 129.68 (CH), 132.41 (C), 133.43 (CH), 137.13 (C), 156.34 (C=N), 161.55 (C=O). HRMS (ES+) calcd for C$_{22}$H$_{26}$N$_3$O$_3$ (M+H$^+$), m/e, 380.1977. found, 380.1969.

EXAMPLE 33

N'-[(3Z)-5-fluoro-1-hexyl-2-oxo-1,2-dihydro-3H-indol-3-ylidene]benzohydrazide

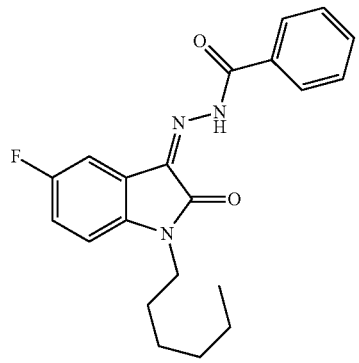 [SMILES: CCCCCCN1C(=O)/C(=N\NC(=O)c2ccccc2)c2cc(F)ccc21]

The title compound was prepared as a yellow solid, using isatin 16 and benzhydrazide according to the synthetic method E. The resulting solid was washed with ethanol. Yield: 61.3%. $^{1}$H NMR (DMSO-d6): δ 0.85 (t, J=6.6 Hz, 3H), 1.25 to 1.30 (m, 6H), 1.58-1.65 (m, 2H), 3.75 (t, J=7.0 Hz, 2H), 7.24 (dd, J=4 Hz, J=9 Hz, 1H), 7.31 (td, J=2.5 Hz, J=9 Hz, 1H), 7.45 (dd, J=2 Hz, J=7.5 Hz, 1H), 7.61-7.64 (m, 2H), 7.71 (t, J=7.5 Hz, 1H), 7.90 (d, J=2 Hz, J=7.5 Hz, 2H), 13.89 (br s, 1H). $^{13}$C NMR (DMSO-d6): δ 14.33 (CH$_3$), 22.44 (CH$_2$), 26.36 (CH$_2$), 27.34 (CH$_2$), 31.33 (CH$_2$), 39.89 (CH$_2$), 108.52 (d, J=100 Hz, CH), 111.91 (d, J=30 Hz, CH), 121.25 (d, J=95 Hz, CH), 120.98 (d, J=35 Hz, C), 127.93 (CH), 129.68 (CH), 132.24 (C), 133.50 (CH), 137.28 (C), 139.66 (C=N), 159.20 (d, J=950 Hz, CF), 161.59 (C=O), 163.34 (C=O). HRMS (ES+) calcd for C$_{21}$H$_{23}$FN$_3$O (M+H$^+$), m/e, 368.1778. found, 368.1769.

EXAMPLE 34

N'-[(3Z)-5-chloro-1-hexyl-2-oxo-1,2-dihydro-3H-indol-3-ylidene]benzohydrazide

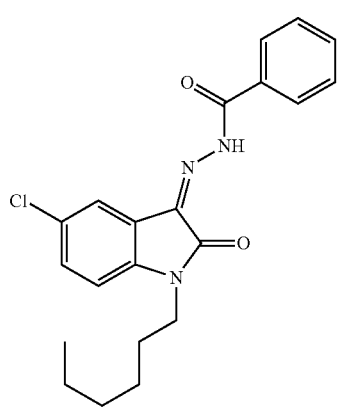 [SMILES: CCCCCCN1C(=O)/C(=N\NC(=O)c2ccccc2)c2cc(Cl)ccc21]

The title compound was prepared as a yellow solid, using isatin 17 and benzhydrazide according to the synthetic method E. The resulting solid was washed with ethanol. Yield: 13.5%. $^{1}$H NMR (DMSO): δ 0.90 (t, J=6.5 Hz, 3H), 1.32 (br s, 6H), 1.62-1.64 (m, 2H), 3.78 (t, J=7 Hz, 2H), 7.25 (d, J=8.5 Hz, 1H), 7.60 (dd, J=1.5 Hz, J=8 Hz, 1H), 7.63-7.68 (m, 2H), 7.72 (t, J=7 Hz, 1H), 8.01 (d, J=7.5 Hz, 1H), 8.164 (s, 1H), 11.92 (s, 1H). $^{13}$C NMR (CDCl$_3$): δ 14.34 (CH$_3$), 22.47 (CH$_2$), 26.32 (CH$_2$), 27.28 (CH$_2$), 31.32 (CH$_2$), 39.50 (CH$_2$), 111.34 (CH), 116.57 (C), 126.57 (C), 126.79 (CH), 128.99 (CH), 129.19 (CH), 132.42 (CH), 132.86 (CH), 133.32 (C), 139.01 (C), 143.48 (C=N), 163.54 (C=O), 167.36 (C=O). HRMS (ES+) calcd for C$_{21}$H$_{23}$ClN$_3$O$_2$ (M+H$^+$), m/e, 384.1480. found, 384.1473.

EXAMPLE 35

N'-[(3Z)-5-iodo-2-oxo-1-pentyl-1,2-dihydro-3H-indol-3-ylidene]benzohydrazide

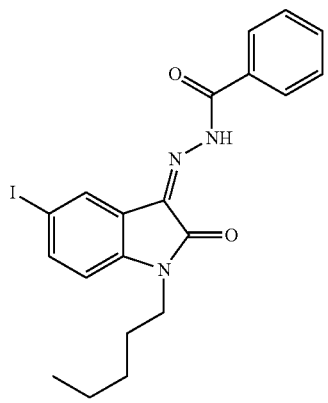 [SMILES: CCCCCN1C(=O)/C(=N\NC(=O)c2ccccc2)c2cc(I)ccc21]

The title compound was prepared as a yellow solid, using isatin 8 and benzhydrazide according to the synthetic method D. The resulting solid was washed with ethanol. Yield: 70.2%. $^1$H NMR (DMSO-d6): δ 0.91 (t, J=6.5 Hz, 3H), 1.35 to 1.36 (m, 4H), 1.66-1.69 (m, 2H), 3.80 (t, J=7 Hz, 2H), 7.15 (d, J=8.5 Hz, 1H), 7.69 (t, J=7.5 Hz, 2H), 7.77 (t, J=7 Hz, 1H), 7.86 (dd, J=1.5 Hz, J=8.5 Hz, 1H), 7.91 (s, 1H), 7.97 (d, J=7 Hz, 2H), 13.87 (br s, 1H). $^{13}$C NMR (DMSO-d6): δ 14.30 (CH$_3$), 22.27 (CH$_2$), 27.08 (CH$_2$), 28.83 (CH$_2$), 39.85 (CH$_2$), 86.79 (C), 113.11 (CH), 121.98 (C), 127.96 (CH), 129.01 (CH), 129.70 (CH), 132.25 (C), 133.53 (CH), 136.53 (C), 140.14 (CH), 142.99 (C=N), 161.05 (C=O), 163.61 (C=O). HRMS (ES+) calcd for C$_{20}$H$_{21}$IN$_3$O$_2$ (M+H$^+$), m/e, 462.0672. found, 462.0673.

EXAMPLE 36

N'-[(3Z)-1-hexyl-6-methoxy-2-oxo-1,2-dihydro-3H-indol-3-ylidene]benzohydrazide

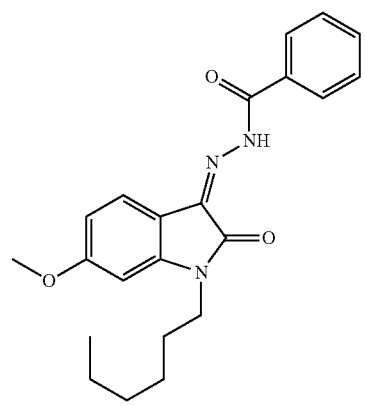 [SMILES: CCCCCCN1C(=O)/C(=N\NC(=O)c2ccccc2)c2ccc(OC)cc21]

A) 1-hexyl-6-methoxy-isatin

The title compound was prepared as a red solid, using 6-methoxy-isatin prepared as described by Pavlidis et al. and bromohexane following Method B. Pavlidis, V. H., et al., *The Synthesis of a Novel Series of Substituted 2-Phenyl-4H-3,1-benzoxazin-4-ones*, Synthetic Communications, 1994, 24(4): 533-548.

B) N'-[(3Z)-1-hexyl-6-methoxy-2-oxo-1,2-dihydro-3H-indol-3-ylidene]benzohydrazide The title compound was prepared as a yellow solid, using 1-hexyl-6-methoxy-isatin and benzhydrazide according to the synthetic method E. NMR (CDCl$_3$): δ 0.88 (t, 3H), 1.28 to 1.39 (m, 6H), 1.68-1.74 (m, 2H), 3.73 (t, 2H), 3.87 (s, 3H), 6.44 (d, 1H), 6.64 (dd, 1H), 7.51 (t, 2H), 7.59 (t, 1H), 7.80 (d, 1H), 8.00 (d, 1H), 13.98 (br s, 1H).

EXAMPLE 37

N'-[(3Z)-1-(cyclohexylmethyl)-6-methoxy-2-oxo-1,2-dihydro-3H-indol-3-ylidene]benzohydrazide

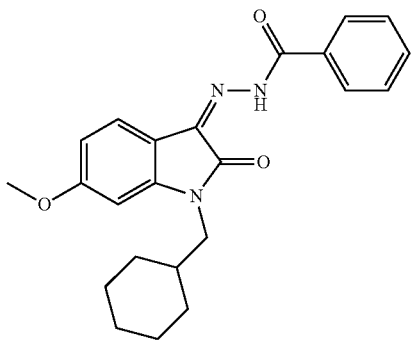 [SMILES: COc1ccc2c(c1)N(CC1CCCCC1)C(=O)/C2=N\NC(=O)c1ccccc1]

A) 1-cyclohexylmethyl-6-methoxy-isatin

The title compound was prepared as a red solid, using 6-methoxy-isatin prepared as described by Pavlidis et al. and (Bromomethyl)cyclohexane following Method B. Pavlidis, V. H., et al., *The Synthesis of a Novel Series of Substituted 2-Phenyl-4H-3,1-benzoxazin-4-ones*, Synthetic Communications, 1994, 24:4, 533-548.

B) N'-[(3Z)-1-(cyclohexylmethyl)-6-methoxy-2-oxo-1,2-dihydro-3H-indol-3-ylidene]benzohydrazide The title compound was prepared as a yellow solid, using 1-cyclohexylmethyl-6-methoxy-isatin and benzhydrazide according to the synthetic method E. NMR (CDCl$_3$-d6): δ 1.01-1.09 (m, 2H), 1.16 to 1.26 (m, 3H), 1.68-1.86 (m, 6H), 3.56 (d, 2H), 6.44 (d, 1H), 6.64 (dd, 1H), 7.51 (t, 2H), 7.58 (t, 1H), 7.80 (d, 1H), 8.01 (d, 2H), 13.98 (br s, 1H).

EXAMPLE 38

N'-[(3Z)-1-benzyl-6-methoxy-2-oxo-1,2-dihydro-3H-indol-3-ylidene]benzohydrazide

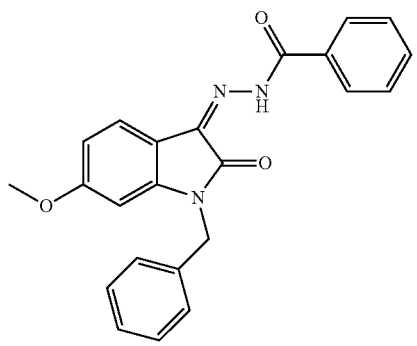 [SMILES: COc1ccc2c(c1)N(Cc1ccccc1)C(=O)/C2=N\NC(=O)c1ccccc1]

A) 1-benzyl-6-methoxy-isatin

The title compound was prepared as a red solid, using 6-methoxy-isatin prepared as described by Pavlidis et al. and benzyl bromide following Method B. Pavlidis, V. H., et al., *The Synthesis of a Novel Series of Substituted 2-Phenyl-4H-3,1-benzoxazin-4-ones*, Synthetic Communications, 1994, 24:4, 533-548.

B) N'-[(3Z)-1-benzyl-6-methoxy-2-oxo-1,2-dihydro-3H-indol-3-ylidene]benzohydrazide The title compound was prepared as a yellow solid, using 1-benzyl-6-methoxy-isatin and benzhydrazide according to the synthetic method E. $^1$H NMR (CDCl$_3$): δ 3.77 (s, 3H), 4.94 (s, 2H), 6.35 9d, 1H), 6.62 (dd, 1H), 7.29-7.36 (m, 4H), 7.51 (t, 2H), 7.59 (t, 1H), 7.80 (d, 1H), 8.01 (d, 2H), 13.95 (br s, 1H).

EXAMPLE 39

N'-[(3Z)-6-methoxy-1-pentyl-2-oxo-1,2-dihydro-3H-indol-3-ylidene]benzohydrazide

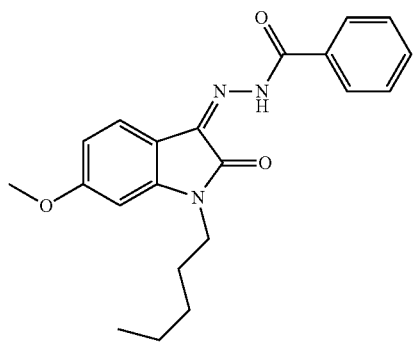 [SMILES: CCCCCN1C(=O)/C(=N\NC(=O)c2ccccc2)c2ccc(OC)cc21]

A) 1-pentyl-6-methoxy-isatin

The title compound was prepared as a red solid, using 6-methoxy-isatin prepared as described in Pavlidis et al. and pentyl bromide following Method B. Pavlidis, V. H., et al., *The Synthesis of a Novel Series of Substituted 2-Phenyl-4H-3,1-benzoxazin-4-ones*, Synthetic Communications, 1994, 24:4, 533-548.

B) N'-[(3Z)-6-methoxy-1-pentyl-2-oxo-1,2-dihydro-3H-indol-3-ylidene]benzohydrazide The title compound was prepared as a yellow solid, using 1-pentyl-6-methoxy-isatin and benzhydrazide according to the synthetic method E. NMR (CDCl$_3$): δ 0.91 (t, 3H), 1.36 to 1.39 (m, 4H), 1.69-1.75 (m, 2H), 3.73 (t, 2H), 3.87 (s, 3H), 6.44 (d, 1H), 6.64 (dd, 1H), 7.51 (t, 2H), 7.59 (t, 1H), 7.80 (d, 1H), 8.00 (d, 1H), 13.98 (br s, 1H).

EXAMPLE 40

N'-[(3Z)-1-butyl-6-methoxy-2-oxo-1,2-dihydro-3H-indol-3-ylidene]benzohydrazide

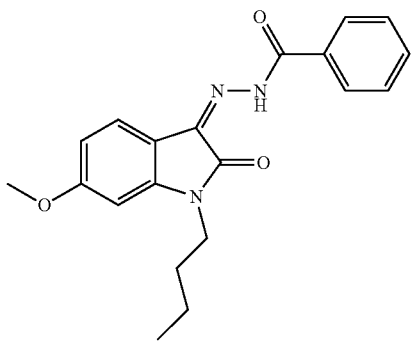 [SMILES: CCCCN1C(=O)/C(=N\NC(=O)c2ccccc2)c2ccc(OC)cc21]

A) 1-butyl-6-methoxy-isatin

The title compound was prepared as a red solid, using 6-methoxy-isatin prepared as described in Pavlidis et al. and bromobutane following Method B. Pavlidis, V. H., et al., *The Synthesis of a Novel Series of Substituted 2-Phenyl-4H-3,1-benzoxazin-4-ones*, Synthetic Communications, 1994, 24:4, 533-548.

B) N'-[(3Z)-1-butyl-6-methoxy-2-oxo-1,2-dihydro-3H-indol-3-ylidene]benzohydrazide The title compound was prepared as a yellow solid, using 1-butyl-6-methoxy-isatin and benzhydrazide according to the synthetic method E. NMR (CDCl$_3$): δ 0.98 (t, 3H), 1.38 to 1.45 (m, 4H), 1.67-1.73 (m, 2H), 3.73 (t, 2H), 3.87 (s, 3H), 6.44 (d, 1H), 6.64 (dd, 1H), 7.51 (t, 2H), 7.59 (t, 1H), 7.80 (d, 1H), 8.00 (d, 1H), 13.97 (br s, 1H).

EXAMPLE 41

N'-[(3Z)-1-(2-cyclohexylethyl)-6-methoxy-2-oxo-1,2-dihydro-3H-indol-3-ylidene]benzohydrazide

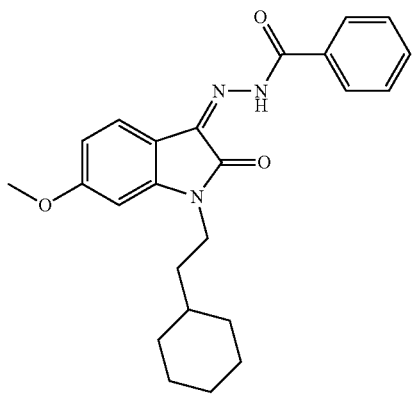 [SMILES: COc1ccc2c(c1)N(CCC1CCCCC1)C(=O)/C2=N\NC(=O)c1ccccc1]

A) 1-(2-cyclohexylethyl)-6-methoxy-isatin

The title compound was prepared as a red solid, using 6-methoxy-isatin prepared as described in Pavlidis et al. and 1-Bromo-2-cyclohexylethane following Method B. Pavlidis, V. H., et al., *The Synthesis of a Novel Series of Substituted 2-Phenyl-4H-3,1-benzoxazin-4-ones*, Synthetic Communications, 1994, 24:4, 533-548.

B) N'-[(3Z)-1-(2-cyclohexylethyl)-6-methoxy-2-oxo-1,2-dihydro-3H-indol-3-ylidene]benzohydrazide The title compound was prepared as a yellow solid, using 1-(2-cyclohexylethyl)-6-methoxy-isatin and benzhydrazide according to the synthetic method E. NMR (CDCl$_3$): δ 0.96-1.04 (m, 2H), 1.15-1.38 (m, 4H), 1.59 (dd, 2H), 1.65-1.75 (m, 3H), 1.81 (d, 2H), 3.74 (t, 2H), 3.87 (s, 3H), 6.43 (d, 1H), 6.64 (dd, 1H), 7.51 (t, 2H), 7.59 (t, 1H), 7.80 (d, 1H), 8.00 (d, 1H), 13.96 (br s, 1H).

EXAMPLE 42

N'-[(3Z)-6-methoxy-1-pentyl-2-oxo-1,2-dihydro-3H-indol-3-ylidene]cyclohexanecarbohydrazide

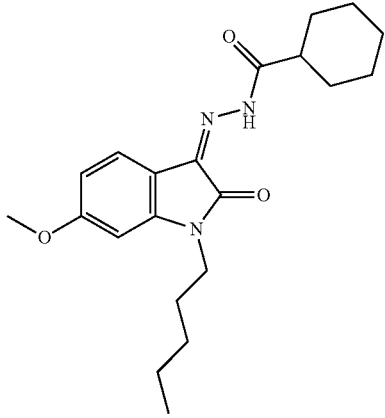 [SMILES: CCCCCN1C(=O)/C(=N\NC(=O)C2CCCCC2)c2ccc(OC)cc21]

The title compound was prepared as a yellow solid, using 1-pentyl-6-methoxy-isatin obtained in Example 39(A) and cyclohexanecarbohydrazide according to the synthetic method E. NMR (CDCl$_3$): δ 0.91 (t, 3H), 1.25 to 2.36 (m, 17H), 3.70 (t, 2H), 3.87 (s, 3H), 6.43 (d, 1H), 6.61 (dd, 1H), 7.51 and 7.73 (d for isomers, 1H), 12.28 and 13.078 (br s for isomers, 1H).

EXAMPLE 43

2-hydroxy-N'-[(3Z)-6-methoxy-1-pentyl-2-oxo-1,2-dihydro-3H-indol-3-ylidene]-2-methylpropanohydrazide

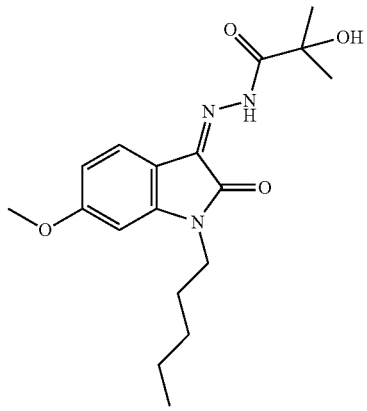 [SMILES: CCCCCN1C(=O)/C(=N\NC(=O)C(C)(C)O)c2ccc(OC)cc21]

The title compound was prepared as a yellow solid, using 1-pentyl-6-methoxy-isatin obtained in Example 39(A) and 2-hydroxy-2-methylpropanohydrazide according to the synthetic method E. NMR (CDCl$_3$): δ 0.91 (t, 3H), 1.36 to 1.39 (m, 4H), 1.59 (s, 6H), 1.87 (m, 3H), 2.63 (s, 1H), 3.68 (t, 2H), 3.87 (s, 3H), 6.41 (d, 1H), 6.61 (dd, 1H), 7.73 (d, 1H), 13.71 (br s, 1H).

EXAMPLE 44 tert-butyl (2Z)-2-(6-methoxy-1-pentyl-2-oxo-1,2-dihydro-3H-indol-3-ylidene)hydrazinecarboxylate

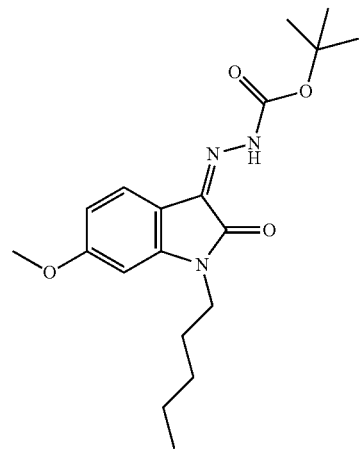 [SMILES: CCCCCN1C(=O)/C(=N\NC(=O)OC(C)(C)C)c2ccc(OC)cc21]

The title compound was prepared as a yellow solid, using 1-pentyl-6-methoxy-isatin obtained in Example 39(A) and tert-Butyl carbazate according to the synthetic method E. NMR (CDCl₃): δ 0.91 (t, 3H), 1.36 to 1.39 (m, 4H), 1.54 9s, 9H), 1.69-1.75 (m, 2H), 3.70 (t, 2H), 3.86 (s, 3H), 6.41 (d, 1H), 6.60 (dd, 1H), 7.66 (d, 1H), 12.201 (br s, 1H).

EXAMPLE 45

N'-[(3Z)-6-methoxy-1-pentyl-2-oxo-1,2-dihydro-3H-indol-3-ylidene]-2-phenylacetohydrazide

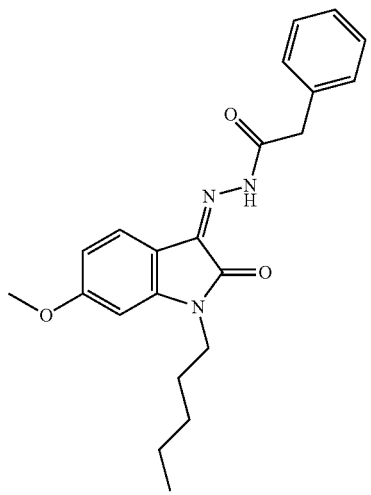 [SMILES: CCCCCN1C(=O)/C(=N\NC(=O)Cc2ccccc2)c2ccc(OC)cc21]

The title compound was prepared as a yellow solid, using 1-pentyl-6-methoxy-isatin obtained in Example 39(A) and Phenylacetic hydrazide according to the synthetic method E. NMR (CDCl₃): δ 0.91 (t, 3H), 1.33 to 1.39 (m, 4H), 1.66-1.69 (m, 2H), 3.62-3.76 (m, 2H), 3.85-3.88 (m, 3H), 4.14 and 4.23 (s for isomers, 1H), 6.38-6.64 (m, 2H), 7.22-7.26 (m 1H), 7.32 (m, 2H), 7.38-7.39 (m, 1H), 7.42 (d, 1H), 7.54 and 7.56 (d for isomers, 1H), 9.25 and 12.44 and 12.99 (br s for isomers, 1H).

EXAMPLE 46

N'-[(3Z)-6-methoxy-1-pentyl-2-oxo-1,2-dihydro-3H-indol-3-ylidene]-3-methylbutanohydrazide

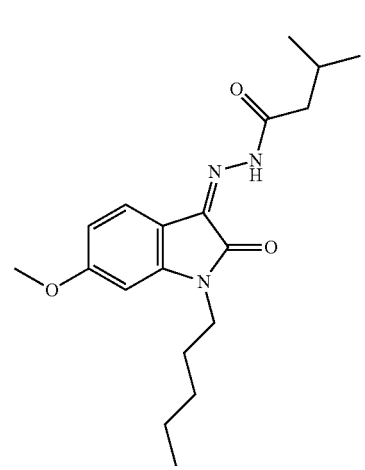 [SMILES: CCCCCN1C(=O)/C(=N\NC(=O)CC(C)C)c2ccc(OC)cc21]

The title compound was prepared as a yellow solid, using 1-pentyl-6-methoxy-isatin obtained in Example 39(A) and 3-methylbutanohydrazide according to the synthetic method E. NMR (CDCl₃): δ 0.92 (t, 3H), 1.05 (d, 6H), 1.36 to 1.39 (m, 4H), 1.69-1.75 (m, 2H), 2.30 (m, 2H), 2.72 (d, 1H), 3.72 (t, 2H), 3.89 (s, 3H), 6.44 (d, 1H), 6.64 (dd, 1H), 7.54 and 7.77 (d for isomers, 1H), 12.41 and 13.03 (br s for isomers, 1H).

EXAMPLE 47

2-cyclohexyl-N'-[(3Z)-6-methoxy-1-pentyl-2-oxo-1,2-dihydro-3H-indol-3-ylidene]acetohydrazide

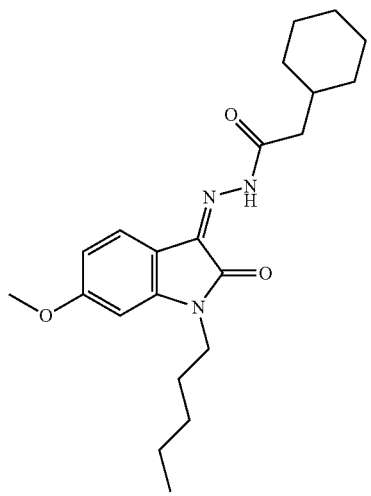 [SMILES: CCCCCN1C(=O)/C(=N\NC(=O)CC2CCCCC2)c2ccc(OC)cc21]

The title compound was prepared as a yellow solid, using 1-pentyl-6-methoxy-isatin obtained in Example 39(A) and 2-cyclohexylacetohydrazide according to the synthetic method E. NMR (CDCl₃): δ 0.91 (t, 3H), 1.01-1.07 (m, 2H), 1.18 to 1.39 (m, 7H), 1.60-1.72 (m, 5H), 1.81 (d, 2H), 1.92-1.94 (m, 1H), 2.27 (d, 1H), 2.69 (d, 1H), 3.70 (t, 2H), 3.87 (s, 3H), 6.42 (s, 1H), 6.62 (d, 1H), 7.52 and 7.74 (d for isomers, 1H), 12.39 and 13.99 (br s for isomers, 1H).

EXAMPLE 48

N'-[(3Z)-6-methoxy-1-pentyl-2-oxo-1,2-dihydro-3H-indol-3-ylidene]-3,3-dimethylbutanohydrazide

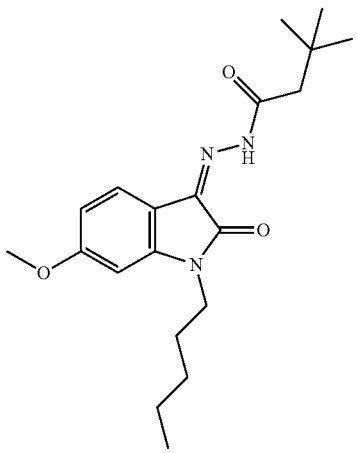 [SMILES: CCCCCN1C(=O)/C(=N\NC(=O)CC(C)(C)C)c2ccc(OC)cc21]

The title compound was prepared as a yellow solid, using 1-pentyl-6-methoxy-isatin obtained in Example 39(A) and 3,3-dimethylbutanohydrazide according to the synthetic method E. NMR (CDCl₃): δ 0.91 (t, 3H), 1.10 and 1.12 (s for isomers, 9H), 1.36 to 1.39 (m, 4H), 1.55 (s, 2H), 1.67-1.70 (m, 2H), 2.29 (s, 1H), 2.75 (s, 1H), 3.70 (t, 2H), 3.86 and 3.87 (s for isomers, 3H), 6.42 (s, 1H), 6.60 (d, 1H), 7.51 and 7.72 (d ans br s for isomers, 1H), 12.39 and 12.98 (s and br s for isomers, 1H).

EXAMPLE 49

N'-[(3Z)-6-methoxy-1-pentyl-2-oxo-1,2-dihydro-3H-indol-3-ylidene]-2-morpholin-4-ylacetohydrazide

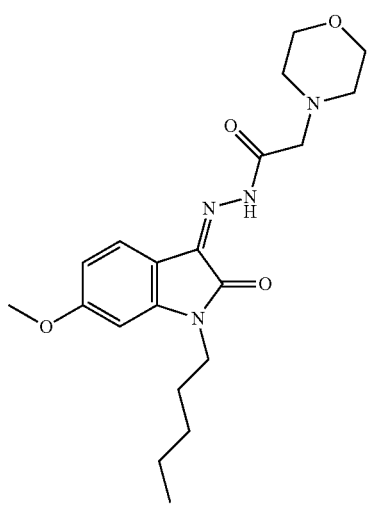 [SMILES: CCCCCN1C(=O)/C(=N\NC(=O)CN2CCOCC2)c2ccc(OC)cc21]

The title compound was prepared as a yellow solid, using 1-pentyl-6-methoxy-isatin obtained in Example 39(A) and 2-morpholin-4-ylacetohydrazide according to the synthetic method E. NMR (CDCl₃): δ 0.92 (t, 3H), 1.26 (s, 1H), 1.36 to 1.39 (m, 5H), 1.64-1.72 (m, 4H), 2.61 (d, 4H), 3.29 (s, 2H), 3.84-3.87 (m, 8H), 6.41 (d, 1H), 6.60 (dd, 1H), 7.75 (d, 2H), 13.86 (br s, 1H).

EXAMPLE 50

N'-[(3Z)-6-methoxy-1-pentyl-2-oxo-1,2-dihydro-3H-indol-3-ylidene]-2,2-dimethylpropanohydrazide

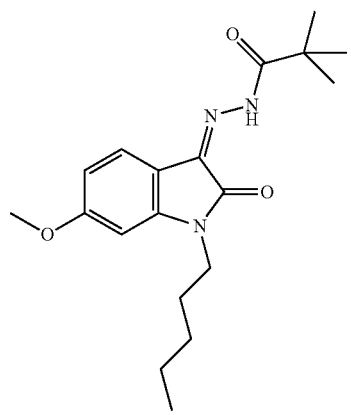 [SMILES: CCCCCN1C(=O)/C(=N\NC(=O)C(C)(C)C)c2ccc(OC)cc21]

The title compound was prepared as a yellow solid, using 1-pentyl-6-methoxy-isatin obtained in Example 39(A) and 2,2-Dimethylpropionic acid hydrazide according to the synthetic method E. NMR (CDCl₃): δ 0.91 (t, 3H), 1.36 to 1.39 (m, 13H), 1.69-1.75 (m, 2H), 3.70 (t, 2H), 3.87 (s, 3H), 6.42 (d, 1H), 6.62 (dd, 1H), 7.74 (d, 2H), 13.34 (br s, 1H).

EXAMPLE 51

N'-[(3Z)-1-hexyl-6-methoxy-2-oxo-1,2-dihydro-3H-indol-3-ylidene]cyclohexanecarbohydrazide

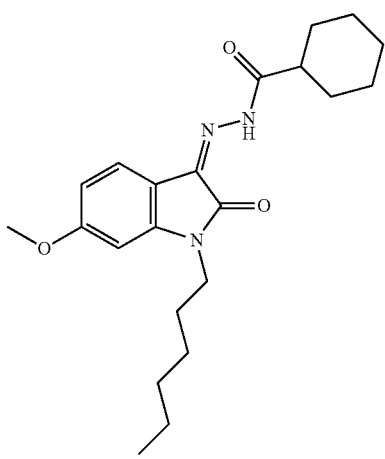 [SMILES: CCCCCCN1C(=O)/C(=N\NC(=O)C2CCCCC2)c2ccc(OC)cc21]

The title compound was prepared as a yellow solid, using 1-pentyl-6-methoxy-isatin obtained in Example 36(A) and cyclohexanecarbohydrazide according to the synthetic method E. NMR (CDCl₃): δ 0.88 (t, 3H), 1.25 to 2.36 (m, 19H), 3.32 (m minor isomer, 0.3; H), 3.70 (t, 2H), 3.87 (s, 3H), 6.42 (s, 1H), 6.61 (d, 1H), 7.52 and 7.73 (d for isomers, 1H), 12.28 and 13.08 (br s for isomers, 1H).

EXAMPLE 52

N'-[(3Z)-1-hexyl-6-methoxy-2-oxo-1,2-dihydro-3H-indol-3-ylidene]-3-methylbutanohydrazide

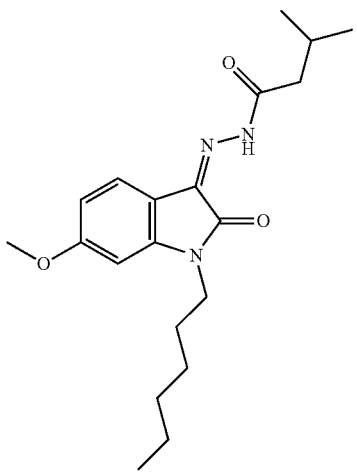 [SMILES: CCCCCCN1C(=O)/C(=N\NC(=O)CC(C)C)c2ccc(OC)cc21]

The title compound was prepared as a yellow solid, using 1-pentyl-6-methoxy-isatin obtained in Example 36(A) and 3-methylbutanohydrazide according to the synthetic method E. NMR (CDCl$_3$): δ 0.92 (t, 3H), 1.05 (d, 6H), 1.36 to 1.39 (m, 6H), 1.69-1.75 (m, 2H), 2.28 (m, 2H), 2.72 (d, 1H), 3.70 (t, 2H), 3.88 (s, 3H), 6.42 (d, 1H), 6.64 (dd, 1H), 7.52 and 7.74 (d for isomers, 1H), 12.39 and 13.00 (br s for isomers, 1H).

EXAMPLE 53

N'-[(3Z)-1-(cyclohexylmethyl)-6-methoxy-2-oxo-1,2-dihydro-3H-indol-3-ylidene]cyclohexanecarbohydrazide

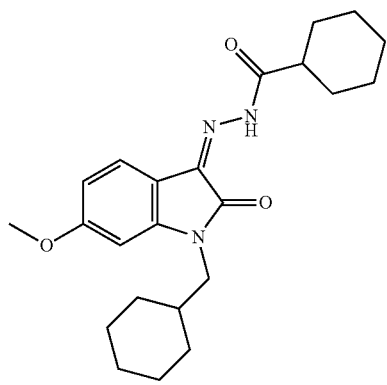 [SMILES: COc1ccc2c(c1)N(CC1CCCCC1)C(=O)/C2=N\NC(=O)C1CCCCC1]

The title compound was prepared as a yellow solid, using 1-pentyl-6-methoxy-isatin obtained in Example 37(A) and cyclohexanecarbohydrazide according to the synthetic method E. NMR (CDCl$_3$): δ 1.03-2.35 (m, 22H), 3.33 (m minor isomer, 0.34; H), 1.05 (d, 6H), 3.53 (d, 2H), 3.87 (s, 3H), 6.42 (d, 1H), 6.62 (dd, 1H), 7.51 and 7.73 (d for isomers, 1H), 12.29 and 13.07 (br s for isomers, 1H).

EXAMPLE 54

N'-[(3Z)-1-(cyclohexylmethyl)-6-methoxy-2-oxo-1,2-dihydro-3H-indol-3-ylidene]-3-methylbutanohydrazide

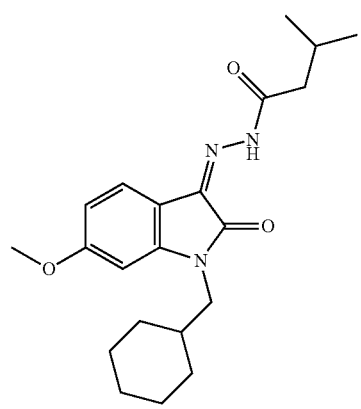 [SMILES: COc1ccc2c(c1)N(CC1CCCCC1)C(=O)/C2=N\NC(=O)CC(C)C]

The title compound was prepared as a yellow solid, using 1-pentyl-6-methoxy-isatin obtained in Example 37(A) and 3-methylbutanohydrazide according to the synthetic method E.

EXAMPLE 55

N'-[(3Z)-6-methoxy-1-(2-methoxyethyl)-2-oxo-L2-dihydro-3H-indol-3-ylidene]benzohydrazide

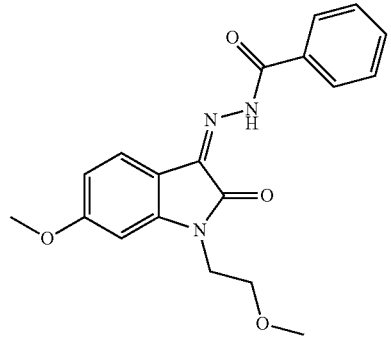 [SMILES: COCCN1C(=O)/C(=N\NC(=O)c2ccccc2)c2ccc(OC)cc21]

A) 6-methoxy-1-(2-methoxyethyl)-isatin

The title compound was prepared as a red solid, using 6-methoxy-isatin prepared as described in Pavlidis et al. and 2-bromoethyl methyl ether following Method B. Pavlidis, V. H., et al., *The Synthesis of a Novel Series of Substituted 2-Phenyl-4H-3,1-benzoxazin-4-ones*, Synthetic Communications, 1994, 24:4, 533-548. NMR (CDCl$_3$): δ 3.35 (s, 3H), 3.65 (t, 2H), 3.87 (s, 3H), 3.94 (t, 2H), 6.64 (d, 1H), 7.58 (t, 1H), 7.79 (d, 1H), 13.93 (br s, 1H).

B) N'-[(3Z)-6-methoxy-1-(2-methoxyethyl)-2-oxo-1,2-dihydro-3H-indol-3-ylidene]benzohydrazide The title compound was prepared as a yellow solid, using 6-methoxy-1-(2-methoxyethyl)-isatin and benzhydrazide according to the synthetic method NMR (CDCl$_3$): δ 3.35 (s, 3H), 3.65 (t, 2H), 3.87 (s, 3H), 3.94 (t, 2H), 6.64 (d, 1H), 7.58 (t, 1H), 7.79 (d, 1H), 13.93 (br s, 1H).

Other compounds useful in connection with the methods described herein:

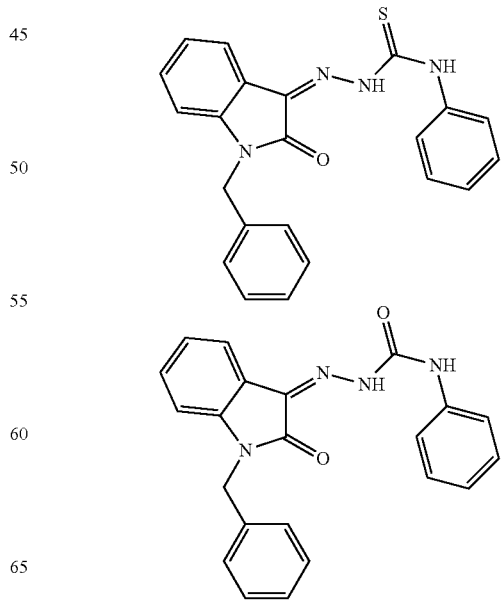

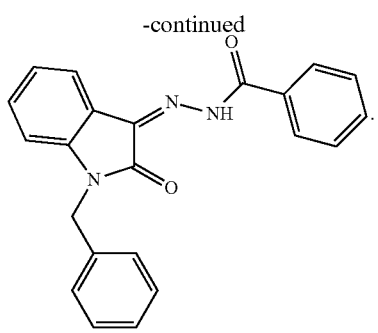

BIOLOGICAL ACTIVITY ASSAY

CB1 Binding Assay

Cell membrane homogenates (25 μg protein) are incubated for 120 min at 37° C. with 0.5 nM [$^3$H]CP 55940 (the reference standard [Rinaldi-Carmona, 1996 #1320]) in the absence or presence of the test compound in a buffer containing 50 mM Tris HCl (pH 7.4), 5 mM MgCl2, 2.5 mM EDTA, and 0.3% bovine serum albumin (BSA).

CB2 Binding Assay

Cell membrane homogenates (15 μg protein) are incubated for 120 min at 37° C. with 0.8 nM [$^3$H]WIN 55212-2 (the reference standard [Munro, 1993 #1321]) in the absence or presence of the test compound in a buffer containing 50 mM HEPES/Tris HCL (pH 7.4), 5 mM MgCl2, 2.5 mM EGTA, and 0.1% BSA. Nonspecific binding is determined in the presence of 10 μM WIN 55212-2. After being incubated, the samples are filtered rapidly under vacuum through glass fiber filters (GF/B; Packard) presoaked with 0.3% PEI and rinsed several times with ice-cold buffer containing 50 mM Tris HCl (pH 7.4) and 0.5% BSA using a 96-sample cell harvester (Unifilter; Packard). The filters are dried then counted for radioactivity in a scintillation counter (Topcount; Packard) using a scintillation cocktail (Microscint 0; Packard). The results are expressed as a percentage of the inhibition of the control radioligand-specific binding. The reference standard compounds are tested in each experiment at several concentrations to obtain a competition curve from which its $IC_{50}$ is calculated.

CB1/CB2 Functional Assay

A dose response curve was generated at eight concentrations in duplicate on CB1 and CB2 in light of reference agonists. The reference agonists for cannabinoid receptors is CP55,940. See FIGS. 1A, 1B, 2A, 2B, 3A and 3B.

Membranes (CB1, ES-110-MG or CB2, ES-111-MG) are mixed with GDP (volume:volume) and incubated for at least 15 mM on ice. In parallel, GTPδ[$^{35}$S] are mixed with the beads (volume:volume) just before starting the reaction. The following reagents are successively added in the wells of an Optiplate: 50 μl of ligand, 20 μl of the membranes:GDP mix, 10 μl of assay buffer for agonist testing and 20 μl of the GTPδ[$^{35}$S]: beads mix. The plates are covered with a topseal, shaken on an orbital shaker for 2 min, and then incubated between 30 to 60 min at room temperature. Then the plates are centrifuged for 10 min at 2000 rpm, incubated at room temperature between 1 to 4 hours and counted for 1 min with a PerkinElmer TopCount reader.

Using the above-identified assays, the binding data for certain benzofuran compounds to the CB1 and CB2 receptors have been obtained and is provided in Table 1, and Table 2 below.

TABLE 1

CB1 Binding Data

| Example No. | % Inhibition of Control Specific Binding | % of Control Specific Binding | | | SEM % Control | Test Concentration (MD) |
|---|---|---|---|---|---|---|
| | | 1st | 2nd | Mean | | |
| 1 | 36 | 68.6 | 59.6 | 64.1 | 4.5 | 1.0E−05 |
| 2 | 49 | 45.8 | 56.1 | 51 | 5.2 | 1.0E−05 |
| 3 | 34 | 54.1 | 78.5 | 66.3 | 12.2 | 1.0E−05 |
| 4 | 37 | 64.3 | 61.4 | 62.9 | 1.5 | 1.0E−05 |
| 5 | 96 | 0.4 | 7.7 | 4 | 3.7 | 1.0E−05 |
| 6 | 96 | 4.5 | 4.5 | 4.5 | 0 | 1.0E−05 |
| 7 | 98 | 0.9 | 2.6 | 1.8 | 0.8 | 1.0E−05 |
| 8 | 16 | 77.2 | 90 | 83.6 | 6.4 | 1.0E−05 |
| 9 | 8 | 87.7 | 96.1 | 91.9 | 4.2 | 1.0E−05 |

TABLE 2

CB2 Binding Data

| Example No. | % Inhibition of Control Specific Binding | % of Control Specific Binding | | | SEM % Control | Test Concentration (MD) |
|---|---|---|---|---|---|---|
| | | 1st | 2nd | Mean | | |
| 1 | 15 | 83.3 | 87.6 | 85.4 | 2.2 | 1.0E−05 |
| 2 | 38 | 59.8 | 64.7 | 62.3 | 2.5 | 1.0E−05 |
| 3 | −3 | 98.6 | 107.1 | 102.8 | 4.2 | 1.0E−05 |
| 4 | −8 | 105.7 | 109.7 | 107.7 | 2 | 1.0E−05 |
| 5 | 80 | 13.9 | 26.4 | 20.2 | 6.3 | 1.0E−05 |
| 6 | 93 | −1.5 | 15.9 | 7.2 | 8.7 | 1.0E−05 |
| 7 | 92 | 8.4 | 8.5 | 8.5 | 0.1 | 1.0E−05 |
| 8 | 9 | 89.2 | 93.3 | 91.2 | 2 | 1.0E−05 |
| 9 | −14 | 126.5 | 100.6 | 113.5 | 13 | 1.0E−05 |

Using the above identified functional assay, the activity of the CB1 and CB2 receptors was obtained and is shown in Tables 3 and 4 below. This data is also charted in FIGS. 1 through 3.

TABLE 3

CB1 Functional Activity

| Example No. | % Inhibition of Control Specific Binding CB1 | EC50 (nM) for GTP Binding | % Activation Average | Compound Activity |
|---|---|---|---|---|
| 5 | 96 | 0 | 56.75 | Agonist |
| 6 | 96 | 867 | 59.65 | Agonist |
| 7 | 98 | 459 | 71.88 | Agonist |

TABLE 4

CB2 Functional Activity

| Example No. | % Inhibition of Control Specific Binding CB2 | EC50 (nM) for GTP Binding | % Activation Average | Compound Activity |
|---|---|---|---|---|
| 5 | 80 | 103.39 | 55.55 | Agonist |
| 6 | 93 | 63.35 | 68.81 | Agonist |
| 7 | 92 | 188.67 | 45.79 | Agonist |

In Vivo Testing

Animals

All experiments were performed on male Sprague-Dawley rats (200-250 g). Rats were housed individually in plastic cages with soft bedding at room temperature and maintained on a 12-hour light-dark cycle with free access to food and water.

Surgical Procedures

All surgical procedures were performed with the rats anesthetized inhalational isoflurane in 100% oxygen, induced at 5% and maintained at 2%. Animals that showed neurologic deficits after surgery were excluded from the study. Prophylactic antibiotic (enrofloxacin 5 mg/kg subcutaneously) and analgesic (buprenorphine, 0.2-0.5 mg/kg, or morphine, 2.5 mg/kg, both given subcutaneously) were administered once daily for 3 days. Lumbar 5/6 Spinal-Nerve Ligation (Nerve-Ligation Model)

Figure 4:
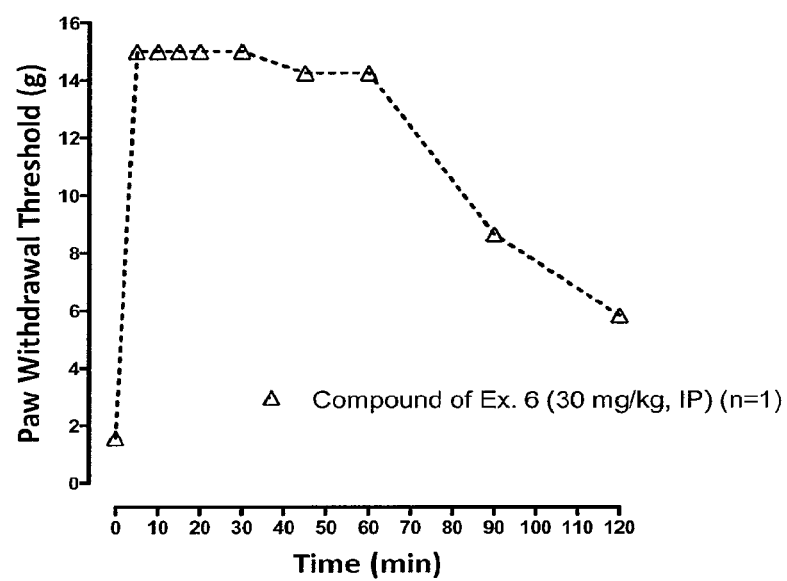
FIG. 4 shows paw withdrawal threshold versus time for IP administered compound of Example 6.

Neuropathic pain was induced following the methods of Kim and Chung. Kim S H, Chung J M. *An experimental model for peripheral neuropathy produced by segmental spinal nerve ligation in the rat*. Pain 1992; 50:355-63. Rats were anesthetized and placed prone under a microsurgical apparatus. A midline incision was made on the back, and the right paraspinal muscles were separated from the spinous processes at the L4-S2 levels. The L6 transverse process was carefully removed, and the L4/5 spinal nerves were identified. The L5 nerve was tightly ligated with a 6-0 silk suture. The right L6 spinal nerve was then located just caudal and medial to the sacroiliac junction and tightly ligated with a silk suture.
Intrathecal Catheterization Two weeks later after spinal nerve ligation, Intrathecal catheters (PE-10 tubing) was inserted into the rats while they were anesthetized with isoflurane, as described by Yaksh and Rudy. Yaksh T L, Rudy T A. *Chronic catheterization of the spinal subarachnoid space*. Physiology & Behavior 1976; 17:1031-6. A midline incision was made on the back of the neck. The muscle was freed at the attachment to the skull exposing the cisternal membrane. The membrane was opened with a stab blade and an 8.5 cm polyethylene (PE-10) catheter was then inserted through the cisternal opening, and passed carefully and caudally into the intrathecal space at the L1-L3 spinal segments. The end of the catheter was tunneled through the subcutaneous space over the frontal bones, flushed with 10 μl saline, and then plugged with a short length of wire Animal testing was performed 5-7 days after intrathecal catheter placement.
Assessment of Mechanical Allodynia in Rats To assess mechanical allodynia, the mechanical paw withdrawal threshold was measured with a series of von Frey hairs (range 0.4-15 g). Rats were placed in elevated Perspex enclosures (28 cm×15 cm×18 cm) with wire mesh bases and given 15-20 min to acclimatize to the testing environment. Rats will be allowed to acclimatize for 30 min in a clear plastic cage with a wire mesh bottom. The calibrated von Frey filament fibers were applied to the hindpaw briefly for 6 seconds to determine the paw withdrawal threshold before and after drug injection (intraperitoneally or intrathecally). A series of von Frey filaments with exponentially incremental stiffness (0.4, 0.7, 1.2, 2.0, 3.6, 5.5, 8.5 and 15 g) were used to measure the 50% threshold for hindpaw withdrawal in awake, unrestrained rats. Chaplan S R, Bach F W, Pogrel J W, Chung J M, Yaksh T L. *Quantitative assessment of tactile allodynia in the rat paw*. Journal of Neuroscience Methods 1994; 53:55-63. Brisk paw withdrawal from the pressure of a filament gently bent against the plantar paw was defined as a positive response, and absence of withdrawal within 6 s as a negative response. Filaments were touched to the hindpaw in sequential ascending or descending order until the threshold of response is crossed (allowing about 10 s between each increment of the von Frey filaments). Each time the threshold is crossed, the direction of stimulus presentation was reversed and the procedure will be resumed. Four responses were collected after the first threshold detection, and the 50% withdrawal thresholds were interpolated. In cases where response thresholds fell outside the range of detection, 15.00 and 0.25 g were, respectively, assigned for continuous negative or positive responses to the limit of stimuli.
Drugs The Compound of Example 6 was Prepared as a Solution in Dimethyl Sulfoxide (DMSO)
Results Intraperitoneal (IP) administration (FIG. 4) shows IP administration of 30 mg/kg in 0.5 ml of Example 6 produced an increase in mechanical paw withdrawal threshold. The peak effect for both drugs was noted within 5 min following IP administration. The peak threshold (15 g) lasted for one hour.

Figure 5:
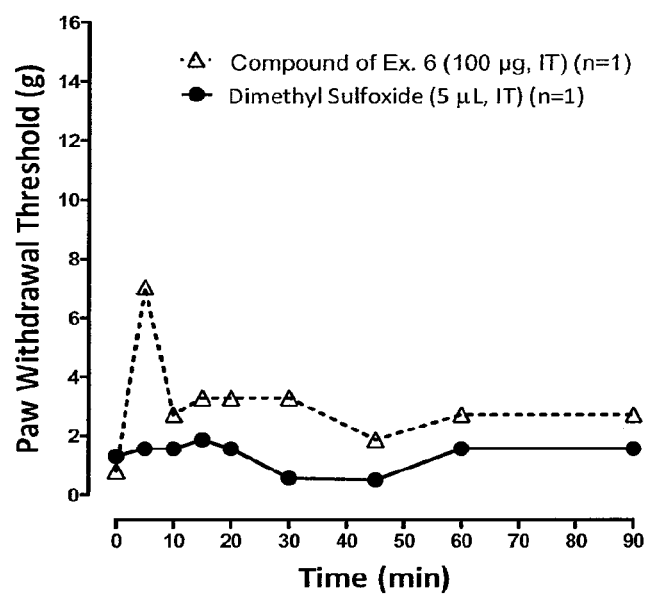
FIG. 5 shows paw withdrawal threshold versus time for IT administered compound of Example 6.
Figure 6:
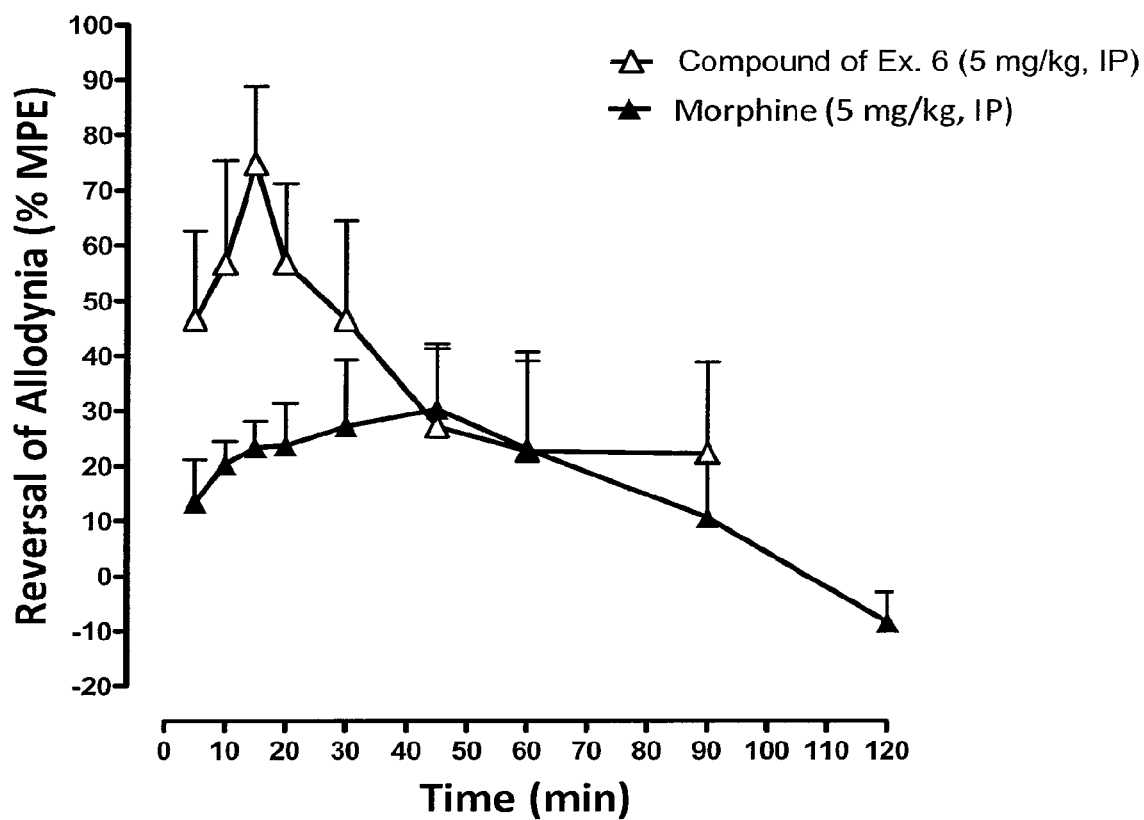
FIG. 6 shows reversal of allodynia as a function time with IP administered compound of Example 6 and IP administered morphine.

Intrathecal (IT) administration (FIG. 5) shows intrathecal (IT) administration of Example 6 produced a short-lived modest increase in paw withdrawal threshold at 5 min. The vehicle (DMSO) did not produce any appreciable effects on the baseline threshold. No behavioral abnormalities or side effects were noted in animals.
Conclusions The compound of Example 6 is a very potent analgesic in the neuropathic pain animal model when administered IP.
Pharmacology: Binding Assays All the compounds synthesized were screened at one concentration (1 μM) in a competitive binding experiment using membranes of Chinese hamster ovarian cells (CHO) expressing selectively the human CB1 (hCB1) or CB2 (hCB2) receptor. [$^3$H]-CP55940 at a concentration of 0.5 nM and [$^3$H]-WIN55212 at a concentration of 0.8 nM were used as radioligands for hCB1 and hCB2 assays, respectively. The results are expressed as a percent inhibition of control specific binding. Compounds which displaced the radioligand by more than 50% for either $hCB_1$ or $hCB_2$ receptors were arbitrary chosen for functional activity determination.

TABLE 8

Percentage of Inhibition of Specific Binding of [$^3$H]-CP55940 on hCB1 and of [$^3$H]-WIN55212-2 on hCB2 Receptor by Various Compounds at 1 μM

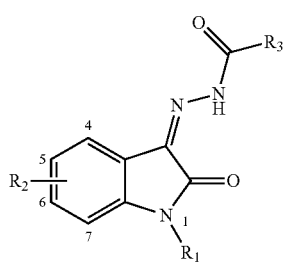

| Compound Example | R1 | R2 | position | R3 | % inhibition hCB1 receptor | % inhibition hCB2 receptor |
|---|---|---|---|---|---|---|
| 6 | $CH_3(CH_2)_5$ | H | — | Phenyl | 95.5 ± 0 | 92.8 ± 8.7 |
| 11 | $CH_3(CH_2)_5$ | H | — | Cyclohexyl | 65.8 ± 0.2 | 61 ± 2.1 |

TABLE 8-continued

Percentage of Inhibition of Specific Binding of [$^3$H]-CP55940 on hCB1 and of [$^3$H]-WIN55212-2 on hCB2 Receptor by Various Compounds at 1 μM

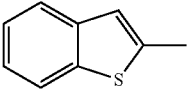

| Compound Example | R1 | R2 | position | R3 | % inhibition hCB1 receptor | % inhibition hCB2 receptor |
|---|---|---|---|---|---|---|
| 12 | $CH_3(CH_2)_5$ | H | — | $CH_3(CH_2)_4$ | 45.2 ± 9.5 | 36.6 ± 8.8 |
| 13 | $CH_3(CH_2)_5$ | H | — | 4-Cl—Ph | 46.6 ± 4.3 | 32.7 ± 5.3 |
| 14 | $CH_3(CH_2)_5$ | H | — | —O—tBu | 85.1 ± 3.3 | 82.3 ± 0.8 |
| 15 | $CH_3(CH_2)_5$ | H | — | —O—tBu | 75 ± 0.1 | 27 ± 3.7 |
| 16 | $CH_3(CH_2)_5$ | H | — | 2-Naphthyl | <30 | <30 |
| 17 | $CH_3(CH_2)_5$ | H | — | 4-MeO—Ph | 81.7 ± 1.1 | 56 ± 5.7 |
| 18 | $CH_3(CH_2)_5$ | H | — | 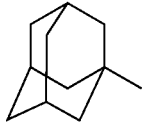 | <30 | <30 |
| 19 | $CH_3(CH_2)_5$ | H | — | 1-Naphthyl | 83.9 ± 0.9 | 69.8 ± 4 |
| 20 | $CH_3(CH_2)_5$ | H | — | 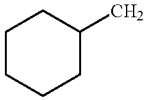 | 82.6 ± 1.2 | 90.7 ± 3.2 |
| 21 | $CH_3(CH_2)_2$ | H | — | Phenyl | 43 ± 1.2 | 32 ± 3.6 |
| 22 | $CH_3(CH_2)_3$ | H | — | Phenyl | 86 ± 2.4 | 70 ± 2.4 |
| 23 | $CH_3(CH_2)_4$ | H | — | Phenyl | 95 ± 0.9 | 80 ± 0.9 |
| 24 | $CH_3(CH_2)_{11}$ | H | — | Phenyl | 23.8 ± 4.5 | 24.3 ± 4.1 |
| 25 | cyclohexyl-$CH_2$ | H | — | Phenyl | 99 ± 1.1 | 100 ± 0.4 |
| 26 | 4-chlorobenzyl | H | — | Phenyl | 94.5 ± 0.8 | 22 ± 1.6 |
| 27 | 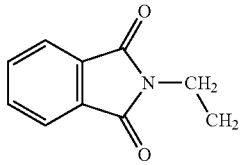 | H | — | Phenyl | 3 ± 4.1 | 3 ± 3.2 |
| 28 | $CH_3(CH_2)_5$ | Me | 7 | Phenyl | 67 ± 1.6 | 68 ± 3.7 |
| 29 | $CH_3(CH_2)_5$ | Cl | 7 | Phenyl | 60 ± 1 | 29 ± 4.5 |
| 30 | $CH_3(CH_2)_5$ | I | 7 | Phenyl | 61 ± 2.5 | 66 ± 3.2 |
| 31 | $CH_3(CH_2)_5$ | Me | 5 | Phenyl | 22 ± 0.9 | 1 ± 2.7 |
| 32 | $CH_3(CH_2)_5$ | MeO | 5 | Phenyl | 26 ± 3.1 | 17 ± 1.2 |
| 33 | $CH_3(CH_2)_5$ | F | 5 | Phenyl | 57 ± 0.7 | 46 ± 1.7 |
| 34 | $CH_3(CH_2)_5$ | Cl | 5 | Phenyl | 9 ± 1.4 | 6 ± 1.4 |
| 35 | $CH_3(CH_2)_4$ | I | 5 | Phenyl | 25 ± 0.2 | 10 ± 0.2 |

Pharmacology: Cannabinoid Receptors Mediated Functional Activity

Functional activity for acyl hydrazone was evaluated using [$^{35}$S]GTP-γ-S assay in CHO membrane extracts expressing recombinant hCB$_1$ receptor or hCB$_2$ receptor. The assay relies on the binding of [$^{35}$S]GTP-γ-S, a radiolabeled nonhydrolyzable GTP analogue, to the G protein upon binding of an agonist of the G-protein-coupled receptor. In this system, agonists stimulate [$^{35}$S]GTP-γ-S binding whereas neutral antagonist have no effect and inverse agonists decrease [$^{35}$S]GTP-γ-S basal binding.

In Vivo Evaluation

Animals

Adult, male Sprague Dawley (Harlan Sprague Dawley, Indianapolis, Ind.) rats weighing 120-150 gm were used in experimental procedures approved by the Animal Care and Use Committee of the M. D. Anderson Cancer Center, University of Texas. Animals were housed three per cage on a 12/12 hr light/dark cycle with water and food pellets available ad libitum.

Lumbar 5/6 Spinal Nerve Ligation Pain Model

All surgical procedures were performed under deep isoflurane anesthesia in 100% $O_2$. The spinal nerve ligation (SNL) was performed as described previously. Kim, S. H., et al., *An Experimental Model for Peripheral Neuropathy Produced by Segmental Spinal Nerve Ligation in the Rat*, Pain, 1992, 50:355-63. Briefly, a midline incision above the lumbar spine exposed the left L6 transverse process. The process was then removed, the left L5 and L6 spinal nerves were isolated, and both nerves were tightly ligated with 6-0 silk. Prophylactic antibiotic (norfloxacin 5 mg/kg subcutaneously) and analgesic (buprenorphine, 0.2-0.5 mg/kg, or morphine, 2.5 mg/kg, given subcutaneously) were administered once daily for 3 days. The rats were allowed to recover for 5-6 days before being used for behavioral testings. All the experiments were conducted 10-14 days after spinal nerve ligation.

Assessment of Mechanical Withdrawal Thresholds

Rats were placed in a compartment with a wire mesh bottom and allowed to acclimate for a minimum of 30 min before testing. Mechanical sensitivity was assessed using a series of Von Frey filaments with logarithmic incremental stiffness (0.41, 0.70, 1.20, 2.00, 3.63, 5.50, 8.50, and 15.1 g) (Stoelting, Wood Dale, Ill.) as previously described, and 50% probability withdrawal thresholds were calculated with the up-down method. Chaplan, S. R., et al., *Quantitative Assessment of Tactile Allodynia in the Rat Paw*, Journal of Neuroscience Methods, 1994, 53:55-63; Dixon, W., *The Up-and-Down Method for Small Samples*, J Am Stat Assoc, 1965, 60:967-978. In brief, beginning with the 2.0-g probe, filaments were applied to the plantar surface of a hind paw for 6-8 s, in an ascending or descending order after a negative or positive withdrawal response, respectively. Six consecutive responses from the first change in the response were used to calculate the withdrawal threshold (in grams). In cases where response thresholds fell outside the range of detection, 15.00 and 0.25 g were, respectively, assigned for continuous negative or positive responses to the limit of stimuli. The percent maximal possible effect (% MPE) was calculated as ([postdrug threshold−baseline threshold]/[cutoff threshold (15 g)−baseline threshold])×100.

Open Field Chamber Testing

The automated open-field chamber (Med Associates ENV-515 Test Environment, St. Albans, Vt.) 43.2×43.2×30.5 cm (L×W×H) equipped with three pairs of 16 infrared arrays that continually monitored the animal's movement was used to determine potential CNS effects of compound of Example 6 and the vehicle in naïve rats. Rats were individually tested 15 min after i.p. drug administration. The infrared beams were set 2.5 cm apart horizontally and at a height of 3 cm above the floor, with the rearing array set at 12 cm from the floor. The area in the box was divided into 4 equal quadrants (zones), with data collected within each quadrant and across quadrants (zone entries). An ambulatory movement was defined as a motion of at least 5 cm and was coded by quadrant. Vertical movements were counted when the rat moved vertically a minimum of 12 cm from the floor. Zone entries were defined as an entry into a zone (from another zone). Entry into a zone was counted when the rat was far enough into the zone to break 2 sets of photoelectric beams for the new zone beams during an ambulatory movement.

Results and Discussion

Structure-Activity Relationships

The first objective was to study the impact on the affinity for cannabinoid receptors of a hydrogen bond acceptor bore by the hydrazine moiety. None of the sulfone derivatives of Examples 8 and 9, urea derivatives of Examples 3 and 4 or thiourea derivatives of Examples 1 and 2 displayed significant binding at 10 μM for either $CB_1$ or $CB_2$ (Table 6).

TABLE 6

Percentage of Inhibition of Specific Binding of [$^3$H]-CP55940 on hCB1 and of [$^3$H]-WIN55212-2 on hCB2 Receptor by Compounds of Examples 1-10 at 10 μM

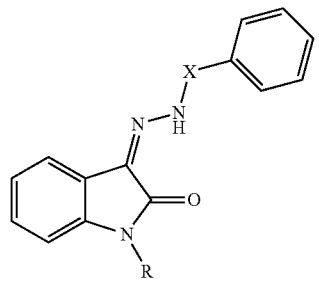

| Compound Example | R | X | hCB$_1$ receptor[a] % inhibition | hCB$_2$ receptor[b] % inhibition |
|---|---|---|---|---|
| 3 | 2-cyclohexylethyl | (C=O)NH | <40 | <40 |
| 5 | 2-cyclohexylethyl | C=O | 96 ± 3.7 | 79.8 ± 6.3 |
| 10 | 2-cyclohexylethyl | (C=O)CH$_2$ | 88.8 ± 0.6 | 47.2 ± 7.7 |
| 1 | 2-cyclohexylethyl | (C=S)NH— | <40 | <40 |
| 8 | 2-cyclohexylethyl | SO$_2$ | <40 | <40 |
| 4 | CH$_3$(CH$_2$)$_5$ | (C=O)NH | <40 | <40 |
| 6 | CH$_3$(CH$_2$)$_5$ | C=O | 95.5 ± 0 | 92.8 ± 8.7 |
| 7 | CH$_3$(CH$_2$)$_5$ | (C=O)CH$_2$ | 98.2 ± 0.8 | 91.5 ± 0.1 |
| 2 | CH$_3$(CH$_2$)$_5$ | (C=S)NH | 49 ± 5.2 | 37.7 ± 2.5 |
| 9 | CH$_3$(CH$_2$)$_5$ | SO$_2$ | <40 | <40 |

The acyl hydrazone derivatives of Examples 5, 10, 6 and 7 displaced a significant percentage of the radiolabeled ligands for both $CB_1$ and $CB_2$ receptors. Inactivity of compounds of Examples 3 and 4 compared to compounds of Examples 10 and 7 might be explained by unfavorable interaction between the receptor and the polar N—H functionality or a difference in the positioning of the phenyl ring. In the case of compounds of Examples 3 and 4, a hydrogen bond between the hydrogen of the aniline moiety and the =N might favor conformation A (Scheme 3) compared to compounds of Examples 10 and 7 (see conformation A compared to conformations B and C in the Scheme 3).

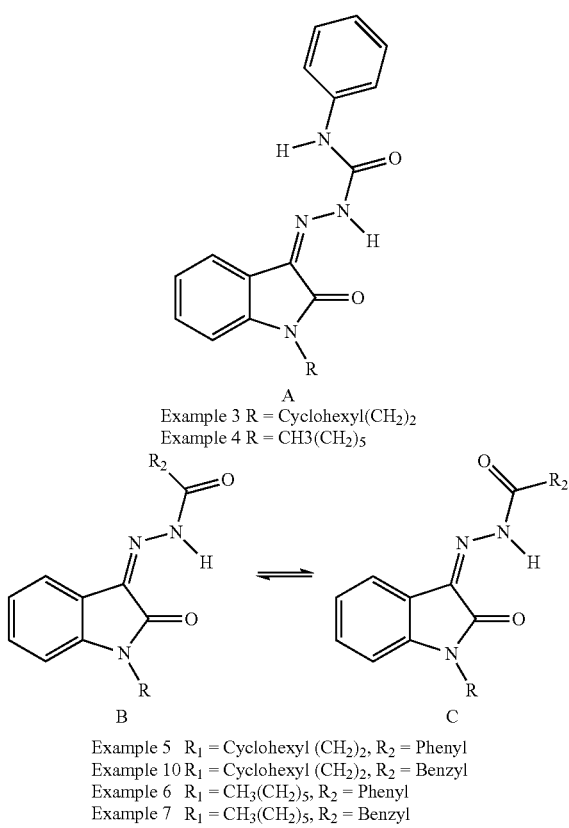

A
Example 3 R = Cyclohexyl(CH$_2$)$_2$
Example 4 R = CH3(CH$_2$)$_5$

B ⇌ C

Example 5  R$_1$ = Cyclohexyl (CH$_2$)$_2$, R$_2$ = Phenyl
Example 10 R$_1$ = Cyclohexyl (CH$_2$)$_2$, R$_2$ = Benzyl
Example 6  R$_1$ = CH$_3$(CH$_2$)$_5$, R$_2$ = Phenyl
Example 7  R$_1$ = CH$_3$(CH$_2$)$_5$, R$_2$ = Benzyl Considering the weak affinity of compound of Example 2, the hydrogen atom of a thiol form tautomer might be involved in a hydrogen bond interaction with the =N, yielding to conformation similar to isomer C.

Compounds which exhibited a percentage of inhibition of specific binding above 50% for either hCB$_1$ or hCB$_2$ receptors were arbitrary chose for functional activity determination (Table 7).

CB$_1$ receptor. The benzoyl hydrazone of Example 6 exhibited the better functional activity, being seven times less potent compared to the reference compound CP55,940. Moreover, compound of Example 6 showed a CB$_2$ receptor selectivity, with a ratio EC$_{50}$(CB$_1$)/EC$_{50}$(CB$_2$)=14 with a moderate potency on CB$_1$. The N-hexyl moiety was better tolerated by either CB$_1$ or CB$_2$ compared to the N-cyclohexylethyl moiety as compound of Examples 6 and 7 were more potents and efficients compared to compounds of Examples 5 and 10, for both CB$_1$ and CB$_2$ receptors. An additional methylene moiety between the carbonyl and the phenyl ring, as in the phenylacetyl derivative of Example 7, resulted in a slight increase of the CB$_1$ potency and efficacy and a decrease of the CB$_2$ potency and efficacy.

CB1 and CB2 assay data are presented as the mean of two determinations. Assay reproducibility was monitored by the use of a reference compounds, CP55,940. For replicate determinations, the maximum variability tolerated in the test was of ±20% around the average of the replicates. Efficacies (E$_{max}$) for CB1 or CB2 are expressed as a percentage relative to the efficacy of CP55940.

As our goal was to design CB2 selective compounds, we decided to modify the benzoyl moiety of compound of Example 6, in order to improve its potency and selectivity. Bulky aromatic moieties such as 2-naphthyl (compound of Example 16) and benzothiophene (compound of Example 18) were not tolerated by either CB1 or CB2 receptors whereas compound of Example 19, bearing a 1-naphthyl group exhibited affinity for both CB1 and CB2 receptors as expected and as previously shown for classical aminoalkylindoles. Huffman, J. W., et al., *Recent Developments in the Medicinal Chemistry of Cannabimimetic Indoles, Pyrroles and Indenes*, Current Medicinal Chemistry, 2005, 12:1395-1411. Surprisingly, the adamantyl derivative of Example 20 at a concentration of 1 µM, was able to displace more than 85% all the [$^3$H]-CP55,940 from both CB1 and CB2 receptors. Impact of the intracyclic nitrogen substitution was studied. Length variation from 4 to six carbon atoms (Compounds of Examples 6, 22 and 23) has no impact on the percentage of displacement of the radiolabeled ligands for both CB1 and CB2 receptors. The propyl derivatives of Example 21, suf-

TABLE 7

Determination of Potency (EC$_{50}$) and Maximal Stimulation (E$_{max}$) on hCB1 and hCB2 Receptors of Compounds of Examples 5, 10, 6 and 7

| Compound Example | R | X | [$^{35}$S]GTP-γ-S (hCB1) | | [$^{35}$S]GTP-γ-S (hCB2) | |
|---|---|---|---|---|---|---|
| | | | EC$_{50}$ (nM ± SEM) | E$_{max}$ (%) | EC$_{50}$ (nM ± SEM) | E$_{max}$ (%) |
| | CP55,940 | | 10.3 ± 1 | 100 | 8.66 ± 1 | 100 |
| 5 | 2-cyclohexylethyl | C=O | ND | 56.8 | 103.4 ± 1.6 | 55.6 |
| 10 | 2-cyclohexylethyl | (C=O)CH$_2$ | 1238.8 ± 1.2 | 75 | ND | 21 |
| 6 | CH$_3$(CH$_2$)$_5$ | CO | 867.0 ± 1.1 | 59.7 | 63.4 ± 1.3 | 68.8 |
| 7 | CH$_3$(CH$_2$)$_5$ | (C=O)CH$_2$ | 459.0 ± 1.1 | 71.9 | 188.7 ± 1.3 | 45.8 |

As acyl hydrazone derivatives of Examples 5, 10, 6 and 7 displaced the radioligand by more than 50% in the binding assay, functional activities were evaluated. All the compounds tested, exhibited an agonist activity for CB$_1$ with a moderate potency, as the best EC$_{50}$ obtained was 459 nM. The corresponding efficacies were also moderate to good ranging from 56.8% to 75% compared with CP55940. The potencies (EC$_{50}$) for CB$_2$ receptor were 2 to 14 times better compared to fered a small decrease of affinity. On the other hand, the dodecyl derivatives of Example 24 and the phthalimide derivative of Example 27 were not able to displace the ligand from both CB1 and CB2 receptors. Less rigid aryl or cycloalkyl rings such as compounds of Examples 25 or 26 showed a good activity. Isatin substitution in the position 5 either by electron donor or withdrawing groups (compounds of Examples 31, 32, 33, 34 and 35) resulted in a lost of affinity for either CB1 or CB2 receptors. Isatin substitution in the position 7 was less drastic in term of lost of affinity. Compounds of Examples 28, 29 and 30 showed less affinity compared to compound of Example 6.

Functional activity was determined for compounds which displaced the radioligand by more than 50% for either hCB1 or hCB2 receptors. See Table 9 immediately below.

TABLE 9

Determination of Potency ($EC_{50}$) and Maximal Stimulation ($E_{max}$) on $hCB_1$ and $hCB_2$ Receptors of Various Compounds

| Compound Example | [$^{35}$S]GTP-γ-S hCB1 | | [$^{35}$S]GTP-γ-S hCB2 | |
|---|---|---|---|---|
| | $EC_{50}$ (nM ± SEM) | $E_{max}$ (%) | $EC_{50}$ (nM ± SEM) | $E_{max}$ (%) |
| CP 55,940 | 5.0 ± 1 | 100 | 2.7 ± 1 | 100 |
| 6 | 867.0 ± 1.1 | 59.7 | 63.4 ± 1.3 | 68.8 |
| 11 | ND | 40.9[a] | 79.1 ± 1.5 | 58 |
| 14 | 937.1 ± 1.2 | 92 | 22.4 ± 1.3 | 43.4 |
| 15 | NA | NA | ND | 23.4[a] |
| 17 | 852 ± 1.2 | 71 | 143.4 ± 2.6 | 49.5 |
| 19 | ND | 12.9[a] | 202.2 ± 2 | 30.5 |
| 20 | ND | 34.6[a] | ND | 32.12[a] |
| 21 | NA | NA | 200.7 ± 1.5 | 61.4 |
| 22 | ND | 69[a] | 40.1 ± 1.5 | 98.9 |
| 23 | 314.1 ± 1.6 | 95.1 | 240 ± 3.2 | 68.5 |
| 25 | 62.3 ± 1.3 | 99 | 9.8 ± 1.1 | 65.7 |
| 26 | 895.6 ± 1.2 | 72 | 131.1 ± 1.7 | 39.8 |
| 28 | NA | NA | 84.0 ± 2.2 | 34.2 |
| 29 | NA | NA | 645.5 ± 1.3 | 64.8 |
| 30 | NA | NA | ND | 55[a] |
| 33 | NA | NA | 186.9 ± 1.7 | 33.8 |

$CB_1$ and $CB_2$ assay data are presented as the mean of two determinations. Assay reproducibility was monitored by the use of a reference compounds, CP 55,940. For replicate determinations, the maximum variability tolerated in the test was of ±20% around the average of the replicates. Efficacies ($E_{max}$) for $CB_1$ or $CB_2$ are expressed as a percentage relative to the efficacy of CP 55,940. [a] Efficacy determined at 3 μM.

According to previous studies, in the cannabimimetic aminoalkylindole series, aromatic stacking are the primary interactions for CB1 receptor binding. Huffman, J. W., et al., 3-*Indolyl*-1-*Naphthylmethanes: New Cannabimimetic Indoles Provide Evidence for Aromatic Stacking Interactions with the CB1 Cannabinoid Receptor*, Bioorganic & Medicinal Chemistry, 2003, 11:539-549. As expected, replacement of the compound of Example 6 phenyl ring by a cyclohexyl ring (compound of Example 11), resulted in a decrease of CB1 activity. CB2 activities for both compounds are in the same range and did not suffer this potential lost of aromatic stacking interactions. The same effect on CB1 functional activity was obtained using the bulky tert-butoxyl radical in compound of Example 14. Furthermore, in this case, CB2 functional activity potency was improved. The corresponding E conformer, compound of Example 15, failed to exhibited functional activity on both CB1 and CB2 receptors. Compound of Example 17 which results from substitution by a methoxy in the para position of the phenyl hydrazoic moiety of compound of Example 6, showed a decrease in term of potency and efficacy for the CB2 receptor, whereas activity for CB1 receptor was not impacted. Substitution at this position seems to be critical for CB2, as it was confirmed by the loss of affinity of compound of Example 13. Compounds of Examples 19 and 20, which showed more than 80% of [$^3$H]-CP55,940 displacement in the primary $CB_1$ screening, didn't exhibit relevant functional activities. Both compounds failed to be antagonist as evaluated in a $CB_1$ antagonist functional assay (data not shown). $CB_2$ activities for these two compounds were moderate compared with compound of Example 6.

Length variation of the aliphatic chain bore by nitrogen, from three to six carbon atoms (Compounds of Examples 6, 21, 22 and 23) has a dramatic impact in term of CB1 functional activity. The propyl derivatives of Example 21, suffered a small decrease in term of CB2 functional activity compared with the hexyl derivatives of Example 6, or the butyl derivatives of Example 22. On the other hand, despite a modest CB2 activity, this compound showed CB2 specificity. This specificity was almost maintained with compound of Example 22 with an increase of CB2 functional activity compared to compound of Example 6. Surprisingly, functional activities for the pentyl analog of Example 23, was lower for CB2 and higher for CB1. Aliphatic chain replacement by a cyclohexylmethyl moiety (compound of Example 25), resulted in high increase of both CB1 and CB2 functional activities, compared to compound of Example 6. Compound of Example 25 is the most potent in term of CB2 functional activity of this series. Substitution by a chlorine atom in the para position of the benzyl ring (Compound of Example 26) resulted in a decrease of both selectivity and CB2 activity. Despite a good CB2 potency, compounds of Example 28 exhibited a low efficacy for CB2. Increasing the bulkiness of the substituent in compound of Examples 29 and 30 resulted in a lost of CB2 functional activity. Substitution in the position 7 of the isatine ring, resulted in a lost of CB1 activity. Compound of Example 33 showed a weak CB2 activity. In conclusion, replacing the phenyl ring by an aliphatic ring and shortening its n-hexyl chain from 6 to 4 carbon atoms of compound of Example 6, resulted in a decrease in term of CB1 functional activity, maintaining or improving the CB2 functional activity. Substitution in the position 5 or 7 of the oxindole ring led to a lost of CB1 functional activity and a decrease of CB2 activity.

This experiment was repeated in a similar manner with the compounds of Examples 36-41. The results are shown in Table 10 immediately below.

TABLE 10

Determination of Potency ($EC_{50}$) and Maximal Stimulation ($E_{max}$) on $hCB_1$ and $hCB_2$ Receptors of Various Compounds

| Compound Example | [$^{35}$S]GTP-γ-S hCB1 | | [$^{35}$S]GTP-γ-S hCB2 | |
|---|---|---|---|---|
| | $EC_{50}$ (nM) | $E_{max}$ (%) | $EC_{50}$ (nM) | $E_{max}$ (%) |
| 36 | NA | NA | 85 | −95 |
| 37 | 61.2 | 40.8 | 18 | −82 |
| 38 | NA | NA | 102 | −96 |
| 39 | NA | NA | 5.8 | −108 |
| 40 | NA | NA | 85 | −95 |
| 41 | NA | NA | 540 | −104 |

Figure 12A:
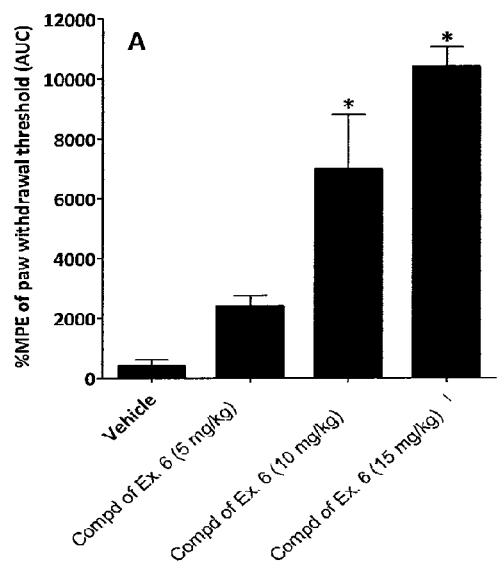
FIGS. 12A and 12B show effects of compound of Example 6 (i.p) on tactile allodynia in a spinal nerve ligation neuropathic pain model in rats (n=6 per group). Compound of Example 6 increases in the withdrawal threshold of the nerve-injured paw in a dose-dependent manner.
Figure 12B:
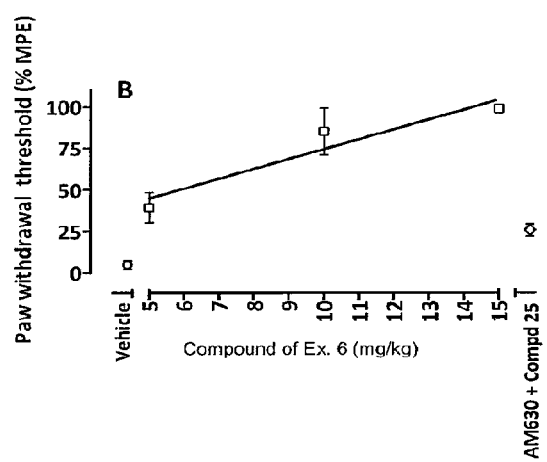
Figure 13A:
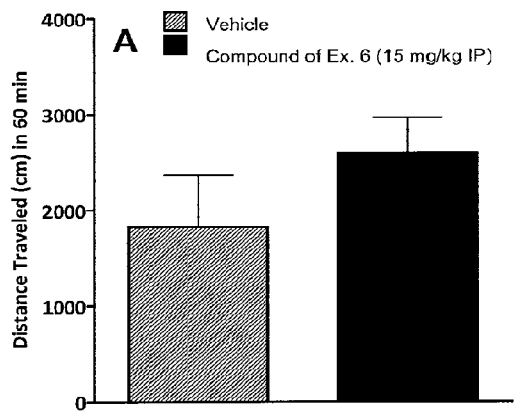
FIGS. 13A, 13B, 13C and 13D show absence of psychoactive cannabinoid effect of compound of Example 6. Exploratory behavior was tested in the open field following i.p. administration of 15 mg/kg of compound of Example 6 i.p. or the vehicle (n=6 per group). The following parameters were scored for 60 minutes: distance traveled (FIG. 13A), ambulatory time (FIG. 13B), vertical activity (FIG. 13C), and number of zone entries (FIG. 13D). No significant differences were observed between compound of Example 6 and its vehicle (t test).
Figure 13B:
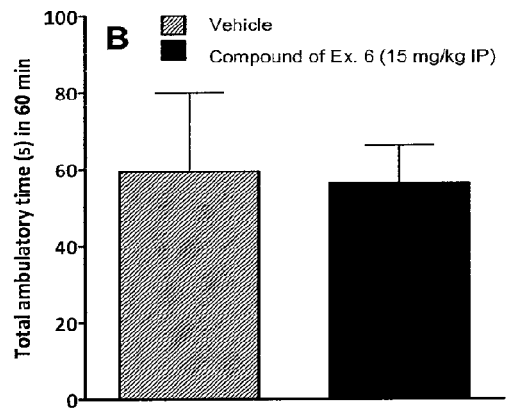
Figure 13C:
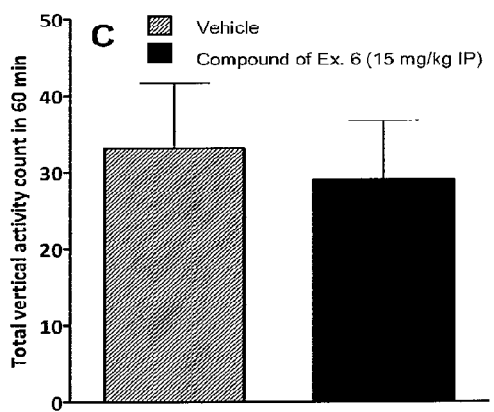
Figure 13D:
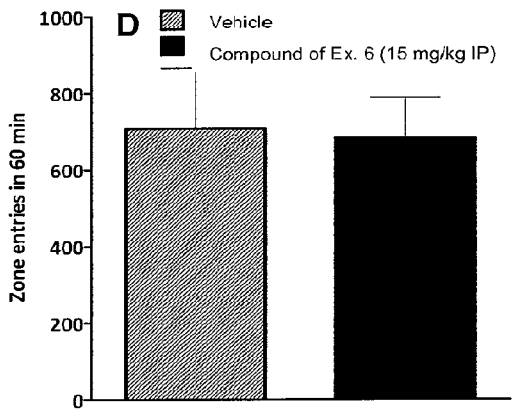

In rats, SNL produced tactile allodynia 1 week following surgery as demonstrated by a reduction in paw withdrawal threshold to mechanical stimulation to 1.6±0.9 g using Von Frey filaments. Compound of Example 6 treatment attenuated tactile allodynia in a dose-related manner with an $ED_{50}$ of 5.9 (95% CI 4.5-7.9) mg/kg, i.p. and $ED_{90}$ of 12 (95% CI 9.6-15.5) mg/kg, i.p. The higher doses (10 mg/kg and 15 mg/kg) produced significantly antiallodynic effect (P<0.01) than that noted with 5 mg/kg of compound of Example 6 (FIG. 12). Pretreatment with 5 mg/kg i.p. of a selective CB2 antagonist AM630 antagonized the effects of compound of Example 6.

Hosohata, Y., et al., *AM630 Antagonism of Cannabinoid-Stimulated [35S]GTP Gamma S Binding in the Mouse Brain*, Eur J Pharmacol, 1997, 321, R1-3; Ross, R. A., et al., *Agonist-Inverse Agonist Characterization at CB1 and CB2 Cannabinoid Receptors of L759633, L759656, and AM630*, Br J Pharmacol, 1999, 126:665-72. Administration of 15 mg/kg i.p. of compound of Example 6 did not decrease the exploratory behavior in rats (FIG. 13).

In summary, we have discovered a series of novel, CB2 receptor agonists that are potent and selective. A major focus of the optimization effort was to increase in selectivity in order to attenuate the potential CB1 receptor CNS side effects of the initial lead compound of Example 6. This compound is active in models of neuropathic pain without producing any CNS side effects as measured by the open field model. More potent and more CB2 receptor selective compounds such as compounds of Examples 11, 14 or 22, were discovered and will be evaluated for their in vivo activities. ADMET of compound of Example 6 is undergoing in order to assess its ability to cross the blood brain barrier and to address potential future issues of this novel series.

Prevention of Chemotherapy-Induced Peripheral Neuropathy by Cannabinoid Receptor Subtype 2 (CB2) Modulators CB2 agonist is able to suppress neuropathic nociception induced by a chemotherapeutic agent. Prevention of the development of this peripheral neuropathy by pre or co-administration of a CB2 modulator (or any other drug) with a chemotherapeutic agent is provided herein.

Paclitaxel is an antineoplastic drug used in cancer chemotherapy. Paclitaxel is used to treat patients with lung, ovarian, breast, head and neck cancer, and advanced forms of Kaposi's sarcoma. Neuropathic pain is one of the side effects associated with the use of paclitaxel. Mielke, S., et al., *Peripheral neuropathy: a persisting challenge in paclitaxel-based regimes*, Eur J Cancer, 2006, 42:24-30. Neuropathic pain, a debilitating condition characterized by severe, persistent pain that is refractory to traditional analgesia. This side effect is also associated with the use of other antineoplastic agents such as vinca alkaloids (e.g. vincristine), other taxane derivatives or platinum-derivatives (e.g. cisplatin). In the US, the annual healthcare cost attributable to neuropathic pain is almost $40 billion. Turk, D. C., *Clinical effectiveness and cost-effectiveness of treatments for patients with chronic pain*, Clin J Pain, 2002, 18:355-65. There is no effective or satisfactory treatment for neuropathic pain. Warms, C. A., et al., *Treatments for chronic pain associated with spinal cord injuries: many are tried, few are helpful*, Clin J Pain, 2002, 18:154-63.

Chemotherapy-induced neuropathic pain is dose dependent; the mechanism of which might be accompanied by morphological to primary afferent. Recently, CB2 has emerged as a new target for the treatment of neuropathic pain with an added advantage of lacking the psychotropic side effects that are normally seen with the use of the CB1 agonists. Cox, M. L., *The antinociceptive effect of [Delta]9-tetrahydrocannabinol in the arthritic rat involves the CB2 cannabinoid receptor*, European Journal of Pharmacology, 2007, 570:50-56; Beltramo, M., et al., *C2 receptor-mediated antihyperalgesia: possible direct involvement of neural mechanisms*, Eur J Neurosci, 2006, 23:1530-8; Ibrahim, M. M., *CB2 cannabinoid receptor mediation of antinociception*, Pain, 2006, 122:36-42; Guindon, J., et al., *Cannabinoid CB2 receptors: a therapeutic target for the treatment of inflammatory and neuropathic pain*, Br J Pharmacol, 2007.

Peripheral nerve injury induces CB2 protein expression in rat sensory neurons. Wotherspoon, G., *Peripheral nerve injury induces cannabinoid receptor 2 protein expression in rat sensory neurons*, Neuroscience, 2005, 135:235-45. CB2 mRNA is expressed in dorsal root ganglia (DRG) of neuropathic rats and is up-regulated in the spinal cord of neuropathic rats. CB2 mRNA expression was also shown in cultured spinal cord microglia and are upregulated in reactive microglia. Beltramo, M., *CB2 receptor-mediated antihyperalgesia: possible direct involvement of neutral mechanicms*, Eur J Neurosci, 2006, 23:1530-8; Ashton, J. C., *Class M: The Cannabinoid CB2 Receptor as a Target for Inflammation-Dependent Neurodegeneration*, Current Neuropharmacology, 2007, 5:73-80; Romero-Sandoval, A., et al., *Spinal Cannabinoid Receptor Type 2 Activation Reduces Hypersensitivity and Spinal Cord Glial Activation after Paw Incision*, Anesthesiology, 2007, 106:787-794.

CB2 agonists are neuroprotective and are emerging as a target for treating demyelinating diseases such as multiple sclerosis. Arevalo-Martin, A., et al., *CB(2) cannabinoid receptors as an emerging target for demyelinating diseases: from neuroimmune interactions to cell replacement strategies*, Br J Pharmacol, 2007. For instance, treatment with a selective CB2 agonist JWH-015 not only switched microglial cells morphology toward normal in the spinal cord of Theiler's murine encephalomyelitis virus-infected mice, but also significantly improved the neurological recovery and remyelination process. Arevalo-Martin, A., et al., *Therapeutic action of cannabinoids in a murine model of multiple sclerosis*, J Neurosci 2003, 23:2511-6. Cannabinoids abrogated major histocompatibility complex class II antigen expression, and decreased the number of CD4-infiltrating T cells. This protective mechanism of CB2 agonists has been attributed to reduction in the release of inflammatory cytokines or reactive oxygen species and/or increase in the production of protective molecules such as TGFa or anti-inflammatory cytokines such as IL-10. Sagrego, O., et al., *Cannabinoids and neuroprotection in basal ganglia disorders*, Mol Neurobiol, 2007, 36:82-91.

The use of CB2 agonists produce a dose-dependent reduction in mechano-allodynia and mechano-hyperalgesia in paclitaxel-treated rats, and the duration of effect is dependent on the duration of action of the CB2 agonist studied. There is evidence that a non-specific cannabinoid agonist with both CB1 and CB2 activities was able to prevent mechanical allodynia induced by cisplatinum. Vera, G., et al., *WIN 55, 212-2 prevents mechanical allodynia but not alterations in feeding behaviour induced by chronic cisplatin in the rat*, Life Sci, 2007, 81:468-79. Provided herein is a treatment that prevents the development of chemotherapy induced-peripheral neuropathy. Administration of the compound of Example 6, a novel CB2 selective agonist, prevented the development of neuropathic pain induced by paclitaxel.

(A) Paclitaxel-Induced Neuropathy

First, an experiment was performed to demonstrate that paclitaxel can produce the rat model of paclitaxel-induced neuropathy. A mixture of saline and CREMOPHOR®ELP 10% was used as vehicle for paclitaxel. It was injected at a concentration of 1.0 mg/kg intraperitoneally to the chemotherapy-treated group of rats on 4 consecutive days for a final cumulative dose of 4 mg/kg to 18 rats.

Figure 14:
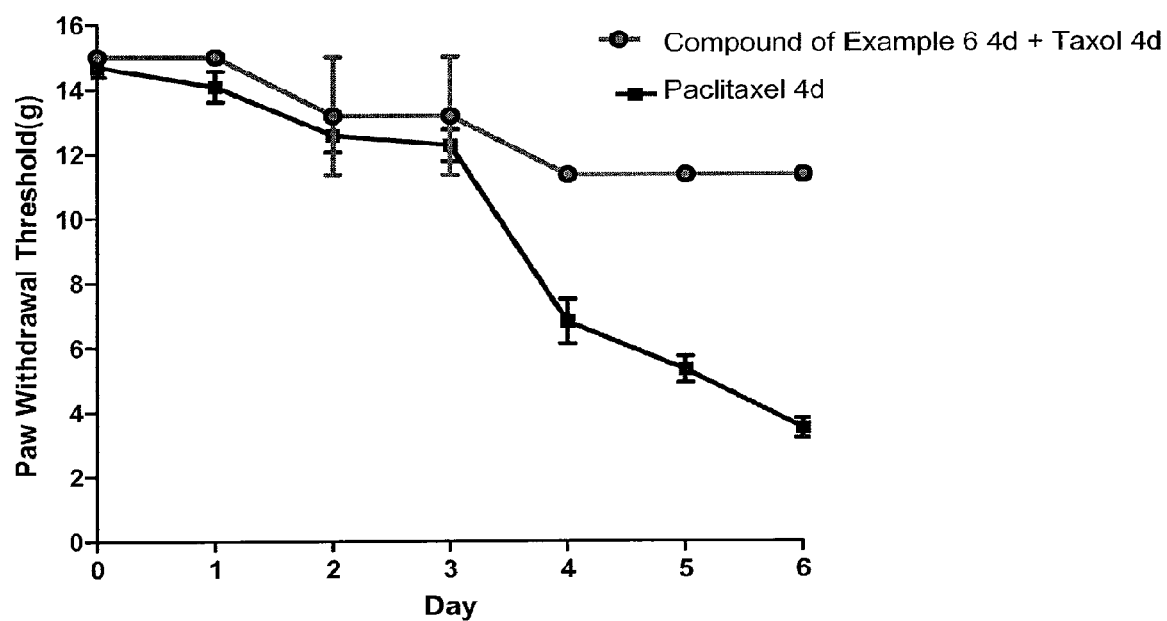
FIG. 14 shows the effects of the compound of Example 6 on Paclitaxel-induced neuropathy in rats (right paw). Peripheral neuropathy started to develop within a few days of paclitaxel administration, but was prevented by administration of the compound of Example 6.

Assessment of neuropathic pain. Paw withdrawal thresholds were determined daily in both hind paws of each animal using calibrated von Frey monofilaments according to an up-down procedure. A series of von Frey filaments with exponentially incremental degrees of stiffness (0.4, 0.7, 1.2, 2.0, 3.6, 5.5, 8.5, and 15.1 g) was used to measure the 50% threshold for both hindpaw withdrawal in awake, unrestrained rats. Chaplan, S. R., *Quantitative assessment of tactile allodynia in the rat paw*, Journal of Neuroscience Methods, 1994, 53:55-63. Brisk paw withdrawal from the pressure of a filament gently bent against the plantar surface of the paw was defined as a positive response, and absence of withdrawal within 6 sec was considered a negative response. The series of filaments touched the hindpaw in sequential ascending or descending order of stiffness until the threshold of response was crossed (allowing about 10 sec between each increment). Each time the threshold was crossed, the direction of stimulus presentation was reversed and the procedure resumed. Four responses were collected after the first threshold detection, and the 50% withdrawal thresholds was interpolated. In cases in which the response thresholds fall outside the range of detection, 15.1 and 0.25 g were assigned for continuous negative or positive responses, respectively, to the limits of stimulation. FIG. 14 shows that peripheral neuropathy started to develop within a few days.

B) Prevention of Neuropathy Induced by Paclitaxel

These experiments were designed to show that the administration of the compound of Example 3, 30 minutes prior to the administration of paclitaxel will prevent the development of neuropathy. Group 1 of rats received paclitaxel for four days, as described immediately above in subpart (A) titled "Paclitaxel-induced Neuropathy." In group 2, a dose of 15 mg/kg of the compound of Example 6, injected intraperitoneally was administered 30 minutes prior to the administration of paclitaxel. In group 3, vehicle of the compound of Example 6 was administrated 30 min prior to the administration of paclitaxel. Paw withdrawal thresholds were determined daily in both hind paws of each animal using calibrated von Frey monofilaments according to an up-down procedure as described immediately above in subpart (A) titled "Paclitaxel-induced Neuropathy." The results are shown in FIG. 14.

We claim the following:

1. A method of treating a cannabinoid receptor-mediated disease or disorder comprising administering to a subject in need thereof a therapeutically effective amount of a hydrazone compound or a pharmaceutically-acceptable salt thereof, the cannabinoid receptor-mediated disease or disorder selected from the group consisting of obesity and addiction, the hydrazone compound comprising a compound of structural Formula I:

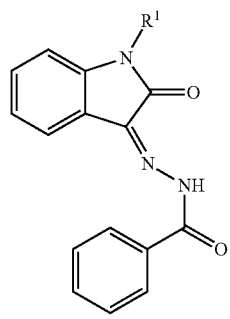

or a salt or prodrug thereof, wherein:
$R_1$ is selected from the group consisting of n-hexyl and 2-cyclohexyl ethyl.

2. The method of claim 1, the hydrazone compound comprising the structural formula IV:

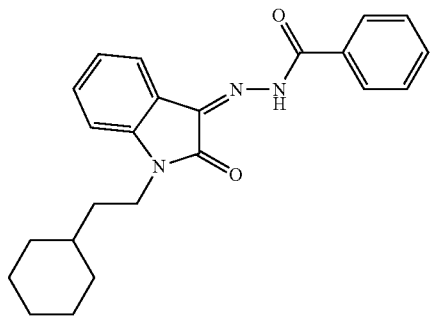 [SMILES: O=C(N/N=C1\C(=O)N(CCC2CCCCC2)c2ccccc21)c1ccccc1]

or pharmaceutically acceptable salt thereof.

3. The method of claim 1, the hydrazone compound comprising the structural formula V:

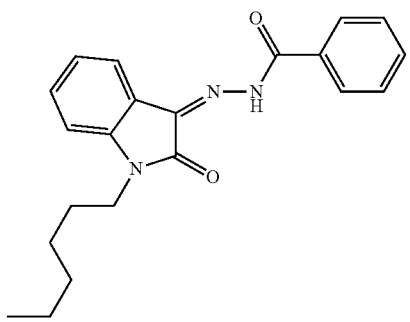 [SMILES: CCCCCCN1C(=O)/C(=N\NC(=O)c2ccccc2)c2ccccc21]

or pharmaceutically acceptable salt thereof.

4. A method of treating a cannabinoid receptor-mediated disease or disorder comprising administering to a subject in need thereof a therapeutically effective amount of a hydrazone compound or a pharmaceutically-acceptable salt thereof, the cannabinoid receptor-mediated disease or disorder selected from the group consisting of obesity and addiction, the hydrazone compound comprising a compound of structural Formula III:

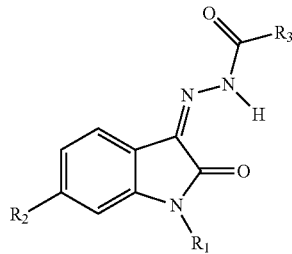

or a salt or prodrug thereof, wherein:
$R_1$ is selected from the group consisting of n-hexyl and 2-cyclohexyl ethyl;
$R_2$ is selected from the group consisting of a hydrogen atom or a methoxy;
$R_3$ is selected from the group consisting of $NR^4R^5$, aryl, heteroaryl, alkenyl, an alkynyl, an alkoxy, a cycloalkyl containing from 5 to 10 carbon atoms and containing eventually —CO—, —O—, —S—, —SO—, —SO$_2$—, —CHOH— or —NR$_{12}$—, or one of the radicals defined by the following structure:

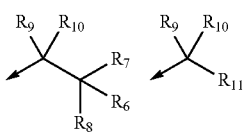

wherein $R^4$ and $R^5$ taken together form a group consisting of a radical cycloalkyl containing from 3 to 10 carbon atoms and eventually interrupted with one or more hetero atoms or by —CO—, —SO—, —SO$_2$—, —CHOH— or —NR$_{14}$—;

$R_6$ is selected from the group consisting of alkyl containing from 1 to 3 carbon atoms;

$R_7$ is selected from the group consisting of alkyl containing from 1 to 3 carbon atoms;

$R_6$ and $R_7$ taken together might form a cycloalkyl containing from 3 to 10 carbon atoms and eventually interrupted with one or more hetero atoms or by —CO—, —SO—, —SO$_2$—, —CHOH— or —NR$_{13}$—;

$R_8$ is selected from the group consisting of hydrogen and alkyl from 1 to 3 carbon atoms;

$R_9$ and $R_{10}$ vary independently and are selected from the group consisting of methyl or a hydrogen;

$R_{11}$ is selected from the group consisting of aryl, heteroaryl or an alkyl from 1 to 6 carbon atoms;

$R_{12}$ is selected from the group consisting of hydrogen or alkyl containing from 1 to 3 carbon atoms;

$R_{13}$ is selected from the group consisting of hydrogen or alkyl containing from 1 to 3 carbon atoms; and $R_{14}$ represents an alkyl containing from 1 to 3 carbon atoms.

5. A method of treating a cannabinoid receptor-mediated disease or disorder comprising administering to a subject in need thereof a therapeutically effective amount of a hydrazone compound or a pharmaceutically-acceptable salt thereof, the cannabinoid receptor-mediated disease or disorder selected from the group consisting of obesity and addiction, the hydrazone compound comprising a compound of structural Formula II:

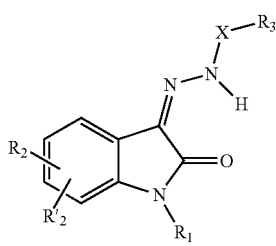

or a salt or prodrug thereof; wherein:

X is selected from the group consisting of C=O, C=S, or SO$_2$;

$R_1$ is selected from the group consisting of alkyl containing from 6 to 12 carbon atoms, a polyether, a substituted benzyl and a radical defined by the following structure:

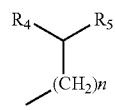

where n is an integer ranging from 1 to 4; but if $R_2$ is an alkoxy at position 6, then $R_1$ can also be selected from the group consisting of alkyl containing from 1 to 12 carbon atoms;

$R_2$ and $R'_2$ vary independently and are selected from the group consisting of hydrogen, aryl, alkyl, cycloalkyl, aralkyl, alkenyl, alkynyl, halogen, an alkoxyl or a hydroxyl;

$R_3$ is selected from the group consisting of NR$_{15}$R$_{16}$, aryl, a heteroaryl, alkenyl, an alkynyl, an alkoxyl, a cycloalkyl containing from 5 to 10 carbon atoms and containing eventually —CO—, —O—, —S—, —SO—, —SO$_2$—, —CHOH— or —NR$_{12}$— or one of the radicals defined by the following structure:

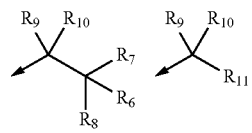

wherein $R_4$ and $R_5$ taken together form a group consisting of a radical cycloalkyl containing from 3 to 10 carbon atoms that are eventually interrupted with one or more hetero atoms or by —CO—, —SO—, —SO$_2$—, —CHOH— or —NR$_{14}$—;

$R_6$ is selected from the group consisting of alkyl containing from 1 to 3 carbon atoms;

$R_7$ is selected from the group consisting of alkyl containing from 1 to 3 carbon atoms;

$R_6$ and $R_7$ taken together can form a cycloalkyl containing from 3 to 10 carbon atoms and eventually interrupted with one or more hetero atoms or by —CO—, —SO—, —SO$_2$—, —CHOH— or —NR$_{13}$—;

$R_8$ is selected from the group consisting of hydrogen and alkyl from 1 to 3 carbon atoms;

$R_9$ and $R_{10}$ vary independently and are selected from the group consisting of methyl or a hydrogen;

$R_{11}$ is selected from the group consisting of aryl, heteroaryl, or alkyl containing from 1 to 6 carbon atoms, but if $R_2$ is alkoxyl, $R_{11}$ is heterocycloalkyl;

$R_{12}$ is selected from the group consisting of hydrogen or alkyl containing from 1 to 3 carbon atoms;

$R_{13}$ is selected from the group consisting of hydrogen or alkyl containing from 1 to 3 carbon atoms;

$R_{14}$ represents an alkyl containing from 1 to 3 carbon atoms; and $R_{15}$ and $R_{16}$ vary independently and are selected from the group consisting of an alkyl containing 1 to 6 carbon atoms or taken together might form a group consisting of a radical cycloalkyl containing from 3 to 10 carbon atoms that are eventually interrupted with one or more hetero atoms or by —CO—, —SO—, —SO$_2$—, —CHOH— or —NR$_{14}$—.

6. The method of claim 4, the hydrazone compound comprising the structural formula VI:

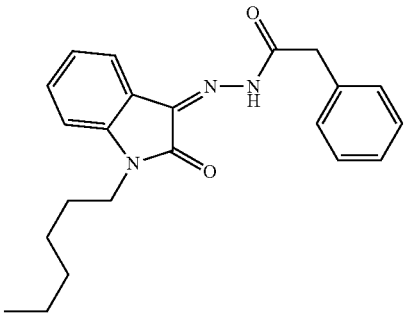 [SMILES: CCCCCCN1C(=O)/C(=N\NC(=O)Cc2ccccc2)c2ccccc21]

or pharmaceutically acceptable salt thereof.

* * * * *